US008076533B2

(12) United States Patent
Sampson et al.

(10) Patent No.: US 8,076,533 B2
(45) Date of Patent: Dec. 13, 2011

(54) METHODS AND COMPOSITIONS FOR CONTROLLING PLANT PESTS

(75) Inventors: Kimberly S. Sampson, Durham, NC (US); Daniel John Tomso, Bahama, NC (US)

(73) Assignee: Athenix Corp., Research Triangle Park, NC (US)

(*) Notice: Subject to any disclaimer, the term of this patent is extended or adjusted under 35 U.S.C. 154(b) by 0 days.

(21) Appl. No.: 13/027,816

(22) Filed: Feb. 15, 2011

(65) Prior Publication Data

US 2011/0197314 A1 Aug. 11, 2011

Related U.S. Application Data

(63) Continuation of application No. 12/718,059, filed on Mar. 5, 2010, now Pat. No. 7,919,272.

(60) Provisional application No. 61/158,133, filed on Mar. 6, 2009.

(51) Int. Cl.

| | |
|---|---|
| ***C12N 15/82*** | (2006.01) |
| ***C12N 1/20*** | (2006.01) |
| ***C12N 5/00*** | (2006.01) |
| ***C12P 21/06*** | (2006.01) |
| ***A01H 5/00*** | (2006.01) |

(52) U.S. Cl. .................... 800/279; 435/69.1; 435/252.3; 435/410; 435/320.1; 536/23.71; 536/23.1; 800/300

(58) Field of Classification Search ........................ None
See application file for complete search history.

(56) References Cited

U.S. PATENT DOCUMENTS

| | | | |
|---|---|---|---|
| 7,351,881 | B2 | 4/2008 | Carozzi et al. |
| 2004/0250311 | A1 | 12/2004 | Carozzi et al. |
| 2008/0163399 | A1 | 7/2008 | Carozzi et al. |
| 2009/0023654 | A1 | 1/2009 | Carozzi et al. |

FOREIGN PATENT DOCUMENTS

| | | |
|---|---|---|
| WO | 2007027828 | 3/2007 |

OTHER PUBLICATIONS

Ito, T. et al., "Cloning and expression of novel crystal protein genes cry39A and 39orf2 from *Bacillus thuringiensis* subsp. aizawai Bun1-14 encoding mosquitocidal proteins"; Journal of Insect Biotechnology and Sericology, Oct. 1, 2002 Japanese Society of Sericultural Science, Tsukuba, JP—ISSN 1346-8073, vol. 71, No. 3, Oct. 1, 2002, pp. 123-128, XP008115282, ISSN:1346-8073.
Ito, T. et al., "Activiation Process of the Mosquitocidal Delta-Endotoxin CRY39a Produced by *Bacillus thuringiensis* Subsp. Aizawai BUN1-14 and Binding Property to Anopheles Stephensi BBMV", Journal of Invertebrate Pathology, Sand Diego, CA, US, LNKD—DOI:10.1016/J. JIP.2006.05.007, vol. 93, No. 1, Sep. 1, 2006, pp. 29-35, XP024948627; ISSN: 0022-2011.
International Search Report of PCT/US2010/026308 mail dated Aug. 23, 2010.
Written Opinion of PCT/US2010/026308 mail dated Aug. 23, 2010.

*Primary Examiner* — Nashaat Nashed
(74) *Attorney, Agent, or Firm* — Baker Donelson Bearman Caldwell & Berkowitz, PC

(57) ABSTRACT

Compositions and methods for conferring pesticidal activity to bacteria, plants, plant cells, tissues and seeds are provided. Compositions comprising a coding sequence for a delta-endotoxin polypeptide are provided. The coding sequences can be used in DNA constructs or expression cassettes for transformation and expression in plants and bacteria. Compositions also comprise transformed bacteria, plants, plant cells, tissues, and seeds. In particular, isolated delta-endotoxin nucleic acid molecules are provided. Additionally, amino acid sequences corresponding to the polynucleotides are encompassed, and antibodies specifically binding to those amino acid sequences. In particular, the present invention provides for isolated nucleic acid molecules comprising nucleotide sequences encoding the amino acid sequence shown in SEQ ID NO:13-24 or the nucleotide sequence set forth in SEQ ID NO:1-12 and 25-44, as well as variants and fragments thereof.

19 Claims, No Drawings

SEQUENCE LISTING

```
<160> NUMBER OF SEQ ID NOS: 45

<210> SEQ ID NO 1
<211> LENGTH: 3747
<212> TYPE: DNA
<213> ORGANISM: Bacillus thuringiensis

<400> SEQUENCE: 1

atgaatggag gagagaatat gaatcaaaat aatcaaaatg aaatgcacat aatagattct      60

tcatccaatg attttagtca atcaaacaga tatccaagat acccattagc taaagagtca     120

aattataaag attggttagc tagttgtgat gaatccaatc tagatagatt gtcaactcca     180

agttctgtac aagatgcagt cgtgacaagt ttgaatattt tttcttacat ctttggtttt     240

ctagatgctg gagctacctc ggcaggtctt ggtatactag gcgtgttatt tggtcaattt     300

tggccatcaa ataataatgc ggtttgggag acttttctac gtagtgttga agaactaatt     360

gctcgagaaa tagatatcgt cgagagaaac cgaatcatgg cccaatttga tggtttaaga     420

aacgttatgt cgaattataa tggtgcactt atagattggg atggaaatcg tgataatacc     480

gcacttcaaa gtgaagtaag aagccgcttt gataatgcag atgatgcttt tgcacttcgt     540

attcctgaat ttagaataaa agattttgaa atacaatcgc tagctgtata tgcacaggct     600

gcaactcttc atttattatt attaagggat gctgttgtta atgggcagct atggggagtc     660
```

-continued

```
gatccagtaa cgactcaacg tcgttatgaa aaactggtat gtctgagtgg tgcatatgca    720
gatcattgta cattctttta tagacagggt ttggaggagt taagaggaaa agggaattgg    780
actgcattca ataattatcg tagaaacatg aatattcaag tattggatgt tatttcttta    840
ttttcaaatt atgaccctcg cttatatgga aataatacaa acacacaact tacaagagaa    900
atattcactg aaccacttgc tactcctgga tggctggata ggtattctaa tccagatcag    960
ttccaacaaa tagaatataa tcttaatcct tcaccttcat tgtcttctac tctcttaaat   1020
cttgcagcag ataccggtct tggatactat ggtgccggtg ccgtgacacc taggccaata   1080
atacaaagaa catcgatgcg tcgtttgaat acaggggcta ctgttccttt cactactgct   1140
tggcaaggcg cacctaatcc tttaatttca caacaaaagc agttgtcatt tgaaggtttt   1200
gatgttttta atatcaattc agtagtatct agggaagttt ctagtcaaac tagctcatta   1260
tttggagtcc aacaagctgt tttcacact gtgatcgctg gaggaaacat accacccact   1320
atgaaaataa ttgatctaca accaagagga aactattcca cttctgtaac gtctaatata   1380
ccaggaaaaa gatcagcaac tgcaaccgct tcagattata cccatagact atcttcgata   1440
acttcaactt cagtaggaac ggcgtataga gatagaacga atattatggc atatggatgg   1500
acgcatgtta gttcagagaa aacgaataga attctaccaa atagaattac acaaattcca   1560
tttgtaaaag gaattattac ttcgtccggg actcatgtaa gaagtggccc agatcatact   1620
gggggaagcc tcgtatcaat gggaggggat gctcaattcg gaatggtggt cacttcttca   1680
gctaggcaaa ggtatcgtgt gcgcttacgt tatgcagctt ctaattcagt ggattttcga   1740
ttaagaattt cgccattagg ggtggattat aattttacgt taccgggtgg tggaacttct   1800
tttaatccag atttacgata tagctctttc cgatatataa ctctaccaat agagtttgag   1860
acgcctaatt ctctattaaa tttctctttt gatctagaca ctttgactct tatgaatgga   1920
acatgttttt ttgacagggt tgaattcctc ccagttaatt ctatagcttt agaatatgaa   1980
ggaaaacaaa agctagaaaa agcaaagcaa gcggtggaca atttgtttac caatattggg   2040
aaaaatgctt taaaggtaga tacgacggat tatgatgtgg atcaagctgc aaatttagta   2100
gaatgtgtgc caggggaact gtacacaaaa gaaaaaatga tcctactgga tgaagtgaaa   2160
catgccaaac aactcagtgc atctcgtaat ctgattcaaa atgggaactt tgcattttat   2220
acggatgaat ggacgacaag taataatgta agtattcaaa cggataatca gatattcaaa   2280
gggaactatc tcaaaatgcc aggggcgaga gagacagagg gaggtacaac taggtttccg   2340
acgtatgtac tccaaaaaat agatgaatcc aaattaaaac cctatacacg ttataaagtc   2400
agaggctttg tcggaagtag tcatgatgtg aagttaattg tggaacgtta tggtaaagaa   2460
gtggatgcaa tcctaaatgt gagaaatgat ttagcccttg ataccgtatc ttcgtcctgt   2520
gttgaagtta atcaatgtca gtcgcaaatg tatcctatta tgcatgatgg atatctcgcg   2580
aatgtaatag atacaaattc ttatgaagag gctcagtcag atcatgctaa cttcaaaaaa   2640
gaacagggga tgtgccatca atctcatcaa tttgattttc acattgatac aggggaagta   2700
cacctaaaca agaatccagg tatttgggtt ctatttaaaa tttcttcgcc agaaggacac   2760
gcaaccttag ataacattga gttaattgaa gatggtccat tagtaggaga atcgctagcc   2820
ctcgtgaaaa aacgagaaaa gaaatggaaa catgagatga aacaagatg gctccaaaca   2880
aaagaagtgt acgaaaaggc aaaaggggca atagatgcct tatttacaga tgcacaagat   2940
cacgctataa aattcgacac aaacatttct cacattattt cagcagagca tcttgtacaa   3000
tctatgcctt atgtctataa caaatggtta tcagatgtgc caggtatgaa ttatgacatc   3060
```

```
tatacagaat tagaacgccg tattacgcag gcgtactctt tatatgaacg tagaaatatc   3120
attagaaatg gagattttaa ttacgattta aatcattggt acgcgacacc tcatgccaaa   3180
gtacaacaaa tagatagtac agctgtatta gtacttccaa actggagttc caatgtgtct   3240
caaaatctat gtgtagagca caaccgcggt tatatattac gtgtaacagc aaaaaaagaa   3300
gacatgggca aaggatatgt gactattagt gactgcaatg gaaatcagga aacacttacg   3360
ttcacttctt gtgataatta tgtatcaaac gagatcacaa atgaccaatc ggagtatcat   3420
ttcagtcaag agatgaatga acaacgtagt tataatccaa atgaggccat aaacgagcaa   3480
ttggattata gtctaggtca agtaagaaat gaacaacgtt gttatactcg aaatgccatc   3540
acaaatgacc agtcggaata tcattttagt caagagatga atgaacaacg tagttataat   3600
ccaaatgaaa ccataaatga gcaaaggaat tatgtaacaa gaaccattga tttcttccca   3660
gatacagatc aagtacgcat tgatattgga gaaactgaag gtactttcaa agtagaaagt   3720
atagaattga tttgtatgaa gagccaa                                       3747
```

```
<210> SEQ ID NO 2
<211> LENGTH: 2460
<212> TYPE: DNA
<213> ORGANISM: Bacillus thuringiensis

<400> SEQUENCE: 2

gtggtatgcc taataacgat aggaggaata gttatgaatt catatcaaaa tagaaatgaa     60
tacgaaatat tggatgcttc acccaatcat gggaacatat caaacagata tcctttcgca    120
aagaatccaa acgctatgga aaatgtcaat tataaaaatt ggttgaatgt gcgtgaagac    180
gttgcccctt ctttttttgg aggtgcactt ggaattatag ttaatctctt taaacaatat    240
gtttctttta ttaaggcgcc ttccgtttct ggtggggtag gattcttacg aactattata    300
ggtttaatga ctaatcgtaa tgtaataaat cttactatag atgatgtaca acgactaatt    360
aatcaatcat tagataatat tacccgagat gcggcaaata ctaaatttac ttcaatacaa    420
aataattata atcaatatct tctcaataga caaaactata gaaatagatc tttgcctaga    480
aacattttg tacaaagtct tcaaaatatt gagcgtgaat tgagaagtgc actagatagt    540
acttttagtt tacagaatcg agagctacta ttgttaccaa actttacgca aattgcaatg    600
ctacatttaa cagtattaag agatgctgta atatttcaag gtaacgatct aatagtgcct    660
acgattagtg aaggacctat aaatccatta ttaactcgac ctcctagtaa tacatttgag    720
gaggcacttt taactagcat aaggatatat tctaattatt gcgtaagaca atatgaagta    780
ggtttaaatc tcttgagaaa cagggggaat actagtagaa actggttgga tttcaatgcc    840
tatcgcttag aaatgacatt taaagtatta gattttgtta cattattttc attatttgat    900
acagtaaaat atccagtatc gattgtgtct gaaactgatt ctgattctac atcacccgta    960
gtttatcagt taagtagggt tatttatacg gatccagtag gtgctataag aagcgatggt   1020
cgtggttggt ttgatccacc tgtaggaact gatagggtta cttttacatc aatagaaaat   1080
gaaataccag cccctactac ttcccggcat ttatcagaat taacaatttc ttcaggcccg   1140
cttggttttg gtgtaaatcc agctaggaca cattcgtggc aggggaatcg aaatgttaat   1200
atttctgctc ctacggatgt ttctggagca atttctaatc gtacgcgaac tattcctgct   1260
agaaatattt ttagagtgaa ttcacgtgtt tatactcttg attggaggct gtatggagtt   1320
tatagagctg aatttttca gggtgctcac tcgcaagtat tttcagaaaa tcctccaaca    1380
ggtattggtg cccaaagcgc aaataacttt agatttttac ctggagaaaa ttcagaaaca   1440
```

-continued

```
ccaactccgc aagattatac tcatgtatta agcagagtag taaatgcaac tgtgggactt   1500
acaccggcaa caggaaatca acgtaactct gtattaatat ttggttggac acataaaagt   1560
ttaacctctg aaaatatata tagaatcaac gaaattacta aagtagctgc tgtgaataca   1620
agaggtaact cgggcatccg ggtaatttca ggacctggat ttacaggtgg agatttagta   1680
aggttggatc ctaacggtag cgtaagttac aattttacac ccgctaatca acaagcattg   1740
caatcgaata ttagaatacg tttacgttat gcttgtcaag ggacagcttc attaagaata   1800
acgtttggta acgcttctag ccaagttatt tcacttattt ctacaacttc atcaataaat   1860
aatcttcaat atgaaaattt ccatgttgtt aatgttccga ataacattaa ttttcaatca   1920
gtaggtactc aaataactat tcaaaatatc agtcaaaatc ctaacatatc gctagatagt   1980
attgaacttt tttccaacat acctattcca caggaacccc cttttaaccc agtggttcct   2040
gaaccaccta ttatttcagg aaattatcaa attgtaacac ctttagatcg tagaagtata   2100
atagatttaa accctaataa taatgttaca ttatggacaa ataatagatc gagtaatcaa   2160
atttggaatt tttcatatga ccaacaaaga ggtgcatatc taatacgaag tttaagaact   2220
ggaagtttag ttttatctat ggattctccc cgtactagca atgtgtttgg ttatccatct   2280
aattcagatg cttctcagtt ttggatttta gaacctaatc aagatggatt tatatttaga   2340
agtcttagag atagaaattt agttttagat gtttcaggtg gaagagtgga ccctggaacg   2400
agaataatag tttttccttt tactaattca atcaatcaaa gatttacatt gcaaagggta   2460
```

<210> SEQ ID NO 3
<211> LENGTH: 2130
<212> TYPE: DNA
<213> ORGANISM: Bacillus thuringiensis

<400> SEQUENCE: 3

```
atggagtcaa tcatatgtat gtttagagtc ctttatatca gaaattatga gcatacagga     60
ggaataaaaa tgaagccgta tcaaaatgaa aatgaatatg aaatattgga tgccttacca    120
aagtattcga acatcgtcaa tgtttattca aggtatccgt tagcaaataa tccacaagtt    180
cctttacaaa atacaagtta taaagattgg cttaatatgt gtcaaactat tactccactt    240
tgtactccta tagacattga tagtaaatta gtcgctaccg ctatagggat actaggcgct    300
atattcaaag ctatgcctgg tccaggatca gctgtaggat tatttttaaa aactttttca    360
acaataatac ctattctttg gccaaatgac aacacaccga tatggaaaga gttcacaaaa    420
caaggattgc aactttttag accggaatta ggcagagatg caatagaaat tataggcaac    480
gacgtacagt ccggcttcaa tgcgttaaaa gaccacatga acgactttga gactaagttt    540
gaaatctggg acaaagatag aactcaaact aatgcaacat atctcataac tgcatttggc    600
gttgttaacg gtaaaattat cgaccttaaa aatcaattct taataaaccc cgcaaatcaa    660
cccgcatttc taaatctcta tgcacaaact gccaatattg atttgatttt atatcaaaga    720
ggggccgtat atggagataa ttgggcaaaa gctataaatg atagttccat atctccgttt    780
aatagttcgc aaattttta tgactcttta aaagctaaaa taaaagagta tactaattat    840
tgtgcagaaa catatagaaa cagtttaact atactcaaaa atcaacccaa tatccaatgg    900
gatatatata atagatatcg tagagaggcg actttaggtg cattagattt agttgcatta    960
ttcccaaatt acgatatatg taaatatcca atctcaacaa aaacagaact tactagaaaa   1020
gtttatatgc catcattcta tttacaagca cttcaacata gtaacataga agcattggaa   1080
aaccaactta cacatccccc atcattattt acttggttaa acgaattaaa cctttataca   1140
```

-continued

```
atacgtgaaa atttcaatcc agctttacag gtatcttcat tgtcaggtct tcaagctaaa   1200

tatcgttata cccaaaattc gactatactt cctaatccgc cggctcaagg aatcacaaat   1260

ggcacaccaa taccaataat agggttaaat aacttgttta tttataaact atcaatgtca   1320

caatatcgtc atccaaatga ttgtgtacca atagctggaa tttccgatat gacctttttat   1380

aaaagtgact ataatggcaa tgcttccgca actcaaactt atcaagcagg tagaaactcc   1440

aataatgtca tagatacatt tatgaatggt ccacaaaatg catcaagctc aaataatatt   1500

tctattaacc aaacaaacca tatactatct gatattaaaa tgaattacgc tcgatctggc   1560

ggagtgtatg attttggata ttcatttgct tggacacata ctagtgtaga tcctgataat   1620

ctaattgttc cgaatagaat tacacaaatt ccagctgtta aagctaactg tttgtcttca   1680

ccagctagag taattgcagg gcctggtcat acaggaggag atttagttgc tcttctaaac   1740

ggtggtactc aagctggtag aatgcaaatc caatgtaaaa caggtagctt tactggagct   1800

tccagacgtt atggtatacg catgcgttat gctgcaaata atgcatttac agtgagtcta   1860

tcatatactt tacagggtgg taatacaata ggtacaacat ttattaccga acgtacattt   1920

tcaagaccta ataatataat accaacggat ttaaaatacg aggagtttaa atataaagaa   1980

tataatcaaa ttattacaat gacttcacct caaaatacaa tagtaactat agctattcaa   2040

caactaaatc cgatcccaaa tgatcaatta attattgata gaatcgaatt ttatccagtg   2100

gatcaaggtg tagtagcttg tccagtgaac                                    2130
```

<210> SEQ ID NO 4
<211> LENGTH: 1689
<212> TYPE: DNA
<213> ORGANISM: Bacillus thuringiensis

<400> SEQUENCE: 4

```
gtgaattcta tgtttacaag tggggcgaaa aacaggttga aaatagaaac aacagatcat     60

gaaatagatc aggctgcaat ttctataaag gctatgttag aggaagaaca ttcacaagag    120

aaaatgatgt tatgggatga agtaaaacat gcaaaatacc tcagtcattc tcgtaatcta    180

cttcaaaatg gtgattttga agatttattt aatggctgga ctacaagtaa taatatgtcc    240

attcagaacg ataattcaac ttttaaagga caatatttaa atatgcctgg agcacgagac    300

atatatggaa ccatatttcc aacatatgtt tatcaaaaaa tagaggaatc caaattaaaa    360

tcatatacac gttatcgagt aagaggattt gtgggaagta gtaaagattt aaaattaatg    420

gtaacacgtt acgggaaaga aattgatgct agtatggatg ttccaaatga tttggcatat    480

atgcagccta acccttcatg tggggattat cgctgtgact catcatccca gtctatgatg    540

aatcaagggt atcctacacc atatacagat ggatatgctt ccgatatgta tgcatgcccg    600

tcaaacttag gtaaaaaaca tgtgaagtgt cacgatcgtc atccatttga ttttcatatt    660

gacaccggag aagtagatat aaatacaaac ttagggattt tagtcttatt taaaatttcc    720

aatcccgatg gatacgctac attaggaaat ctagaagtga ttgaagaagg gccactaaca    780

ggcgaagcat tggcacatgt gaaacaaaag gaaaagaaat ggaatcaaca catggagaaa    840

aaacgttggg aaacacaaca agcctatgat ccagcaaaac aagcagtaaa tgcattattc    900

acaaatgcac aaggagacga attacactat catattactt tagatcatat tcagaacgcc    960

gatcagttgg tacagtcgat tccttatgta caccatgctt ggttaccgga tgctccaggt   1020

atgaactatg atgtatatca aggcttaaac gcacgtatca tgcaggctta caatttatat   1080

gatgcacgaa atgtcataac aaatggcgac tttacacaag gattaatggg atggcacgca   1140
```

-continued

```
acaggaaagg cagcggtaca acagatggat ggagcttctg tattagttct atcaaactgg   1200

agtgcggggg tatctcaaaa cttgcatgcc caagatcatc atggatatgt gttacgtgtg   1260

attgccaaaa aagaaggacc tggaaaaggg tatgtaacga tgatggattg taacggtaat   1320

caggaaacgc tgaagttcac ttcttgtgaa gaaggataca tgacaaaaac agtagaggta   1380

ttcccagaaa gtgatcgtgt acggattgaa ataggagaaa ccgaaggtac attttatata   1440

gatagcatcg agttgctttg tatgcaagga tatgctaaca ataataatcc gcagacaggt   1500

aatatgtatg agcaaagtaa taatcagaat acgagcgatg tgtatcatca agggtataca   1560

aacaactata accaagactc tagtagtatg tataatcaaa attatactaa caatgatgac   1620

ctgcattccg gttgtacatg taaccaaggg cataactttg gctgtacatg taatcaagga   1680

tataaccgt                                                           1689
```

<210> SEQ ID NO 5
<211> LENGTH: 2070
<212> TYPE: DNA
<213> ORGANISM: Bacillus thuringiensis

<400> SEQUENCE: 5

```
gtgaaaagta tgaattcata tcaaaataaa aatgaatatg aaatattgga tgcttcacaa     60

aataactcta ctatgtctaa tcgttatcca aggtatccac tagcaaatga cccacaagcc    120

tctatgcaga atacgaatta taaagattgg ttaaatatgt gcgattcaaa cacacaattt    180

gttggtgata taagcacgta ttctagtcct gaagctgctt taagtgtacg agatgctgtt    240

ttaacgggta ttaacactgc tgggactata ctttcgaatt taggggtccc ttttgctagt    300

caatcatttg gaatgattgg taggataata ggtattttat ggccgggacc tgacccattt    360

gcagcactta tggttcttgt tgaagagctt attaatcaaa ggataaatga tgagataaga    420

aaccatgctc ttttagaatt agcgggttta aagggcatta tggatctata tcgaactaga    480

tggcgtgcat gggaccttaa taaagataat cctgaaactc gagaagcagt acgagcgcag    540

tatcgaaccg ctgataactt ttttatacaa aacatgccaa aatttgggcg tgaagaccat    600

ggggttttat tgttaccagt atatgcgcaa gccgcgaata tgcatttaat tttattaaga    660

gatgcttatg tatttggaac agggtgggga ttaggtcctg gtgaagttcg tgataattat    720

acaagactac aggagaagat tagagagtat aaagatcatt gtgtaacatt ctataatcag    780

ggtttaaatc gatttaatcg ctcaaatgct caagattggg tgagctttaa taggtttcgt    840

acagatatga cattaacagt attggatcta gcaatattat ttccaaacta tgatccgcgc    900

atatatccat cggcagtaaa aacagaattg actagggaaa tttatacaga tccagtaggg    960

tttactgggg tattagggag tggaggtagg acttaccctt ggtataatcc taatgatacg   1020

tcctttgcta ctatggaaaa tagcgccaga cgacgacctt cttttaccac ttggcttaat   1080

cgcattcgta tatttacagg tcatataggt aatttttctg ctgcgggaaa tgtttgggga   1140

gggcatgaat tatttgaacg tagcaataac ggttctgaaa taattcagag atttggtaat   1200

acgaatacct cttatactcc tgttagaaat tgggatttca cgaatcagaa tcgtactgtt   1260

ttcagtattg cttcaaccgc tcgcgtgtta ttagcgggat cagagggaaa tgctcatcgt   1320

ccgagtcagt atggcgtctc gagagttgat atgcatacag caataggtgg taatacttct   1380

ggtggacagt ttatatacga agtacctaat gttcattcat cccaaaatat tttatcagaa   1440

ttaccaggag agaatcagca aagaccagac gcaagaaatc acagccacat attatcttat   1500

atatcaaatt ttgatgcaaa acgaggtggt actgtcggca acgttagact tttaacgtat   1560
```

```
ggttggacgc ataccagtat ggatcgtaat aatcgtcttg aacgagatag aattactcaa   1620

atagatgctg ttaaaggttg ggggggagtt actgggtctg tcataccagg acctactgga   1680

gggagtttgg taacgatccc tagtaatcct tggagcgttt cccttagagt tcaagcacca   1740

caaatacaaa caaattatcg tattcgtttg cgttttgctt gtgtatggcc gggggcgcat   1800

catatgtggg taacctacgg cggtatttcc caccctgttc aattatgcaa taatccatca   1860

tcaggtcgcc catcaaacaa tcttctagag agcgattttg gctatgttgt tgttccaggt   1920

actttttcgc catcaataaa tcccgaaata cgattttcag ctatcagtaa tgcccccgtg   1980

ctagacaaaa ttgaatttat tccacttgac atttataatg agcattttgt agaagaaaga   2040

gcaaagacaa taaatgatct atttattaat                                    2070
```

<210> SEQ ID NO 6
<211> LENGTH: 1713
<212> TYPE: DNA
<213> ORGANISM: Bacillus thuringiensis

<400> SEQUENCE: 6

```
gtgaaaaagg ttgtgaatcc tatgtttaca agtggcgcga aaaatacgtt aaaaatagaa     60

acgacagatt atgaaataga tcaagtggca aattctatag aatgtatgtc agatgaacaa    120

aatccacagg aaaaaatgat gctatgggat gaaataaaac aggcaaaaca acttagtcgg    180

tctcgtaatt tactccacaa tggtgatttt gaggatttat ttagaggctg gacaacaagt    240

actcatatta cgattcaggc ggataatccg attttcaaag gaaattatat taatatacca    300

ggggcaggag atattgatgg gacgctattc ccgagctata tctatcaaaa aatagaggaa    360

tccaaattaa aatcaaatac acgttataga gtaagagggt ttgtggggag tagtaaaaat    420

ctaaaattag tggtaacacg ttacgggaaa gaaattgatg ctagtatgga tgttccaaat    480

gatttagcct atatgcagcc taacccttca tgtggggatt atcgctgtga atcctcgtcc    540

cagtatgtga gccaagggta tccgacagca ccatatacag atggatatgc ttctgagatg    600

tatgcatgcc cgtcagaccg agttaaaaaa catgtgaagt gtcacgatcg ccatccattt    660

gattttcata ttgacatcgg agaattagat ataaatacaa acgtaggtat ttgggtctta    720

tttaaaattt ctaatccaga tggatatgct acattaggga atttagaagt gattgaagaa    780

ggaccactaa caggtgaagc attaacgcat gcgaaacaaa aggaaaagaa atggaaacaa    840

cacatggaga agaagcgatt ggaaacacaa caagcctatg atccggcaaa acaggcagta    900

gatgcattat tcacaaatgc acaaggagaa gagttacact atcatattac tttagatcat    960

attcagaacg ccaatcagtt ggtacagtcg attccttatg tacaccatgc ttggttaccg   1020

gatgctccag gtatgaacta tgatgtatat caagggttaa acgcacgtat catgcaagct   1080

tataatttat atgctgcacg aaatgtcata acaaatggtg actttacaca aggattacag   1140

ggatggcacg caacaggaaa ggcaacggta caacaaatgg atggagcttc tgtattagtt   1200

ctgtcaaact ggagtgctgg ggtatctcag aatctgcatg cccaagatca tcatggatat   1260

gtgttacgtg tgattgccaa aaaagaagga cctggaaaag ggtatgtaac gatgatggat   1320

tgtaacggca atcaggagac actgaagttc acttcttgtg aagaaggata tatgacaaaa   1380

acagtagaga tattcccaga aagtgatcgt gtacggattg aaataggaga aaccgaaggt   1440

acgttttatg tagatagcat cgagttgctt tgtatgcaag gatatgctat caataataac   1500

ccacacacgg gtaatatgta tgagcaaagt tataatggaa tttataatca gaatacgagc   1560

gatgtgtatc accaagggta tacaaacaac tataaccaag actctagtag tatgtataat   1620
```

caaaattata ctaacaatga tgaccagcat tccgattgca catgtaatca agggcataat 1680
tctggctgta catgtaatca aggatataac cgt 1713

<210> SEQ ID NO 7
<211> LENGTH: 1881
<212> TYPE: DNA
<213> ORGANISM: Bacillus thuringiensis

<400> SEQUENCE: 7
gtgaaaaata tgaattcata tcaaaataaa aatgaatatg aaatattgga tacttcacca 60
aacaactcta ctatgtctac tcttcatcca aggtacccac tagcaaagga tccatacaag 120
cctatgcgaa atacaaacta taaagaatgg ctagctatgt gtgcaaataa taatcaagta 180
cctattgatc cccttgataa tacctgggca ggtgttatgg cagctctttt cgcctctgct 240
gcagctatag cgggattaat gtcagcagtt ccagttttct ctgttgtagc cacaggaaca 300
gccttagcag cagccttaac acctatttta ttccctagta atggcccaga tgtatccacc 360
cagcttatga gtaatacaga agctttacta aaaagagagc tagatactta tgttagagca 420
agggcagatt cagaatttca agccttagaa gctcaaagag aatttttcaa atcagctttt 480
gattattgga aattatatcc tacaaatagc aacgctatag ctacggttgc tgctaggttc 540
cacacagtaa atggtgcttt tgtaacagca atgcgtttat tcagaacggc aggttatgaa 600
gcattactgt taccagttta tgcacaagcg gcgcgtcttc atttactcca tttacgagat 660
ggtgtcctgt ttgcgaatga atgggggcta gctaaagacc ctggagactt acatgaccaa 720
gaatttaata aatatgctgc tgaatatgcg gattattgtg aatcaacgta taatacagag 780
ctaaaccgca ttaaaactgc tccaggtaaa acatggcttg actataatca gtaccgacga 840
attatgacaa ttgctgtttt ggatatagct gctaaatttt caattttaaa tcctcgccta 900
tatagattac ctttgcaaga agaaattctc actcgaaaaa tatatactga tcctgttaat 960
ttctcacctg gtccttcaat cgcagatgat gaaaatagat atacagtccc actatccctt 1020
gttacacaat tagtcaactc aagattattt actaacgtgg catctgctca aaatgctgga 1080
tttattggaa atcaaaatcg ttataaaaat ataggcgttg gcgacccagt tgatggtcct 1140
ataattggac aatcagtata cgaaaaagtg gatgcaggta taccgacaaa tgaatgggtt 1200
tatgaagttg gtgtaaatgg tatacagaat gattatccac gtaatatagg tttgagaaag 1260
ggttctacaa ctgcatttac agatcattta gctggaagtc agtataattt aggtccttta 1320
actagggtct ctataccaac taaagacaat gccccaataa ataatactaa ttttactcat 1380
cgattatcag atataattct tcctggaaat aaggggtcat cttttgcatg gactcatgtt 1440
gatgtcgatc ctacaggaaa ctatttatca acaactaaga ttaatttaat acctgctaca 1500
aaagcatcta aaataccact ttctttctat ctaagaaagg gaccaggatt tatagggggga 1560 gatttagtca gattaggaag tggcttcgaa tgttcttata agtttaattt caaatcccca 1620
ggtagctcag ctaattttag aattcgtata cgttatgcag gtgcgggtag tggtcagggt 1680
gctgatggtc aggtatattt taaattaggg aattatacat ctccaactac tccttggggc 1740
catactggat ttgactatgg aaatgtgaag tataatcaat ttagagtatt agagcttttt 1800
ggaactgcag aaaacattac agacaacgac ttgaagatta tagtatggac aggttcaagt 1860
gctcaggatt ttttatctag a 1881

<210> SEQ ID NO 8
<211> LENGTH: 1698
<212> TYPE: DNA

<213> ORGANISM: Bacillus thuringiensis

<400> SEQUENCE: 8

```
gtgagtccta tgtatattaa tacgatgaaa aatacattaa aactagaaac gacagattat      60
gaaatagatc aagccgccat ttctatagaa tgcatgtcta atgaacaaaa tccacaggaa     120
aaaatgatat tatgggatga agtaaaacag gcaaaacaac tcagtcaatc tcgtaattta     180
ctctacaatg gtgattttga agatgcatca aacggctgga aaacaagtta tacgattgaa     240
attggaaagt atagttccat ttttaaaggg cagtaccttc atatgtttgg ggcaagagat     300
gttttaggtg aagtgtttcc aacatatgtg tatcaaaaaa ttgatgaatc taaattaaaa     360
ccctatacac gttatcgagt aagaggattt gtgggaagta gtaaagatct aaaattagtg     420
gtaacccgtt acgggaaaga aattgacgcc attatggatg ttccagatga tttggcctat     480
atgcagccta cccctcatg  tggggattat cgttgtgaat cagcgtcaca gtatgtgagc     540
caagggtatc ctacaccata tggagatgga tatgcttctg ataggtatgc atgcccgtca     600
gaccgagtta aaaaacatgt gaagtgtcac aatcgccatc catttgattt tcatattgac     660
accggagaat tagatataaa tacaaacgta ggtatttggg tcttatttaa aatttctaat     720
ccagatggat acgctacatt agggaattta gaagtgattg aagaaggacc aataacaggt     780
gaagcattaa cgcatgcgaa acaaaaggaa aagaaatgga atcaacacat ggagaaagcg     840
caaatcgaaa cacagcaagc ctatgatccg gcaaaacagg cagtagatgc attattcaca     900
aatgcacaag gagaagagtt acactatcat attactttag atcatattca gaacgccaat     960
cagttggtac agtcgattcc ttatgtacac catgcttggt taccggatgc tccaggtatg    1020
aactatgatg tatatcaaga gttaaacgca cgtatcatgc aagcacgcta tttacatgat    1080
gcacgaaatg tcataacaaa tggtgacttt acacaaggat tacagggatg gcacgcaaca    1140
ggaaaggcaa cggtacaaca aatggatgga gcttctgtat tagttctgtc aaactggagt    1200
gctggggtat ctcagaatct gcatgcccaa gatcatcatg gatatgtgtt acgtgtgatt    1260
gccaaaaaag aaggacctgg aaaagggtat gtaacgatga tggattgtaa cggcaatcag    1320
gagacactga agttcacttc ttgtgaagaa ggatatatga caaaaacagt agagatattc    1380
ccagaaagtg atcgtgtacg gattgaaata ggagaaaccg aaggtacgtt ttatgtagat    1440
agcatcgagt tgctttgtat gcaaggatat gctatcaata ataacccaca cacgggtaat    1500
atgtatgagc aaagttataa tggaatttat aatcagaata cgagcgatgt gtatcaccaa    1560
gggtatacaa acaactataa ccaagactct agtagtatgt ataatcaaaa ttatactaac    1620
aatgatgacc agcattccga ttgcacatgt aatcaagggc ataattctgg ctgtacatgt    1680
aatcaaggat ataaccgt                                                  1698
```

<210> SEQ ID NO 9
<211> LENGTH: 888
<212> TYPE: DNA
<213> ORGANISM: Bacillus thuringiensis

<400> SEQUENCE: 9

```
atgaaaaagt taatgttttc tttagtagca acaactatga gtatgggatt aattcttgga      60
tctgcacctg taaaagcaga cgtaagcaac aagaatagtg catatcagga tattgatgag     120
agagttaaga aaatggcgca gagtgctgct tggggggggac aagagtatag aaatcataat     180
ataaaagata ttgaattaaa gggtaatctt atagatggtt ctatgattga aaattcagaa     240
gtattaactg tttcatcaga tattttagaa aataaattag gacatacagt aaatatgcct     300
```

agtactggtt atgaacatga atttgaagaa acgactaata caactaatac aagtggatgg 360
acatttggct ataattataa cgcaagtttt tcagtattaa tggtttcagc ttcacaaagt 420
tttagtgttg aatataatat gtctacttca aacactcatg aaaaaaagga gaaaagaaaa 480
tttactgtcc cttcaataga agttccagtt cctgctggga aaaaatacaa agttgaatat 540
gtgtttgaaa aagttaaagt ttcaggaaaa aataaaattg atgcaaatct ctatggtgat 600
gttacttatt attataataa tcagccgatg tcaccacagc ttttatattc agtacaagga 660
cttgcagctg ataagcaagg gtttgagcaa gtcataagag attcagctgt aggaaacgat 720
agatttggaa ttaagactac aggtattggt cagtttagca ctgagtttgg aacacgtcta 780
actagaactc ttacagacat tactgatact agaaatccag taaaagtaga gacgaaaaat 840
gtcccagttg agtttaaaac actttcaatt gatactagag taattaaa 888

<210> SEQ ID NO 10
<211> LENGTH: 924
<212> TYPE: DNA
<213> ORGANISM: Bacillus thuringiensis

<400> SEQUENCE: 10
atgaaaaaaa atagaatgtt gcttaaatgg atgtgtggtt taacaattgg aatcgggagt 60
ttaacaggag gtagtttaaa tgcttttgcg gatgaagtct ctgattcttt agcagacgtg 120
ggttttcttt atggggatta tctttataaa actaaacaac atccacaagg aacattacct 180
atcacctatc caatgagaga aatcaataat tatcaaatta ttgataaatc tgtttcgcaa 240
gttgggagta cggaatatga agaaggtcaa actctgtatg tcgatgatga tgtttttgac 300
aataagacag gtactgatca aacttttaaa acaattcagt ttgaaaaaga attttcagaa 360
acagccacat cgtcaacaac acattctgtg ggtacaagcc tagaagaaag tgtgaaattt 420
gatttctttg tgggtgaagg ttcagccaaa ttcacagtaa actataattt tagtaaaaca 480
ggttctctct caacaagcaa taaaataaaa tacacgttac cttctcaatc aattaatgta 540
cctgctaaca agaaatatga agttatatgt gttcttgaaa ctaaaaaagc aaaggctaat 600
gttcaattta acgtcgatgt tcttggtaat gcgaaatatg tatatagcaa taattcaccg 660
tatacaccta aatacgaaag tggtgctact atgttgaaaa ctttaaatga aaaaaatcct 720
actcctagcg tctcatggtt aggtaaagaa tgggaaaaat gggaatatca cgatggaaaa 780
gcgagataca aaaatggaag tggacagtt tcagctgaat atggtacaag aatggtactt 840
gtaattaacg atataacaaa taataaaaca agaggtagta aagagattgc tagaatccct 900
gttacaccaa tccaaaaaca aatg 924

<210> SEQ ID NO 11
<211> LENGTH: 3732
<212> TYPE: DNA
<213> ORGANISM: Bacillus thuringiensis

<400> SEQUENCE: 11
atgaatggag gagagaatat gaatcaaaat aatcaaaatg aaatgcaaat aatagattct 60
tcatccaatg attttagtca atcaaacagg tatccaagat atccattagc taaagagtca 120
aattataaag attggttagc tagttgtgat gaatccaatg tagatacatt atcagctaca 180
agtaatgtaa gggcttcagt atcgagagct ctgggtattg tgaatcagat tttgggtttt 240
cttggtcttg gatttattgg aacagggctt ggtgtattaa gtgatttatt taattcattt 300
tggccatcaa atgataactc gatttgggaa tcttttctac gtagtgttga agaactcatt 360

-continued

```
gatcgacgag tacgtgaagt cgagagattt cgtatcgaat cccaatttac tggtttaaga    420
aacgttatgt cgaattataa tggtgctctt cgtgattgga atggaaatcg taataatcta    480
gcacttcaaa gtgaagtaag aagccgcttt gataattcag atgatgcttt tgcatctcgt    540
atgcctgaat ttagaataga aggttttgaa atacaatcac tagctgtata tgcacaggct    600
gcaactctcc atttattatt attaagggat ggcgttgtta atgggctgca atggggattc    660
gatatcgtta cggttaaccg tctttatgaa aaactagtat gtctgagtgg tgcatatgca    720
gatcattgta cattatttta tagacaaggt ttggaggagt taaggaacag agggaattgg    780
aatgcattca ataattatcg tagagacatg actcttcaag tattggatgt catttcttta    840
tttccaaatt atgaccctcg cctatatgac attaatacaa acacacaact tacaagagaa    900
atatacactg aaccacttgc tattcctgga tggcttaatt ctcattccaa tccaactcag    960
ttccaacaaa tagaaaatga tcttatccgc tcaccttcag tgttttctaa tctcgagact   1020
ctttttatgg aagctggttt tgcattcttc caagccggca tagctagaca agcagtatta   1080
agaacacgta cgtctagttt aaatatgaat cgcactgctg tcatcgtaac tccttggcaa   1140
ggggcacctc atcctaatgt ttcacatgaa cttcaagtga cccttcaaga tcggaatgtt   1200
tttaatatca attcagtagt aggtagggaa atttctagtc aaaccggctt attatttggg   1260
gtccaacaag ccacttttca ctttgtatgg gcaggcggaa acgcagctac gacaacacaa   1320
ttcaatctac caccgatttc tggacattca acttctataa catctaatat acccggaaca   1380
aactcaacaa ctccaactgg ttcagattat acccatagac tatcttcgat aacttcaact   1440
tcagtaggaa cgtggcagag agatagaacg aatattatgg catatggatg gactcatgtt   1500
agtgcagagc gtactaatag gattataccg aatagaatta cacaaatccc agctgtaaaa   1560
ggatcactgt ttagtgataa tccaccaaac acatcacgaa cacgtgtaga aaatggccct   1620
ggtcatactg gggtggact cgtagttatg gacggaggaa ctagtgtatt acagatgaga    1680
gtcacttctt cagcaaggca aaggtatgat atgcgtttac gttatgtagc tcttgctcca   1740
gctactgttg aagtaagaat tccggaatta ggggggcatg ttaggtttca gatgccaatg   1800
actgcaacgg ggttacctgc gcctctacca tacagccatt tgcgatatgt ggatatcccg   1860
ctgaggtttg agacacccca tggtgaaaat acttggacgt ttgaactaca gactacgttt   1920
gcagcagttg caattgacag agtcgaattc ataccagtta atgctacagc tttagaatat   1980
gaaggaaaac gacatctaga aaaggcaaag aaagccgtgg gtgatctgtt tatcaataat   2040
ggaaaagagg ctttaaaagt agatacgacg gattatgatg tggatcaagc tgccaatcta   2100
gtagaatgta tgccagagga actgtacaca aaagaaaaaa tgatcctact tgatgaagtg   2160
aaacatgcga agagattcag tcaatcccgt aatctcattc aaaatggaga ctttgaattt   2220
gctacagatg gatggatgac aagtagtaat gtcatcgttc aggcggataa tacagtattc   2280
aaagggaaat atctcaatat gccaggggca atagaaacag atacaagtac gttcccgact   2340
tatatatacc aaaaaataga tgaatccaga ttaaagccat atacacgcta taaagtcagg   2400
ggctttgtcg gaagtagtca tgatgtgagg ctaattgtgg aacgcaatgg taaagaagtg   2460
gatgcactcc taaatgtaag aaatgatttg tcccttgata ccgtagctcc ttcctgtatt   2520
gaagctaatc aaccttatcc tatcatccat gatggatgtc tcacgaatgt aatagataca   2580
aattcttatg aagaggctca gtccggtcat gctaactgca aaaaagaaca tggaatgtgc   2640
catcagtctc atcaatttga ttttcacatt gatacagggg aaatacacac aaacaagaat   2700
ccaggtattt gggttctgtt taaaatttct tcgccagaag gacacgcaac cttagataac   2760
```

-continued

```
attgagttaa ttgaagatgg tccgttagta ggagaatcgc tagccttcgt gaaaaaacaa   2820

gaaaagaaat gggaaaatga gatggaaaca agatggctcc aaacaaaaga agtatatgaa   2880

aaggcaaaag gggaaataga ttccttattt acagatgcac aagatcaagc tttaaaattc   2940

gacacaaaca tttctcatat tatttcagca gagcatcttg tacaatccat gccttatgta   3000

tataacaatt ggttatcaga tgtgccaggt atgaattatg acatctatac agaattagaa   3060

cgtcgtatta cgcaggcata ctctttatat gaacatagaa atatcattaa aaatggagac   3120

tttgattatg gtttaaatca ttggcacgcg acgcctcatg cgaaagtgca acaaatagat   3180

ggtacagctg tattagtact tccaaactgg agttccaatg tgtctcaaaa tctatgtgta   3240

gagcacaacc gcggttatat attacgtgta acagcaaaaa aagaagacat gggcaaagga   3300

tatgtgacta ttagtgactg caatggaaat caggaaacac ttacgttcac ttcttgtgct   3360

aattatgtag caaacgaaat cacaaatgac caatcggagt atcacttcag tcaagagatg   3420

aatgaacaac gtggttataa tccaaatgaa accataaaca agcaattaga ttatagtcta   3480

gatcaagtaa gaaatgaaca acgttgttat aatccaaatg aaatcacaaa tgaccagtcg   3540

gaatatcatt acagtcaaga gatgaatgaa caacgttgtt ataatccaaa tgaaatcata   3600

aacgagcaca ggaattatgt aacaagaacc attgatttct tcccagatac aaatcaagtg   3660

cgcattgata ttggagaaac tgaaggtact ttcaaagtag aaagtataga attgatttgt   3720

atgaagagcc aa                                                       3732
```

<210> SEQ ID NO 12
<211> LENGTH: 1563
<212> TYPE: DNA
<213> ORGANISM: Bacillus thuringiensis

<400> SEQUENCE: 12

```
gtgaccaaat cagaatttat ccaaaattca tgcagaaaaa tgcaatcaaa agtgagggtt     60

attattctaa gtactaatga tcctgtagtc aataataata ctttagatat aacagaaata    120

aaagacctag ctcatttatc tcaagctatc atgttagcta ataattttca agctgctctt    180

gtacccactt catcagaatt tggacaggat gtattaagat ttgatgtaaa tcaaggaatt    240

agcatagcta ataacattta tcctaaagct gtagatataa attatatatc acgtacgctt    300

tctcaaagta acaaccaagt aaattctatg ataaatatgg tggtaaatga attgaaatta    360

ttattaggga taaatcttgc tgattcagtg ttacaacaat taacatcttt agttgcgtat    420

acatttacaa atttatatac acagcaaaat tctgcttggg ttttttgggg gaaacaagct    480

tctaatcaaa caaattatac ttataatatt gtgtttgcaa ttcaaaatgc tcaaacaggt    540

aactttatga aagctattcc tatgggattt gaaatttcag cttatgctgt caaagaacag    600

gtattattct ttaccattca agattacgca agttatagcg ttaaaataca ggcaattaat    660

gtcacgcagc ctttaattaa tagtagctat ggaagtttaa gtggcgtgta taatataata    720

accgctctaa ataatataag tgttataact atgtcaaatt cggatgaaaa tgttaattta    780

tggtatgata atgatgattt aaaccaaaaa tggattcttg aatttaatca taatcactat    840

gcttatataa tccgaaacct tagcaatcgc tctttagtat taacatggga tagtacttca    900

ggttctaata atgtttttgc tacaaactat caaggaaacg atgaacaatt ttggattatt    960

caagatacgg ataatgatta tttttattta tcaaatatga gagatactca atatgtatta   1020

gagatagctg gctctgtgtt ttataacgga acaaatgtta tagttaataa aaaaacaagc   1080

agtttaaatc aaaaattttc aattaatcgt ataaatcgtc aaattcagaa tggtatatat   1140
```

-continued

```
aatattacaa cctacctaaa tgctagcagt gttataacta tgtcaacaga ttataatatt   1200

aatgtacacg attatcctgt taatttatgg tttaaaaatg atagtattaa tcaaaaatgg   1260

atttttgaat ttgatagtga taaatccgct tatcgagtta gaagtgtcag taatccatct   1320

ttatttctat catggccggt agcttctttt acaaatcgcg ctgctgttac acctaatcca   1380

agagacaatg aatatttttg gtttcttcaa agcgctggat tgggtacttt ttatttagta   1440

agtatgagag acactcgata tgtattagaa gtggaaaatt ccaatattga taacggaaca   1500

aatattatag ttaatcaaag aacaggtaat tttaatcaga gattttatat agaaaatatt   1560

aat                                                                  1563


<210> SEQ ID NO 13
<211> LENGTH: 1249
<212> TYPE: PRT
<213> ORGANISM: Bacillus thuringiensis

<400> SEQUENCE: 13

Met Asn Gly Gly Glu Asn Met Asn Gln Asn Asn Gln Asn Glu Met His
1               5                   10                  15

Ile Ile Asp Ser Ser Ser Asn Asp Phe Ser Gln Ser Asn Arg Tyr Pro
            20                  25                  30

Arg Tyr Pro Leu Ala Lys Glu Ser Asn Tyr Lys Asp Trp Leu Ala Ser
        35                  40                  45

Cys Asp Glu Ser Asn Leu Asp Arg Leu Ser Thr Pro Ser Ser Val Gln
    50                  55                  60

Asp Ala Val Val Thr Ser Leu Asn Ile Phe Ser Tyr Ile Phe Gly Phe
65                  70                  75                  80

Leu Asp Ala Gly Ala Thr Ser Ala Gly Leu Gly Ile Leu Gly Val Leu
                85                  90                  95

Phe Gly Gln Phe Trp Pro Ser Asn Asn Asn Ala Val Trp Glu Thr Phe
            100                 105                 110

Leu Arg Ser Val Glu Glu Leu Ile Ala Arg Glu Ile Asp Ile Val Glu
        115                 120                 125

Arg Asn Arg Ile Met Ala Gln Phe Asp Gly Leu Arg Asn Val Met Ser
    130                 135                 140

Asn Tyr Asn Gly Ala Leu Ile Asp Trp Asp Gly Asn Arg Asp Asn Thr
145                 150                 155                 160

Ala Leu Gln Ser Glu Val Arg Ser Arg Phe Asp Asn Ala Asp Asp Ala
                165                 170                 175

Phe Ala Leu Arg Ile Pro Glu Phe Arg Ile Lys Asp Phe Glu Ile Gln
            180                 185                 190

Ser Leu Ala Val Tyr Ala Gln Ala Ala Thr Leu His Leu Leu Leu Leu
        195                 200                 205

Arg Asp Ala Val Val Asn Gly Gln Leu Trp Gly Val Asp Pro Val Thr
    210                 215                 220

Thr Gln Arg Arg Tyr Glu Lys Leu Val Cys Leu Ser Gly Ala Tyr Ala
225                 230                 235                 240

Asp His Cys Thr Phe Phe Tyr Arg Gln Gly Leu Glu Glu Leu Arg Gly
                245                 250                 255

Lys Gly Asn Trp Thr Ala Phe Asn Asn Tyr Arg Arg Asn Met Asn Ile
            260                 265                 270

Gln Val Leu Asp Val Ile Ser Leu Phe Ser Asn Tyr Asp Pro Arg Leu
        275                 280                 285

Tyr Gly Asn Asn Thr Asn Thr Gln Leu Thr Arg Glu Ile Phe Thr Glu
    290                 295                 300
```

```
Pro Leu Ala Thr Pro Gly Trp Leu Asp Arg Tyr Ser Asn Pro Asp Gln
305                 310                 315                 320

Phe Gln Gln Ile Glu Tyr Asn Leu Asn Pro Ser Pro Ser Leu Ser Ser
                325                 330                 335

Thr Leu Leu Asn Leu Ala Ala Asp Thr Gly Leu Gly Tyr Tyr Gly Ala
            340                 345                 350

Gly Ala Val Thr Pro Arg Pro Ile Ile Gln Arg Thr Ser Met Arg Arg
        355                 360                 365

Leu Asn Thr Gly Ala Thr Val Pro Phe Thr Thr Ala Trp Gln Gly Ala
    370                 375                 380

Pro Asn Pro Leu Ile Ser Gln Gln Lys Gln Leu Ser Phe Glu Gly Phe
385                 390                 395                 400

Asp Val Phe Asn Ile Asn Ser Val Val Ser Arg Glu Val Ser Ser Gln
                405                 410                 415

Thr Ser Ser Leu Phe Gly Val Gln Gln Ala Val Phe His Thr Val Ile
            420                 425                 430

Ala Gly Gly Asn Ile Pro Pro Thr Met Lys Ile Ile Asp Leu Gln Pro
        435                 440                 445

Arg Gly Asn Tyr Ser Thr Ser Val Thr Ser Asn Ile Pro Gly Lys Arg
    450                 455                 460

Ser Ala Thr Ala Thr Ala Ser Asp Tyr Thr His Arg Leu Ser Ser Ile
465                 470                 475                 480

Thr Ser Thr Ser Val Gly Thr Ala Tyr Arg Asp Arg Thr Asn Ile Met
                485                 490                 495

Ala Tyr Gly Trp Thr His Val Ser Ser Glu Lys Thr Asn Arg Ile Leu
            500                 505                 510

Pro Asn Arg Ile Thr Gln Ile Pro Phe Val Lys Gly Ile Ile Thr Ser
        515                 520                 525

Ser Gly Thr His Val Arg Ser Gly Pro Asp His Thr Gly Gly Ser Leu
    530                 535                 540

Val Ser Met Gly Gly Asp Ala Gln Phe Gly Met Val Val Thr Ser Ser
545                 550                 555                 560

Ala Arg Gln Arg Tyr Arg Val Arg Leu Arg Tyr Ala Ala Ser Asn Ser
                565                 570                 575

Val Asp Phe Arg Leu Arg Ile Ser Pro Leu Gly Val Asp Tyr Asn Phe
            580                 585                 590

Thr Leu Pro Gly Gly Gly Thr Ser Phe Asn Pro Asp Leu Arg Tyr Ser
        595                 600                 605

Ser Phe Arg Tyr Ile Thr Leu Pro Ile Glu Phe Glu Thr Pro Asn Ser
    610                 615                 620

Leu Leu Asn Phe Ser Phe Asp Leu Asp Thr Leu Thr Leu Met Asn Gly
625                 630                 635                 640

Thr Cys Phe Phe Asp Arg Val Glu Phe Leu Pro Val Asn Ser Ile Ala
                645                 650                 655

Leu Glu Tyr Glu Gly Lys Gln Lys Leu Glu Lys Ala Lys Gln Ala Val
            660                 665                 670

Asp Asn Leu Phe Thr Asn Ile Gly Lys Asn Ala Leu Lys Val Asp Thr
        675                 680                 685

Thr Asp Tyr Asp Val Asp Gln Ala Ala Asn Leu Val Glu Cys Val Pro
    690                 695                 700

Gly Glu Leu Tyr Thr Lys Glu Lys Met Ile Leu Leu Asp Glu Val Lys
705                 710                 715                 720

His Ala Lys Gln Leu Ser Ala Ser Arg Asn Leu Ile Gln Asn Gly Asn
```

```
            725                 730                 735

Phe Ala Phe Tyr Thr Asp Glu Trp Thr Thr Ser Asn Asn Val Ser Ile
        740                 745                 750

Gln Thr Asp Asn Gln Ile Phe Lys Gly Asn Tyr Leu Lys Met Pro Gly
    755                 760                 765

Ala Arg Glu Thr Glu Gly Gly Thr Thr Arg Phe Pro Thr Tyr Val Leu
    770                 775                 780

Gln Lys Ile Asp Glu Ser Lys Leu Lys Pro Tyr Thr Arg Tyr Lys Val
785                 790                 795                 800

Arg Gly Phe Val Gly Ser Ser His Asp Val Lys Leu Ile Val Glu Arg
                805                 810                 815

Tyr Gly Lys Glu Val Asp Ala Ile Leu Asn Val Arg Asn Asp Leu Ala
            820                 825                 830

Leu Asp Thr Val Ser Ser Ser Cys Val Glu Val Asn Gln Cys Gln Ser
        835                 840                 845

Gln Met Tyr Pro Ile Met His Asp Gly Tyr Leu Ala Asn Val Ile Asp
    850                 855                 860

Thr Asn Ser Tyr Glu Glu Ala Gln Ser Asp His Ala Asn Phe Lys Lys
865                 870                 875                 880

Glu Gln Gly Met Cys His Gln Ser His Gln Phe Asp Phe His Ile Asp
                885                 890                 895

Thr Gly Glu Val His Leu Asn Lys Asn Pro Gly Ile Trp Val Leu Phe
            900                 905                 910

Lys Ile Ser Ser Pro Glu Gly His Ala Thr Leu Asp Asn Ile Glu Leu
        915                 920                 925

Ile Glu Asp Gly Pro Leu Val Gly Glu Ser Leu Ala Leu Val Lys Lys
    930                 935                 940

Arg Glu Lys Lys Trp Lys His Glu Met Lys Thr Arg Trp Leu Gln Thr
945                 950                 955                 960

Lys Glu Val Tyr Glu Lys Ala Lys Gly Ala Ile Asp Ala Leu Phe Thr
                965                 970                 975

Asp Ala Gln Asp His Ala Ile Lys Phe Asp Thr Asn Ile Ser His Ile
            980                 985                 990

Ile Ser Ala Glu His Leu Val Gln Ser Met Pro Tyr Val Tyr Asn Lys
        995                 1000                1005

Trp Leu Ser Asp Val Pro Gly Met Asn Tyr Asp Ile Tyr Thr Glu Leu
    1010                1015                1020

Glu Arg Arg Ile Thr Gln Ala Tyr Ser Leu Tyr Glu Arg Arg Asn Ile
1025                1030                1035                1040

Ile Arg Asn Gly Asp Phe Asn Tyr Asp Leu Asn His Trp Tyr Ala Thr
                1045                1050                1055

Pro His Ala Lys Val Gln Gln Ile Asp Ser Thr Ala Val Leu Val Leu
            1060                1065                1070

Pro Asn Trp Ser Ser Asn Val Ser Gln Asn Leu Cys Val Glu His Asn
        1075                1080                1085

Arg Gly Tyr Ile Leu Arg Val Thr Ala Lys Lys Glu Asp Met Gly Lys
    1090                1095                1100

Gly Tyr Val Thr Ile Ser Asp Cys Asn Gly Asn Gln Glu Thr Leu Thr
1105                1110                1115                1120

Phe Thr Ser Cys Asp Asn Tyr Val Ser Asn Glu Ile Thr Asn Asp Gln
                1125                1130                1135

Ser Glu Tyr His Phe Ser Gln Glu Met Asn Glu Gln Arg Ser Tyr Asn
            1140                1145                1150
```

```
Pro Asn Glu Ala Ile Asn Glu Gln Leu Asp Tyr Ser Leu Gly Gln Val
        1155                1160                1165

Arg Asn Glu Gln Arg Cys Tyr Thr Arg Asn Ala Ile Thr Asn Asp Gln
    1170                1175                1180

Ser Glu Tyr His Phe Ser Gln Glu Met Asn Glu Gln Arg Ser Tyr Asn
1185                1190                1195                1200

Pro Asn Glu Thr Ile Asn Glu Gln Arg Asn Tyr Val Thr Arg Thr Ile
                1205                1210                1215

Asp Phe Phe Pro Asp Thr Asp Gln Val Arg Ile Asp Ile Gly Glu Thr
            1220                1225                1230

Glu Gly Thr Phe Lys Val Glu Ser Ile Glu Leu Ile Cys Met Lys Ser
        1235                1240                1245

Gln


<210> SEQ ID NO 14
<211> LENGTH: 820
<212> TYPE: PRT
<213> ORGANISM: Bacillus thuringiensis

<400> SEQUENCE: 14

Met Val Cys Leu Ile Thr Ile Gly Gly Ile Val Met Asn Ser Tyr Gln
1               5                   10                  15

Asn Arg Asn Glu Tyr Glu Ile Leu Asp Ala Ser Pro Asn His Gly Asn
            20                  25                  30

Ile Ser Asn Arg Tyr Pro Phe Ala Lys Asn Pro Asn Ala Met Glu Asn
        35                  40                  45

Val Asn Tyr Lys Asn Trp Leu Asn Val Arg Glu Asp Val Ala Pro Ser
    50                  55                  60

Phe Phe Gly Gly Ala Leu Gly Ile Ile Val Asn Leu Phe Lys Gln Tyr
65                  70                  75                  80

Val Ser Phe Ile Lys Ala Pro Ser Val Ser Gly Gly Val Gly Phe Leu
                85                  90                  95

Arg Thr Ile Ile Gly Leu Met Thr Asn Arg Asn Val Ile Asn Leu Thr
            100                 105                 110

Ile Asp Asp Val Gln Arg Leu Ile Asn Gln Ser Leu Asp Asn Ile Thr
        115                 120                 125

Arg Asp Ala Ala Asn Thr Lys Phe Thr Ser Ile Gln Asn Asn Tyr Asn
    130                 135                 140

Gln Tyr Leu Leu Asn Arg Gln Asn Tyr Arg Asn Arg Ser Leu Pro Arg
145                 150                 155                 160

Asn Ile Phe Val Gln Ser Leu Gln Asn Ile Glu Arg Glu Leu Arg Ser
                165                 170                 175

Ala Leu Asp Ser Thr Phe Ser Leu Gln Asn Arg Glu Leu Leu Leu Leu
            180                 185                 190

Pro Asn Phe Thr Gln Ile Ala Met Leu His Leu Thr Val Leu Arg Asp
        195                 200                 205

Ala Val Ile Phe Gln Gly Asn Asp Leu Ile Val Pro Thr Ile Ser Glu
    210                 215                 220

Gly Pro Ile Asn Pro Leu Leu Thr Arg Pro Pro Ser Asn Thr Phe Glu
225                 230                 235                 240

Glu Ala Leu Leu Thr Ser Ile Arg Ile Tyr Ser Asn Tyr Cys Val Arg
                245                 250                 255

Gln Tyr Glu Val Gly Leu Asn Leu Leu Arg Asn Arg Gly Asn Thr Ser
            260                 265                 270

Arg Asn Trp Leu Asp Phe Asn Ala Tyr Arg Leu Glu Met Thr Phe Lys
```

-continued

```
        275                 280                 285

Val Leu Asp Phe Val Thr Leu Phe Ser Leu Phe Asp Thr Val Lys Tyr
    290                 295                 300

Pro Val Ser Ile Val Ser Glu Thr Asp Ser Asp Ser Thr Ser Pro Val
305                 310                 315                 320

Val Tyr Gln Leu Ser Arg Val Ile Tyr Thr Asp Pro Val Gly Ala Ile
                325                 330                 335

Arg Ser Asp Gly Arg Gly Trp Phe Asp Pro Pro Val Gly Thr Asp Arg
            340                 345                 350

Val Thr Phe Thr Ser Ile Glu Asn Glu Ile Pro Ala Pro Thr Thr Ser
        355                 360                 365

Arg His Leu Ser Glu Leu Thr Ile Ser Ser Gly Pro Leu Gly Phe Gly
    370                 375                 380

Val Asn Pro Ala Arg Thr His Ser Trp Gln Gly Asn Arg Asn Val Asn
385                 390                 395                 400

Ile Ser Ala Pro Thr Asp Val Ser Gly Ala Ile Ser Asn Arg Thr Arg
                405                 410                 415

Thr Ile Pro Ala Arg Asn Ile Phe Arg Val Asn Ser Arg Val Tyr Thr
            420                 425                 430

Leu Asp Trp Arg Leu Tyr Gly Val Tyr Arg Ala Glu Phe Phe Gln Gly
        435                 440                 445

Ala His Ser Gln Val Phe Ser Glu Asn Pro Pro Thr Gly Ile Gly Ala
    450                 455                 460

Gln Ser Ala Asn Asn Phe Arg Phe Leu Pro Gly Glu Asn Ser Glu Thr
465                 470                 475                 480

Pro Thr Pro Gln Asp Tyr Thr His Val Leu Ser Arg Val Val Asn Ala
                485                 490                 495

Thr Val Gly Leu Thr Pro Ala Thr Gly Asn Gln Arg Asn Ser Val Leu
            500                 505                 510

Ile Phe Gly Trp Thr His Lys Ser Leu Thr Ser Glu Asn Ile Tyr Arg
        515                 520                 525

Ile Asn Glu Ile Thr Lys Val Ala Ala Val Asn Thr Arg Gly Asn Ser
    530                 535                 540

Gly Ile Arg Val Ile Ser Gly Pro Gly Phe Thr Gly Gly Asp Leu Val
545                 550                 555                 560

Arg Leu Asp Pro Asn Gly Ser Val Ser Tyr Asn Phe Thr Pro Ala Asn
                565                 570                 575

Gln Gln Ala Leu Gln Ser Asn Ile Arg Ile Arg Leu Arg Tyr Ala Cys
            580                 585                 590

Gln Gly Thr Ala Ser Leu Arg Ile Thr Phe Gly Asn Ala Ser Ser Gln
        595                 600                 605

Val Ile Ser Leu Ile Ser Thr Thr Ser Ser Ile Asn Asn Leu Gln Tyr
    610                 615                 620

Glu Asn Phe His Val Val Asn Val Pro Asn Asn Ile Asn Phe Gln Ser
625                 630                 635                 640

Val Gly Thr Gln Ile Thr Ile Gln Asn Ile Ser Gln Asn Pro Asn Ile
                645                 650                 655

Ser Leu Asp Ser Ile Glu Leu Phe Ser Asn Ile Pro Ile Pro Gln Glu
            660                 665                 670

Pro Pro Phe Asn Pro Val Val Pro Glu Pro Pro Ile Ile Ser Gly Asn
        675                 680                 685

Tyr Gln Ile Val Thr Pro Leu Asp Arg Arg Ser Ile Ile Asp Leu Asn
    690                 695                 700
```

```
Pro Asn Asn Asn Val Thr Leu Trp Thr Asn Asn Arg Ser Ser Asn Gln
705                 710                 715                 720

Ile Trp Asn Phe Ser Tyr Asp Gln Gln Arg Gly Ala Tyr Leu Ile Arg
                725                 730                 735

Ser Leu Arg Thr Gly Ser Leu Val Leu Ser Met Asp Ser Pro Arg Thr
            740                 745                 750

Ser Asn Val Phe Gly Tyr Pro Ser Asn Ser Asp Ala Ser Gln Phe Trp
        755                 760                 765

Ile Leu Glu Pro Asn Gln Asp Gly Phe Ile Phe Arg Ser Leu Arg Asp
    770                 775                 780

Arg Asn Leu Val Leu Asp Val Ser Gly Gly Arg Val Asp Pro Gly Thr
785                 790                 795                 800

Arg Ile Ile Val Phe Pro Phe Thr Asn Ser Ile Asn Gln Arg Phe Thr
                805                 810                 815

Leu Gln Arg Val
            820
```

<210> SEQ ID NO 15
<211> LENGTH: 710
<212> TYPE: PRT
<213> ORGANISM: Bacillus thuringiensis

<400> SEQUENCE: 15

```
Met Glu Ser Ile Ile Cys Met Phe Arg Val Leu Tyr Ile Arg Asn Tyr
1               5                   10                  15

Glu His Thr Gly Gly Ile Lys Met Lys Pro Tyr Gln Asn Glu Asn Glu
            20                  25                  30

Tyr Glu Ile Leu Asp Ala Leu Pro Lys Tyr Ser Asn Ile Val Asn Val
        35                  40                  45

Tyr Ser Arg Tyr Pro Leu Ala Asn Asn Pro Gln Val Pro Leu Gln Asn
    50                  55                  60

Thr Ser Tyr Lys Asp Trp Leu Asn Met Cys Gln Thr Ile Thr Pro Leu
65                  70                  75                  80

Cys Thr Pro Ile Asp Ile Asp Ser Lys Leu Val Ala Thr Ala Ile Gly
                85                  90                  95

Ile Leu Gly Ala Ile Phe Lys Ala Met Pro Gly Pro Gly Ser Ala Val
            100                 105                 110

Gly Leu Phe Leu Lys Thr Phe Ser Thr Ile Ile Pro Ile Leu Trp Pro
        115                 120                 125

Asn Asp Asn Thr Pro Ile Trp Lys Glu Phe Thr Lys Gln Gly Leu Gln
    130                 135                 140

Leu Phe Arg Pro Glu Leu Gly Arg Asp Ala Ile Glu Ile Ile Gly Asn
145                 150                 155                 160

Asp Val Gln Ser Gly Phe Asn Ala Leu Lys Asp His Met Asn Asp Phe
                165                 170                 175

Glu Thr Lys Phe Glu Ile Trp Asp Lys Asp Arg Thr Gln Thr Asn Ala
            180                 185                 190

Thr Tyr Leu Ile Thr Ala Phe Gly Val Val Asn Gly Lys Ile Ile Asp
        195                 200                 205

Leu Lys Asn Gln Phe Leu Ile Asn Pro Ala Asn Gln Pro Ala Phe Leu
    210                 215                 220

Asn Leu Tyr Ala Gln Thr Ala Asn Ile Asp Leu Ile Leu Tyr Gln Arg
225                 230                 235                 240

Gly Ala Val Tyr Gly Asp Asn Trp Ala Lys Ala Ile Asn Asp Ser Ser
                245                 250                 255
```

-continued

```
Ile Ser Pro Phe Asn Ser Ser Gln Ile Phe Tyr Asp Ser Leu Lys Ala
            260                 265                 270

Lys Ile Lys Glu Tyr Thr Asn Tyr Cys Ala Glu Thr Tyr Arg Asn Ser
        275                 280                 285

Leu Thr Ile Leu Lys Asn Gln Pro Asn Ile Gln Trp Asp Ile Tyr Asn
    290                 295                 300

Arg Tyr Arg Arg Glu Ala Thr Leu Gly Ala Leu Asp Leu Val Ala Leu
305                 310                 315                 320

Phe Pro Asn Tyr Asp Ile Cys Lys Tyr Pro Ile Ser Thr Lys Thr Glu
                325                 330                 335

Leu Thr Arg Lys Val Tyr Met Pro Ser Phe Tyr Leu Gln Ala Leu Gln
            340                 345                 350

His Ser Asn Ile Glu Ala Leu Glu Asn Gln Leu Thr His Pro Pro Ser
        355                 360                 365

Leu Phe Thr Trp Leu Asn Glu Leu Asn Leu Tyr Thr Ile Arg Glu Asn
    370                 375                 380

Phe Asn Pro Ala Leu Gln Val Ser Ser Leu Ser Gly Leu Gln Ala Lys
385                 390                 395                 400

Tyr Arg Tyr Thr Gln Asn Ser Thr Ile Leu Pro Asn Pro Pro Ala Gln
                405                 410                 415

Gly Ile Thr Asn Gly Thr Pro Ile Pro Ile Ile Gly Leu Asn Asn Leu
            420                 425                 430

Phe Ile Tyr Lys Leu Ser Met Ser Gln Tyr Arg His Pro Asn Asp Cys
        435                 440                 445

Val Pro Ile Ala Gly Ile Ser Asp Met Thr Phe Tyr Lys Ser Asp Tyr
    450                 455                 460

Asn Gly Asn Ala Ser Ala Thr Gln Thr Tyr Gln Ala Gly Arg Asn Ser
465                 470                 475                 480

Asn Asn Val Ile Asp Thr Phe Met Asn Gly Pro Gln Asn Ala Ser Ser
                485                 490                 495

Ser Asn Asn Ile Ser Ile Asn Gln Thr Asn His Ile Leu Ser Asp Ile
            500                 505                 510

Lys Met Asn Tyr Ala Arg Ser Gly Gly Val Tyr Asp Phe Gly Tyr Ser
        515                 520                 525

Phe Ala Trp Thr His Thr Ser Val Asp Pro Asp Asn Leu Ile Val Pro
    530                 535                 540

Asn Arg Ile Thr Gln Ile Pro Ala Val Lys Ala Asn Cys Leu Ser Ser
545                 550                 555                 560

Pro Ala Arg Val Ile Ala Gly Pro Gly His Thr Gly Gly Asp Leu Val
                565                 570                 575

Ala Leu Leu Asn Gly Gly Thr Gln Ala Gly Arg Met Gln Ile Gln Cys
            580                 585                 590

Lys Thr Gly Ser Phe Thr Gly Ala Ser Arg Arg Tyr Gly Ile Arg Met
        595                 600                 605

Arg Tyr Ala Ala Asn Asn Ala Phe Thr Val Ser Leu Ser Tyr Thr Leu
    610                 615                 620

Gln Gly Gly Asn Thr Ile Gly Thr Thr Phe Ile Thr Glu Arg Thr Phe
625                 630                 635                 640

Ser Arg Pro Asn Asn Ile Ile Pro Thr Asp Leu Lys Tyr Glu Glu Phe
                645                 650                 655

Lys Tyr Lys Glu Tyr Asn Gln Ile Ile Thr Met Thr Ser Pro Gln Asn
            660                 665                 670

Thr Ile Val Thr Ile Ala Ile Gln Gln Leu Asn Pro Ile Pro Asn Asp
        675                 680                 685
```

```
Gln Leu Ile Ile Asp Arg Ile Glu Phe Tyr Pro Val Asp Gln Gly Val
    690                 695                 700

Val Ala Cys Pro Val Asn
705                 710


<210> SEQ ID NO 16
<211> LENGTH: 563
<212> TYPE: PRT
<213> ORGANISM: Bacillus thuringiensis

<400> SEQUENCE: 16

Met Asn Ser Met Phe Thr Ser Gly Ala Lys Asn Arg Leu Lys Ile Glu
1               5                   10                  15

Thr Thr Asp His Glu Ile Asp Gln Ala Ala Ile Ser Ile Lys Ala Met
            20                  25                  30

Leu Glu Glu Glu His Ser Gln Glu Lys Met Met Leu Trp Asp Glu Val
        35                  40                  45

Lys His Ala Lys Tyr Leu Ser His Ser Arg Asn Leu Leu Gln Asn Gly
    50                  55                  60

Asp Phe Glu Asp Leu Phe Asn Gly Trp Thr Thr Ser Asn Asn Met Ser
65                  70                  75                  80

Ile Gln Asn Asp Asn Ser Thr Phe Lys Gly Gln Tyr Leu Asn Met Pro
                85                  90                  95

Gly Ala Arg Asp Ile Tyr Gly Thr Ile Phe Pro Thr Tyr Val Tyr Gln
            100                 105                 110

Lys Ile Glu Glu Ser Lys Leu Lys Ser Tyr Thr Arg Tyr Arg Val Arg
        115                 120                 125

Gly Phe Val Gly Ser Ser Lys Asp Leu Lys Leu Met Val Thr Arg Tyr
    130                 135                 140

Gly Lys Glu Ile Asp Ala Ser Met Asp Val Pro Asn Asp Leu Ala Tyr
145                 150                 155                 160

Met Gln Pro Asn Pro Ser Cys Gly Asp Tyr Arg Cys Asp Ser Ser Ser
                165                 170                 175

Gln Ser Met Met Asn Gln Gly Tyr Pro Thr Pro Tyr Thr Asp Gly Tyr
            180                 185                 190

Ala Ser Asp Met Tyr Ala Cys Pro Ser Asn Leu Gly Lys Lys His Val
        195                 200                 205

Lys Cys His Asp Arg His Pro Phe Asp Phe His Ile Asp Thr Gly Glu
    210                 215                 220

Val Asp Ile Asn Thr Asn Leu Gly Ile Leu Val Leu Phe Lys Ile Ser
225                 230                 235                 240

Asn Pro Asp Gly Tyr Ala Thr Leu Gly Asn Leu Glu Val Ile Glu Glu
                245                 250                 255

Gly Pro Leu Thr Gly Glu Ala Leu Ala His Val Lys Gln Lys Glu Lys
            260                 265                 270

Lys Trp Asn Gln His Met Glu Lys Lys Arg Trp Glu Thr Gln Gln Ala
        275                 280                 285

Tyr Asp Pro Ala Lys Gln Ala Val Asn Ala Leu Phe Thr Asn Ala Gln
    290                 295                 300

Gly Asp Glu Leu His Tyr His Ile Thr Leu Asp His Ile Gln Asn Ala
305                 310                 315                 320

Asp Gln Leu Val Gln Ser Ile Pro Tyr Val His His Ala Trp Leu Pro
                325                 330                 335

Asp Ala Pro Gly Met Asn Tyr Asp Val Tyr Gln Gly Leu Asn Ala Arg
            340                 345                 350
```

Ile Met Gln Ala Tyr Asn Leu Tyr Asp Ala Arg Asn Val Ile Thr Asn
355 360 365

Gly Asp Phe Thr Gln Gly Leu Met Gly Trp His Ala Thr Gly Lys Ala
370 375 380

Ala Val Gln Gln Met Asp Gly Ala Ser Val Leu Val Leu Ser Asn Trp
385 390 395 400

Ser Ala Gly Val Ser Gln Asn Leu His Ala Gln Asp His His Gly Tyr
405 410 415

Val Leu Arg Val Ile Ala Lys Lys Glu Gly Pro Gly Lys Gly Tyr Val
420 425 430

Thr Met Met Asp Cys Asn Gly Asn Gln Glu Thr Leu Lys Phe Thr Ser
435 440 445

Cys Glu Glu Gly Tyr Met Thr Lys Thr Val Glu Val Phe Pro Glu Ser
450 455 460

Asp Arg Val Arg Ile Glu Ile Gly Glu Thr Glu Gly Thr Phe Tyr Ile
465 470 475 480

Asp Ser Ile Glu Leu Leu Cys Met Gln Gly Tyr Ala Asn Asn Asn Asn
485 490 495

Pro Gln Thr Gly Asn Met Tyr Glu Gln Ser Asn Asn Gln Asn Thr Ser
500 505 510

Asp Val Tyr His Gln Gly Tyr Thr Asn Asn Tyr Asn Gln Asp Ser Ser
515 520 525

Ser Met Tyr Asn Gln Asn Tyr Thr Asn Asn Asp Asp Leu His Ser Gly
530 535 540

Cys Thr Cys Asn Gln Gly His Asn Phe Gly Cys Thr Cys Asn Gln Gly
545 550 555 560

Tyr Asn Arg

<210> SEQ ID NO 17
<211> LENGTH: 690
<212> TYPE: PRT
<213> ORGANISM: Bacillus thuringiensis

<400> SEQUENCE: 17

Met Lys Ser Met Asn Ser Tyr Gln Asn Lys Asn Glu Tyr Glu Ile Leu
1 5 10 15

Asp Ala Ser Gln Asn Asn Ser Thr Met Ser Asn Arg Tyr Pro Arg Tyr
20 25 30

Pro Leu Ala Asn Asp Pro Gln Ala Ser Met Gln Asn Thr Asn Tyr Lys
35 40 45

Asp Trp Leu Asn Met Cys Asp Ser Asn Thr Gln Phe Val Gly Asp Ile
50 55 60

Ser Thr Tyr Ser Ser Pro Glu Ala Ala Leu Ser Val Arg Asp Ala Val
65 70 75 80

Leu Thr Gly Ile Asn Thr Ala Gly Thr Ile Leu Ser Asn Leu Gly Val
85 90 95

Pro Phe Ala Ser Gln Ser Phe Gly Met Ile Gly Arg Ile Ile Gly Ile
100 105 110

Leu Trp Pro Gly Pro Asp Pro Phe Ala Ala Leu Met Val Leu Val Glu
115 120 125

Glu Leu Ile Asn Gln Arg Ile Asn Asp Glu Ile Arg Asn His Ala Leu
130 135 140

Leu Glu Leu Ala Gly Leu Lys Gly Ile Met Asp Leu Tyr Arg Thr Arg
145 150 155 160

-continued

```
Trp Arg Ala Trp Asp Leu Asn Lys Asp Asn Pro Glu Thr Arg Glu Ala
                165                 170                 175

Val Arg Ala Gln Tyr Arg Thr Ala Asp Asn Phe Phe Ile Gln Asn Met
            180                 185                 190

Pro Lys Phe Gly Arg Glu Asp His Gly Val Leu Leu Leu Pro Val Tyr
        195                 200                 205

Ala Gln Ala Ala Asn Met His Leu Ile Leu Leu Arg Asp Ala Tyr Val
    210                 215                 220

Phe Gly Thr Gly Trp Gly Leu Gly Pro Gly Glu Val Arg Asp Asn Tyr
225                 230                 235                 240

Thr Arg Leu Gln Glu Lys Ile Arg Glu Tyr Lys Asp His Cys Val Thr
                245                 250                 255

Phe Tyr Asn Gln Gly Leu Asn Arg Phe Asn Arg Ser Asn Ala Gln Asp
            260                 265                 270

Trp Val Ser Phe Asn Arg Phe Arg Thr Asp Met Thr Leu Thr Val Leu
        275                 280                 285

Asp Leu Ala Ile Leu Phe Pro Asn Tyr Asp Pro Arg Ile Tyr Pro Ser
    290                 295                 300

Ala Val Lys Thr Glu Leu Thr Arg Glu Ile Tyr Thr Asp Pro Val Gly
305                 310                 315                 320

Phe Thr Gly Val Leu Gly Ser Gly Gly Arg Thr Tyr Pro Trp Tyr Asn
                325                 330                 335

Pro Asn Asp Thr Ser Phe Ala Thr Met Glu Asn Ser Ala Arg Arg Arg
            340                 345                 350

Pro Ser Phe Thr Thr Trp Leu Asn Arg Ile Arg Ile Phe Thr Gly His
        355                 360                 365

Ile Gly Asn Phe Ser Ala Ala Gly Asn Val Trp Gly Gly His Glu Leu
    370                 375                 380

Phe Glu Arg Ser Asn Asn Gly Ser Glu Ile Ile Gln Arg Phe Gly Asn
385                 390                 395                 400

Thr Asn Thr Ser Tyr Thr Pro Val Arg Asn Trp Asp Phe Thr Asn Gln
                405                 410                 415

Asn Arg Thr Val Phe Ser Ile Ala Ser Thr Ala Arg Val Leu Leu Ala
            420                 425                 430

Gly Ser Glu Gly Asn Ala His Arg Pro Ser Gln Tyr Gly Val Ser Arg
        435                 440                 445

Val Asp Met His Thr Ala Ile Gly Gly Asn Thr Ser Gly Gly Gln Phe
    450                 455                 460

Ile Tyr Glu Val Pro Asn Val His Ser Ser Gln Asn Ile Leu Ser Glu
465                 470                 475                 480

Leu Pro Gly Glu Asn Gln Gln Arg Pro Asp Ala Arg Asn His Ser His
                485                 490                 495

Ile Leu Ser Tyr Ile Ser Asn Phe Asp Ala Lys Arg Gly Gly Thr Val
            500                 505                 510

Gly Asn Val Arg Leu Leu Thr Tyr Gly Trp Thr His Thr Ser Met Asp
        515                 520                 525

Arg Asn Asn Arg Leu Glu Arg Asp Arg Ile Thr Gln Ile Asp Ala Val
    530                 535                 540

Lys Gly Trp Gly Gly Val Thr Gly Ser Val Ile Pro Gly Pro Thr Gly
545                 550                 555                 560

Gly Ser Leu Val Thr Ile Pro Ser Asn Pro Trp Ser Val Ser Leu Arg
                565                 570                 575

Val Gln Ala Pro Gln Ile Gln Thr Asn Tyr Arg Ile Arg Leu Arg Phe
            580                 585                 590
```

Ala Cys Val Trp Pro Gly Ala His His Met Trp Val Thr Tyr Gly Gly
595 600 605

Ile Ser His Pro Val Gln Leu Cys Asn Asn Pro Ser Ser Gly Arg Pro
610 615 620

Ser Asn Asn Leu Leu Glu Ser Asp Phe Gly Tyr Val Val Val Pro Gly
625 630 635 640

Thr Phe Ser Pro Ser Ile Asn Pro Glu Ile Arg Phe Ser Ala Ile Ser
645 650 655

Asn Ala Pro Val Leu Asp Lys Ile Glu Phe Ile Pro Leu Asp Ile Tyr
660 665 670

Asn Glu His Phe Val Glu Glu Arg Ala Lys Thr Ile Asn Asp Leu Phe
675 680 685

Ile Asn
690

<210> SEQ ID NO 18
<211> LENGTH: 571
<212> TYPE: PRT
<213> ORGANISM: Bacillus thuringiensis

<400> SEQUENCE: 18

Met Lys Lys Val Val Asn Pro Met Phe Thr Ser Gly Ala Lys Asn Thr
1 5 10 15

Leu Lys Ile Glu Thr Thr Asp Tyr Glu Ile Asp Gln Val Ala Asn Ser
20 25 30

Ile Glu Cys Met Ser Asp Glu Gln Asn Pro Gln Glu Lys Met Met Leu
35 40 45

Trp Asp Glu Ile Lys Gln Ala Lys Gln Leu Ser Arg Ser Arg Asn Leu
50 55 60

Leu His Asn Gly Asp Phe Glu Asp Leu Phe Arg Gly Trp Thr Thr Ser
65 70 75 80

Thr His Ile Thr Ile Gln Ala Asp Asn Pro Ile Phe Lys Gly Asn Tyr
85 90 95

Ile Asn Ile Pro Gly Ala Gly Asp Ile Asp Gly Thr Leu Phe Pro Ser
100 105 110

Tyr Ile Tyr Gln Lys Ile Glu Glu Ser Lys Leu Lys Ser Asn Thr Arg
115 120 125

Tyr Arg Val Arg Gly Phe Val Gly Ser Ser Lys Asn Leu Lys Leu Val
130 135 140

Val Thr Arg Tyr Gly Lys Glu Ile Asp Ala Ser Met Asp Val Pro Asn
145 150 155 160

Asp Leu Ala Tyr Met Gln Pro Asn Pro Ser Cys Gly Asp Tyr Arg Cys
165 170 175

Glu Ser Ser Ser Gln Tyr Val Ser Gln Gly Tyr Pro Thr Ala Pro Tyr
180 185 190

Thr Asp Gly Tyr Ala Ser Glu Met Tyr Ala Cys Pro Ser Asp Arg Val
195 200 205

Lys Lys His Val Lys Cys His Asp Arg His Pro Phe Asp Phe His Ile
210 215 220

Asp Ile Gly Glu Leu Asp Ile Asn Thr Asn Val Gly Ile Trp Val Leu
225 230 235 240

Phe Lys Ile Ser Asn Pro Asp Gly Tyr Ala Thr Leu Gly Asn Leu Glu
245 250 255

Val Ile Glu Glu Gly Pro Leu Thr Gly Glu Ala Leu Thr His Ala Lys
260 265 270

```
Gln Lys Glu Lys Lys Trp Lys Gln His Met Glu Lys Lys Arg Leu Glu
        275                 280                 285

Thr Gln Gln Ala Tyr Asp Pro Ala Lys Gln Ala Val Asp Ala Leu Phe
    290                 295                 300

Thr Asn Ala Gln Gly Glu Glu Leu His Tyr His Ile Thr Leu Asp His
305                 310                 315                 320

Ile Gln Asn Ala Asn Gln Leu Val Gln Ser Ile Pro Tyr Val His His
                325                 330                 335

Ala Trp Leu Pro Asp Ala Pro Gly Met Asn Tyr Asp Val Tyr Gln Gly
            340                 345                 350

Leu Asn Ala Arg Ile Met Gln Ala Tyr Asn Leu Tyr Ala Ala Arg Asn
        355                 360                 365

Val Ile Thr Asn Gly Asp Phe Thr Gln Gly Leu Gln Gly Trp His Ala
    370                 375                 380

Thr Gly Lys Ala Thr Val Gln Gln Met Asp Gly Ala Ser Val Leu Val
385                 390                 395                 400

Leu Ser Asn Trp Ser Ala Gly Val Ser Gln Asn Leu His Ala Gln Asp
                405                 410                 415

His His Gly Tyr Val Leu Arg Val Ile Ala Lys Lys Glu Gly Pro Gly
            420                 425                 430

Lys Gly Tyr Val Thr Met Met Asp Cys Asn Gly Asn Gln Glu Thr Leu
        435                 440                 445

Lys Phe Thr Ser Cys Glu Glu Gly Tyr Met Thr Lys Thr Val Glu Ile
    450                 455                 460

Phe Pro Glu Ser Asp Arg Val Arg Ile Glu Ile Gly Glu Thr Glu Gly
465                 470                 475                 480

Thr Phe Tyr Val Asp Ser Ile Glu Leu Leu Cys Met Gln Gly Tyr Ala
                485                 490                 495

Ile Asn Asn Asn Pro His Thr Gly Asn Met Tyr Glu Gln Ser Tyr Asn
            500                 505                 510

Gly Ile Tyr Asn Gln Asn Thr Ser Asp Val Tyr His Gln Gly Tyr Thr
        515                 520                 525

Asn Asn Tyr Asn Gln Asp Ser Ser Ser Met Tyr Asn Gln Asn Tyr Thr
    530                 535                 540

Asn Asn Asp Asp Gln His Ser Asp Cys Thr Cys Asn Gln Gly His Asn
545                 550                 555                 560

Ser Gly Cys Thr Cys Asn Gln Gly Tyr Asn Arg
                565                 570


<210> SEQ ID NO 19
<211> LENGTH: 627
<212> TYPE: PRT
<213> ORGANISM: Bacillus thuringiensis

<400> SEQUENCE: 19

Val Lys Asn Met Asn Ser Tyr Gln Asn Lys Asn Glu Tyr Glu Ile Leu
1               5                   10                  15

Asp Thr Ser Pro Asn Asn Ser Thr Met Ser Thr Leu His Pro Arg Tyr
            20                  25                  30

Pro Leu Ala Lys Asp Pro Tyr Lys Pro Met Arg Asn Thr Asn Tyr Lys
        35                  40                  45

Glu Trp Leu Ala Met Cys Ala Asn Asn Asn Gln Val Pro Ile Asp Pro
    50                  55                  60

Leu Asp Asn Thr Trp Ala Gly Val Met Ala Ala Leu Phe Ala Ser Ala
65                  70                  75                  80
```

```
Ala Ala Ile Ala Gly Leu Met Ser Ala Val Pro Val Phe Ser Val Val
                85                  90                  95

Ala Thr Gly Thr Ala Leu Ala Ala Ala Leu Thr Pro Ile Leu Phe Pro
            100                 105                 110

Ser Asn Gly Pro Asp Val Ser Thr Gln Leu Met Ser Asn Thr Glu Ala
        115                 120                 125

Leu Leu Lys Arg Glu Leu Asp Thr Tyr Val Arg Ala Arg Ala Asp Ser
    130                 135                 140

Glu Phe Gln Ala Leu Glu Ala Gln Arg Glu Phe Phe Lys Ser Ala Phe
145                 150                 155                 160

Asp Tyr Trp Lys Leu Tyr Pro Thr Asn Ser Asn Ala Ile Ala Thr Val
                165                 170                 175

Ala Ala Arg Phe His Thr Val Asn Gly Ala Phe Val Thr Ala Met Arg
            180                 185                 190

Leu Phe Arg Thr Ala Gly Tyr Glu Ala Leu Leu Leu Pro Val Tyr Ala
        195                 200                 205

Gln Ala Ala Arg Leu His Leu Leu His Leu Arg Asp Gly Val Leu Phe
    210                 215                 220

Ala Asn Glu Trp Gly Leu Ala Lys Asp Pro Gly Asp Leu His Asp Gln
225                 230                 235                 240

Glu Phe Asn Lys Tyr Ala Ala Glu Tyr Ala Asp Tyr Cys Glu Ser Thr
                245                 250                 255

Tyr Asn Thr Glu Leu Asn Arg Ile Lys Thr Ala Pro Gly Lys Thr Trp
            260                 265                 270

Leu Asp Tyr Asn Gln Tyr Arg Arg Ile Met Thr Ile Ala Val Leu Asp
        275                 280                 285

Ile Ala Ala Lys Phe Ser Ile Leu Asn Pro Arg Leu Tyr Arg Leu Pro
    290                 295                 300

Leu Gln Glu Glu Ile Leu Thr Arg Lys Ile Tyr Thr Asp Pro Val Asn
305                 310                 315                 320

Phe Ser Pro Gly Pro Ser Ile Ala Asp Asp Glu Asn Arg Tyr Thr Val
                325                 330                 335

Pro Leu Ser Leu Val Thr Gln Leu Val Asn Ser Arg Leu Phe Thr Asn
            340                 345                 350

Val Ala Ser Ala Gln Asn Ala Gly Phe Ile Gly Asn Gln Asn Arg Tyr
        355                 360                 365

Lys Asn Ile Gly Val Gly Asp Pro Val Asp Gly Pro Ile Ile Gly Gln
    370                 375                 380

Ser Val Tyr Glu Lys Val Asp Ala Gly Ile Pro Thr Asn Glu Trp Val
385                 390                 395                 400

Tyr Glu Val Gly Val Asn Gly Ile Gln Asn Asp Tyr Pro Arg Asn Ile
                405                 410                 415

Gly Leu Arg Lys Gly Ser Thr Thr Ala Phe Thr Asp His Leu Ala Gly
            420                 425                 430

Ser Gln Tyr Asn Leu Gly Pro Leu Thr Arg Val Ser Ile Pro Thr Lys
        435                 440                 445

Asp Asn Ala Pro Ile Asn Asn Thr Asn Phe Thr His Arg Leu Ser Asp
    450                 455                 460

Ile Ile Leu Pro Gly Asn Lys Gly Ser Ser Phe Ala Trp Thr His Val
465                 470                 475                 480

Asp Val Asp Pro Thr Gly Asn Tyr Leu Ser Thr Thr Lys Ile Asn Leu
                485                 490                 495

Ile Pro Ala Thr Lys Ala Ser Lys Ile Pro Leu Ser Phe Tyr Leu Arg
```

```
            500                 505                 510

Lys Gly Pro Gly Phe Ile Gly Gly Asp Leu Val Arg Leu Gly Ser Gly
        515                 520                 525

Phe Glu Cys Ser Tyr Lys Phe Asn Phe Lys Ser Pro Gly Ser Ser Ala
    530                 535                 540

Asn Phe Arg Ile Arg Ile Arg Tyr Ala Gly Ala Gly Ser Gly Gln Gly
545                 550                 555                 560

Ala Asp Gly Gln Val Tyr Phe Lys Leu Gly Asn Tyr Thr Ser Pro Thr
                565                 570                 575

Thr Pro Trp Gly His Thr Gly Phe Asp Tyr Gly Asn Val Lys Tyr Asn
            580                 585                 590

Gln Phe Arg Val Leu Glu Leu Phe Gly Thr Ala Glu Asn Ile Thr Asp
        595                 600                 605

Asn Asp Leu Lys Ile Ile Val Trp Thr Gly Ser Ser Ala Gln Asp Phe
    610                 615                 620

Leu Ser Arg
625


<210> SEQ ID NO 20
<211> LENGTH: 566
<212> TYPE: PRT
<213> ORGANISM: Bacillus thuringiensis

<400> SEQUENCE: 20

Val Ser Pro Met Tyr Ile Asn Thr Met Lys Asn Thr Leu Lys Leu Glu
1               5                   10                  15

Thr Thr Asp Tyr Glu Ile Asp Gln Ala Ala Ile Ser Ile Glu Cys Met
            20                  25                  30

Ser Asn Glu Gln Asn Pro Gln Glu Lys Met Ile Leu Trp Asp Glu Val
        35                  40                  45

Lys Gln Ala Lys Gln Leu Ser Gln Ser Arg Asn Leu Leu Tyr Asn Gly
    50                  55                  60

Asp Phe Glu Asp Ala Ser Asn Gly Trp Lys Thr Ser Tyr Thr Ile Glu
65                  70                  75                  80

Ile Gly Lys Tyr Ser Ser Ile Phe Lys Gly Gln Tyr Leu His Met Phe
                85                  90                  95

Gly Ala Arg Asp Val Leu Gly Glu Val Phe Pro Thr Tyr Val Tyr Gln
            100                 105                 110

Lys Ile Asp Glu Ser Lys Leu Lys Pro Tyr Thr Arg Tyr Arg Val Arg
        115                 120                 125

Gly Phe Val Gly Ser Ser Lys Asp Leu Lys Leu Val Val Thr Arg Tyr
    130                 135                 140

Gly Lys Glu Ile Asp Ala Ile Met Asp Val Pro Asp Asp Leu Ala Tyr
145                 150                 155                 160

Met Gln Pro Thr Pro Ser Cys Gly Asp Tyr Arg Cys Glu Ser Ala Ser
                165                 170                 175

Gln Tyr Val Ser Gln Gly Tyr Pro Thr Pro Tyr Gly Asp Gly Tyr Ala
            180                 185                 190

Ser Asp Arg Tyr Ala Cys Pro Ser Asp Arg Val Lys Lys His Val Lys
        195                 200                 205

Cys His Asn Arg His Pro Phe Asp Phe His Ile Asp Thr Gly Glu Leu
    210                 215                 220

Asp Ile Asn Thr Asn Val Gly Ile Trp Val Leu Phe Lys Ile Ser Asn
225                 230                 235                 240

Pro Asp Gly Tyr Ala Thr Leu Gly Asn Leu Glu Val Ile Glu Glu Gly
```

```
                245                 250                 255

Pro Ile Thr Gly Glu Ala Leu Thr His Ala Lys Gln Lys Glu Lys Lys
            260                 265                 270

Trp Asn Gln His Met Glu Lys Ala Gln Ile Glu Thr Gln Gln Ala Tyr
        275                 280                 285

Asp Pro Ala Lys Gln Ala Val Asp Ala Leu Phe Thr Asn Ala Gln Gly
    290                 295                 300

Glu Glu Leu His Tyr His Ile Thr Leu Asp His Ile Gln Asn Ala Asn
305                 310                 315                 320

Gln Leu Val Gln Ser Ile Pro Tyr Val His His Ala Trp Leu Pro Asp
                325                 330                 335

Ala Pro Gly Met Asn Tyr Asp Val Tyr Gln Glu Leu Asn Ala Arg Ile
            340                 345                 350

Met Gln Ala Arg Tyr Leu His Asp Ala Arg Asn Val Ile Thr Asn Gly
        355                 360                 365

Asp Phe Thr Gln Gly Leu Gln Gly Trp His Ala Thr Gly Lys Ala Thr
    370                 375                 380

Val Gln Gln Met Asp Gly Ala Ser Val Leu Val Leu Ser Asn Trp Ser
385                 390                 395                 400

Ala Gly Val Ser Gln Asn Leu His Ala Gln Asp His His Gly Tyr Val
                405                 410                 415

Leu Arg Val Ile Ala Lys Lys Glu Gly Pro Gly Lys Gly Tyr Val Thr
            420                 425                 430

Met Met Asp Cys Asn Gly Asn Gln Glu Thr Leu Lys Phe Thr Ser Cys
        435                 440                 445

Glu Glu Gly Tyr Met Thr Lys Thr Val Glu Ile Phe Pro Glu Ser Asp
    450                 455                 460

Arg Val Arg Ile Glu Ile Gly Glu Thr Glu Gly Thr Phe Tyr Val Asp
465                 470                 475                 480

Ser Ile Glu Leu Leu Cys Met Gln Gly Tyr Ala Ile Asn Asn Asn Pro
                485                 490                 495

His Thr Gly Asn Met Tyr Glu Gln Ser Tyr Asn Gly Ile Tyr Asn Gln
            500                 505                 510

Asn Thr Ser Asp Val Tyr His Gln Gly Tyr Thr Asn Asn Tyr Asn Gln
        515                 520                 525

Asp Ser Ser Ser Met Tyr Asn Gln Asn Tyr Thr Asn Asn Asp Asp Gln
    530                 535                 540

His Ser Asp Cys Thr Cys Asn Gln Gly His Asn Ser Gly Cys Thr Cys
545                 550                 555                 560

Asn Gln Gly Tyr Asn Arg
                565


<210> SEQ ID NO 21
<211> LENGTH: 296
<212> TYPE: PRT
<213> ORGANISM: Bacillus thuringiensis

<400> SEQUENCE: 21

Met Lys Lys Leu Met Phe Ser Leu Val Ala Thr Thr Met Ser Met Gly
1               5                   10                  15

Leu Ile Leu Gly Ser Ala Pro Val Lys Ala Asp Val Ser Asn Lys Asn
            20                  25                  30

Ser Ala Tyr Gln Asp Ile Asp Glu Arg Val Lys Lys Met Ala Gln Ser
        35                  40                  45

Ala Ala Trp Gly Gly Gln Glu Tyr Arg Asn His Asn Ile Lys Asp Ile
```

```
    50                  55                  60

Glu Leu Lys Gly Asn Leu Ile Asp Gly Ser Met Ile Glu Asn Ser Glu
65                  70                  75                  80

Val Leu Thr Val Ser Ser Asp Ile Leu Glu Asn Lys Leu Gly His Thr
                85                  90                  95

Val Asn Met Pro Ser Thr Gly Tyr Glu His Glu Phe Glu Glu Thr Thr
            100                 105                 110

Asn Thr Thr Asn Thr Ser Gly Trp Thr Phe Gly Tyr Asn Tyr Asn Ala
        115                 120                 125

Ser Phe Ser Val Leu Met Val Ser Ala Ser Gln Ser Phe Ser Val Glu
    130                 135                 140

Tyr Asn Met Ser Thr Ser Asn Thr His Glu Lys Lys Glu Lys Arg Lys
145                 150                 155                 160

Phe Thr Val Pro Ser Ile Glu Val Pro Val Pro Ala Gly Lys Lys Tyr
                165                 170                 175

Lys Val Glu Tyr Val Phe Glu Lys Val Lys Val Ser Gly Lys Asn Lys
            180                 185                 190

Ile Asp Ala Asn Leu Tyr Gly Asp Val Thr Tyr Tyr Tyr Asn Asn Gln
        195                 200                 205

Pro Met Ser Pro Gln Leu Leu Tyr Ser Val Gln Gly Leu Ala Ala Asp
    210                 215                 220

Lys Gln Gly Phe Glu Gln Val Ile Arg Asp Ser Ala Val Gly Asn Asp
225                 230                 235                 240

Arg Phe Gly Ile Lys Thr Thr Gly Ile Gly Gln Phe Ser Thr Glu Phe
                245                 250                 255

Gly Thr Arg Leu Thr Arg Thr Leu Thr Asp Ile Thr Asp Thr Arg Asn
            260                 265                 270

Pro Val Lys Val Glu Thr Lys Asn Val Pro Val Glu Phe Lys Thr Leu
        275                 280                 285

Ser Ile Asp Thr Arg Val Ile Lys
    290                 295


<210> SEQ ID NO 22
<211> LENGTH: 308
<212> TYPE: PRT
<213> ORGANISM: Bacillus thuringiensis

<400> SEQUENCE: 22

Met Lys Lys Asn Arg Met Leu Leu Lys Trp Met Cys Gly Leu Thr Ile
1               5                   10                  15

Gly Ile Gly Ser Leu Thr Gly Gly Ser Leu Asn Ala Phe Ala Asp Glu
            20                  25                  30

Val Ser Asp Ser Leu Ala Asp Val Gly Phe Leu Tyr Gly Asp Tyr Leu
        35                  40                  45

Tyr Lys Thr Lys Gln His Pro Gln Gly Thr Leu Pro Ile Thr Tyr Pro
    50                  55                  60

Met Arg Glu Ile Asn Asn Tyr Gln Ile Ile Asp Lys Ser Val Ser Gln
65                  70                  75                  80

Val Gly Ser Thr Glu Tyr Glu Glu Gly Gln Thr Leu Tyr Val Asp Asp
                85                  90                  95

Asp Val Phe Asp Asn Lys Thr Gly Thr Asp Gln Thr Phe Lys Thr Ile
            100                 105                 110

Gln Phe Glu Lys Glu Phe Ser Glu Thr Ala Thr Ser Ser Thr Thr His
        115                 120                 125

Ser Val Gly Thr Ser Leu Glu Glu Ser Val Lys Phe Asp Phe Phe Val
```

```
    130                 135                 140

Gly Glu Gly Ser Ala Lys Phe Thr Val Asn Tyr Asn Phe Ser Lys Thr
145                 150                 155                 160

Gly Ser Leu Ser Thr Ser Asn Lys Ile Lys Tyr Thr Leu Pro Ser Gln
                165                 170                 175

Ser Ile Asn Val Pro Ala Asn Lys Lys Tyr Glu Val Ile Cys Val Leu
            180                 185                 190

Glu Thr Lys Lys Ala Lys Ala Asn Val Gln Phe Asn Val Asp Val Leu
        195                 200                 205

Gly Asn Ala Lys Tyr Val Tyr Ser Asn Asn Ser Pro Tyr Thr Pro Lys
    210                 215                 220

Tyr Glu Ser Gly Ala Thr Met Leu Lys Thr Leu Asn Glu Lys Asn Pro
225                 230                 235                 240

Thr Pro Ser Val Ser Trp Leu Gly Lys Glu Trp Glu Lys Trp Glu Tyr
                245                 250                 255

His Asp Gly Lys Ala Arg Tyr Lys Asn Gly Ser Gly Thr Val Ser Ala
            260                 265                 270

Glu Tyr Gly Thr Arg Met Val Leu Val Ile Asn Asp Ile Thr Asn Asn
        275                 280                 285

Lys Thr Arg Gly Ser Lys Glu Ile Ala Arg Ile Pro Val Thr Pro Ile
    290                 295                 300

Gln Lys Gln Met
305


<210> SEQ ID NO 23
<211> LENGTH: 1244
<212> TYPE: PRT
<213> ORGANISM: Bacillus thuringiensis

<400> SEQUENCE: 23

Met Asn Gly Gly Glu Asn Met Asn Gln Asn Asn Gln Asn Glu Met Gln
1               5                   10                  15

Ile Ile Asp Ser Ser Ser Asn Asp Phe Ser Gln Ser Asn Arg Tyr Pro
            20                  25                  30

Arg Tyr Pro Leu Ala Lys Glu Ser Asn Tyr Lys Asp Trp Leu Ala Ser
        35                  40                  45

Cys Asp Glu Ser Asn Val Asp Thr Leu Ser Ala Thr Ser Asn Val Arg
    50                  55                  60

Ala Ser Val Ser Arg Ala Leu Gly Ile Val Asn Gln Ile Leu Gly Phe
65                  70                  75                  80

Leu Gly Leu Gly Phe Ile Gly Thr Gly Leu Gly Val Leu Ser Asp Leu
                85                  90                  95

Phe Asn Ser Phe Trp Pro Ser Asn Asp Asn Ser Ile Trp Glu Ser Phe
            100                 105                 110

Leu Arg Ser Val Glu Glu Leu Ile Asp Arg Arg Val Arg Glu Val Glu
        115                 120                 125

Arg Phe Arg Ile Glu Ser Gln Phe Thr Gly Leu Arg Asn Val Met Ser
    130                 135                 140

Asn Tyr Asn Gly Ala Leu Arg Asp Trp Asn Gly Asn Arg Asn Asn Leu
145                 150                 155                 160

Ala Leu Gln Ser Glu Val Arg Ser Arg Phe Asp Asn Ser Asp Asp Ala
                165                 170                 175

Phe Ala Ser Arg Met Pro Glu Phe Arg Ile Glu Gly Phe Glu Ile Gln
            180                 185                 190

Ser Leu Ala Val Tyr Ala Gln Ala Ala Thr Leu His Leu Leu Leu Leu
```

-continued

```
        195                 200                 205

Arg Asp Gly Val Val Asn Gly Leu Gln Trp Gly Phe Asp Ile Val Thr
    210                 215                 220

Val Asn Arg Leu Tyr Glu Lys Leu Val Cys Leu Ser Gly Ala Tyr Ala
225                 230                 235                 240

Asp His Cys Thr Leu Phe Tyr Arg Gln Gly Leu Glu Glu Leu Arg Asn
                245                 250                 255

Arg Gly Asn Trp Asn Ala Phe Asn Asn Tyr Arg Arg Asp Met Thr Leu
            260                 265                 270

Gln Val Leu Asp Val Ile Ser Leu Phe Pro Asn Tyr Asp Pro Arg Leu
        275                 280                 285

Tyr Asp Ile Asn Thr Asn Thr Gln Leu Thr Arg Glu Ile Tyr Thr Glu
    290                 295                 300

Pro Leu Ala Ile Pro Gly Trp Leu Asn Ser His Ser Asn Pro Thr Gln
305                 310                 315                 320

Phe Gln Gln Ile Glu Asn Asp Leu Ile Arg Ser Pro Ser Val Phe Ser
                325                 330                 335

Asn Leu Glu Thr Leu Phe Met Glu Ala Gly Phe Ala Phe Phe Gln Ala
            340                 345                 350

Gly Ile Ala Arg Gln Ala Val Leu Arg Thr Arg Thr Ser Ser Leu Asn
        355                 360                 365

Met Asn Arg Thr Ala Val Ile Val Thr Pro Trp Gln Gly Ala Pro His
    370                 375                 380

Pro Asn Val Ser His Glu Leu Gln Val Thr Leu Gln Asp Arg Asn Val
385                 390                 395                 400

Phe Asn Ile Asn Ser Val Val Gly Arg Glu Ile Ser Ser Gln Thr Gly
                405                 410                 415

Leu Leu Phe Gly Val Gln Gln Ala Thr Phe His Phe Val Trp Ala Gly
            420                 425                 430

Gly Asn Ala Ala Thr Thr Thr Gln Phe Asn Leu Pro Pro Ile Ser Gly
        435                 440                 445

His Ser Thr Ser Ile Thr Ser Asn Ile Pro Gly Thr Asn Ser Thr Thr
    450                 455                 460

Pro Thr Gly Ser Asp Tyr Thr His Arg Leu Ser Ser Ile Thr Ser Thr
465                 470                 475                 480

Ser Val Gly Thr Trp Gln Arg Asp Arg Thr Asn Ile Met Ala Tyr Gly
                485                 490                 495

Trp Thr His Val Ser Ala Glu Arg Thr Asn Arg Ile Ile Pro Asn Arg
            500                 505                 510

Ile Thr Gln Ile Pro Ala Val Lys Gly Ser Leu Phe Ser Asp Asn Pro
        515                 520                 525

Pro Asn Thr Ser Arg Thr Arg Val Glu Asn Gly Pro Gly His Thr Gly
    530                 535                 540

Gly Gly Leu Val Val Met Asp Gly Gly Thr Ser Val Leu Gln Met Arg
545                 550                 555                 560

Val Thr Ser Ser Ala Arg Gln Arg Tyr Asp Met Arg Leu Arg Tyr Val
                565                 570                 575

Ala Leu Ala Pro Ala Thr Val Glu Val Arg Ile Pro Glu Leu Gly Gly
            580                 585                 590

His Val Arg Phe Gln Met Pro Met Thr Ala Thr Gly Leu Pro Ala Pro
        595                 600                 605

Leu Pro Tyr Ser His Leu Arg Tyr Val Asp Ile Pro Leu Arg Phe Glu
    610                 615                 620
```

-continued

```
Thr Pro His Gly Glu Asn Thr Trp Thr Phe Glu Leu Gln Thr Thr Phe
625                 630                 635                 640

Ala Ala Val Ala Ile Asp Arg Val Glu Phe Ile Pro Val Asn Ala Thr
                645                 650                 655

Ala Leu Glu Tyr Glu Gly Lys Arg His Leu Glu Lys Ala Lys Lys Ala
            660                 665                 670

Val Gly Asp Leu Phe Ile Asn Asn Gly Lys Glu Ala Leu Lys Val Asp
        675                 680                 685

Thr Thr Asp Tyr Asp Val Asp Gln Ala Ala Asn Leu Val Glu Cys Met
    690                 695                 700

Pro Glu Glu Leu Tyr Thr Lys Glu Lys Met Ile Leu Leu Asp Glu Val
705                 710                 715                 720

Lys His Ala Lys Arg Phe Ser Gln Ser Arg Asn Leu Ile Gln Asn Gly
                725                 730                 735

Asp Phe Glu Phe Ala Thr Asp Gly Trp Met Thr Ser Ser Asn Val Ile
            740                 745                 750

Val Gln Ala Asp Asn Thr Val Phe Lys Gly Lys Tyr Leu Asn Met Pro
        755                 760                 765

Gly Ala Ile Glu Thr Asp Thr Ser Thr Phe Pro Thr Tyr Ile Tyr Gln
    770                 775                 780

Lys Ile Asp Glu Ser Arg Leu Lys Pro Tyr Thr Arg Tyr Lys Val Arg
785                 790                 795                 800

Gly Phe Val Gly Ser Ser His Asp Val Arg Leu Ile Val Glu Arg Asn
                805                 810                 815

Gly Lys Glu Val Asp Ala Leu Leu Asn Val Arg Asn Asp Leu Ser Leu
            820                 825                 830

Asp Thr Val Ala Pro Ser Cys Ile Glu Ala Asn Gln Pro Tyr Pro Ile
        835                 840                 845

Ile His Asp Gly Cys Leu Thr Asn Val Ile Asp Thr Asn Ser Tyr Glu
    850                 855                 860

Glu Ala Gln Ser Gly His Ala Asn Cys Lys Lys Glu His Gly Met Cys
865                 870                 875                 880

His Gln Ser His Gln Phe Asp Phe His Ile Asp Thr Gly Glu Ile His
                885                 890                 895

Thr Asn Lys Asn Pro Gly Ile Trp Val Leu Phe Lys Ile Ser Ser Pro
            900                 905                 910

Glu Gly His Ala Thr Leu Asp Asn Ile Glu Leu Ile Glu Asp Gly Pro
        915                 920                 925

Leu Val Gly Glu Ser Leu Ala Phe Val Lys Lys Gln Glu Lys Lys Trp
    930                 935                 940

Glu Asn Glu Met Glu Thr Arg Trp Leu Gln Thr Lys Glu Val Tyr Glu
945                 950                 955                 960

Lys Ala Lys Gly Glu Ile Asp Ser Leu Phe Thr Asp Ala Gln Asp Gln
                965                 970                 975

Ala Leu Lys Phe Asp Thr Asn Ile Ser His Ile Ile Ser Ala Glu His
            980                 985                 990

Leu Val Gln Ser Met Pro Tyr Val Tyr Asn Asn Trp Leu Ser Asp Val
        995                 1000                1005

Pro Gly Met Asn Tyr Asp Ile Tyr Thr Glu Leu Glu Arg Arg Ile Thr
    1010                1015                1020

Gln Ala Tyr Ser Leu Tyr Glu His Arg Asn Ile Ile Lys Asn Gly Asp
1025                1030                1035                1040

Phe Asp Tyr Gly Leu Asn His Trp His Ala Thr Pro His Ala Lys Val
                1045                1050                1055
```

Gln Gln Ile Asp Gly Thr Ala Val Leu Val Leu Pro Asn Trp Ser Ser
            1060                1065                1070

Asn Val Ser Gln Asn Leu Cys Val Glu His Asn Arg Gly Tyr Ile Leu
        1075                1080                1085

Arg Val Thr Ala Lys Lys Glu Asp Met Gly Lys Gly Tyr Val Thr Ile
        1090                1095                1100

Ser Asp Cys Asn Gly Asn Gln Glu Thr Leu Thr Phe Thr Ser Cys Ala
1105                1110                1115                1120

Asn Tyr Val Ala Asn Glu Ile Thr Asn Asp Gln Ser Glu Tyr His Phe
            1125                1130                1135

Ser Gln Glu Met Asn Glu Gln Arg Gly Tyr Asn Pro Asn Glu Thr Ile
        1140                1145                1150

Asn Lys Gln Leu Asp Tyr Ser Leu Asp Gln Val Arg Asn Glu Gln Arg
        1155                1160                1165

Cys Tyr Asn Pro Asn Glu Ile Thr Asn Asp Gln Ser Glu Tyr His Tyr
    1170                1175                1180

Ser Gln Glu Met Asn Glu Gln Arg Cys Tyr Asn Pro Asn Glu Ile Ile
1185                1190                1195                1200

Asn Glu His Arg Asn Tyr Val Thr Arg Thr Ile Asp Phe Phe Pro Asp
            1205                1210                1215

Thr Asn Gln Val Arg Ile Asp Ile Gly Glu Thr Glu Gly Thr Phe Lys
        1220                1225                1230

Val Glu Ser Ile Glu Leu Ile Cys Met Lys Ser Gln
        1235                1240

<210> SEQ ID NO 24
<211> LENGTH: 521
<212> TYPE: PRT
<213> ORGANISM: Bacillus thuringiensis

<400> SEQUENCE: 24

Met Thr Lys Ser Glu Phe Ile Gln Asn Ser Cys Arg Lys Met Gln Ser
1               5                   10                  15

Lys Val Arg Val Ile Ile Leu Ser Thr Asn Asp Pro Val Val Asn Asn
            20                  25                  30

Asn Thr Leu Asp Ile Thr Glu Ile Lys Asp Leu Ala His Leu Ser Gln
        35                  40                  45

Ala Ile Met Leu Ala Asn Asn Phe Gln Ala Ala Leu Val Pro Thr Ser
    50                  55                  60

Ser Glu Phe Gly Gln Asp Val Leu Arg Phe Asp Val Asn Gln Gly Ile
65                  70                  75                  80

Ser Ile Ala Asn Asn Ile Tyr Pro Lys Ala Val Asp Ile Asn Tyr Ile
            85                  90                  95

Ser Arg Thr Leu Ser Gln Ser Asn Asn Gln Val Asn Ser Met Ile Asn
        100                 105                 110

Met Val Val Asn Glu Leu Lys Leu Leu Leu Gly Ile Asn Leu Ala Asp
    115                 120                 125

Ser Val Leu Gln Gln Leu Thr Ser Leu Val Ala Tyr Thr Phe Thr Asn
    130                 135                 140

Leu Tyr Thr Gln Gln Asn Ser Ala Trp Val Phe Trp Gly Lys Gln Ala
145                 150                 155                 160

Ser Asn Gln Thr Asn Tyr Thr Tyr Asn Ile Val Phe Ala Ile Gln Asn
            165                 170                 175

Ala Gln Thr Gly Asn Phe Met Lys Ala Ile Pro Met Gly Phe Glu Ile
        180                 185                 190

```
Ser Ala Tyr Ala Val Lys Glu Gln Val Leu Phe Phe Thr Ile Gln Asp
        195                 200                 205

Tyr Ala Ser Tyr Ser Val Lys Ile Gln Ala Ile Asn Val Thr Gln Pro
    210                 215                 220

Leu Ile Asn Ser Ser Tyr Gly Ser Leu Ser Gly Val Tyr Asn Ile Ile
225                 230                 235                 240

Thr Ala Leu Asn Asn Ile Ser Val Ile Thr Met Ser Asn Ser Asp Glu
                245                 250                 255

Asn Val Asn Leu Trp Tyr Asp Asn Asp Asp Leu Asn Gln Lys Trp Ile
            260                 265                 270

Leu Glu Phe Asn His Asn His Tyr Ala Tyr Ile Ile Arg Asn Leu Ser
        275                 280                 285

Asn Arg Ser Leu Val Leu Thr Trp Asp Ser Thr Ser Gly Ser Asn Asn
    290                 295                 300

Val Phe Ala Thr Asn Tyr Gln Gly Asn Asp Glu Gln Phe Trp Ile Ile
305                 310                 315                 320

Gln Asp Thr Asp Asn Asp Tyr Phe Tyr Leu Ser Asn Met Arg Asp Thr
                325                 330                 335

Gln Tyr Val Leu Glu Ile Ala Gly Ser Val Phe Tyr Asn Gly Thr Asn
            340                 345                 350

Val Ile Val Asn Lys Lys Thr Ser Ser Leu Asn Gln Lys Phe Ser Ile
        355                 360                 365

Asn Arg Ile Asn Arg Gln Ile Gln Asn Gly Ile Tyr Asn Ile Thr Thr
    370                 375                 380

Tyr Leu Asn Ala Ser Ser Val Ile Thr Met Ser Thr Asp Tyr Asn Ile
385                 390                 395                 400

Asn Val His Asp Tyr Pro Val Asn Leu Trp Phe Lys Asn Asp Ser Ile
                405                 410                 415

Asn Gln Lys Trp Ile Phe Glu Phe Asp Ser Asp Lys Ser Ala Tyr Arg
            420                 425                 430

Val Arg Ser Val Ser Asn Pro Ser Leu Phe Leu Ser Trp Pro Val Ala
        435                 440                 445

Ser Phe Thr Asn Arg Ala Ala Val Thr Pro Asn Pro Arg Asp Asn Glu
    450                 455                 460

Tyr Phe Trp Phe Leu Gln Ser Ala Gly Leu Gly Thr Phe Tyr Leu Val
465                 470                 475                 480

Ser Met Arg Asp Thr Arg Tyr Val Leu Glu Val Glu Asn Ser Asn Ile
                485                 490                 495

Asp Asn Gly Thr Asn Ile Ile Val Asn Gln Arg Thr Gly Asn Phe Asn
            500                 505                 510

Gln Arg Phe Tyr Ile Glu Asn Ile Asn
        515                 520
```

<210> SEQ ID NO 25
<211> LENGTH: 1992
<212> TYPE: DNA
<213> ORGANISM: Artificial Sequence
<220> FEATURE:
<223> OTHER INFORMATION: synthetic nucleotide sequence encoding a toxin protein

<400> SEQUENCE: 25

```
atgcacatca tcgacagcag cagcaatgat ttctcccaaa gcaacagata tccaagatat     60

cctctggcca aggagagcaa ctacaaggac tggctggcaa gctgtgatga aagcaacctg    120

gaccgcctct ccacgccttc ttcagttcaa gatgctgtgg tgacaagcct caacatcttc    180
```

```
agctacatct tcggcttcct tgatgctggc gccacctccg ccggcctcgg catcctcggc    240

gtcctcttcg gccagttctg gccatcaaac aacaatgctg tttgggaaac cttcttgagg    300

agcgtggagg agctgattgc aagggagatc gacatcgtgg agaggaacag gatcatggcg    360

cagtttgatg gcctcagaaa tgtgatgagc aactacaatg gagctctcat cgactgggat    420

ggcaacaggg acaacaccgc gctgcaatca gaggtgagga gcagatttga caatgctgat    480

gatgccttcg ccttgaggat tccagagttc agaatcaagg attttgagat ccagagcctc    540

gccgtctatg ctcaagctgc caccctccac ctgctgctgc tgagagatgc tgtggtgaat    600

ggccagctat ggggagttga tcctgtcacc acccaaagaa gatatgagaa gctggtctgc    660

ctctccggcg cctatgctga tcactgcacc ttcttctaca ggcaagggct ggaggagctg    720

agaggaaaag gaaactggac ggccttcaac aactacagga ggaacatgaa catccaggtg    780

ctggatgtca tctccctctt ctcaaactat gatccaaggc tctatggcaa caacaccaac    840

acccagctga caagggagat cttcaccgag ccgctggcga cgccaggatg gctggacaga    900

tacagcaacc cagatcagtt ccagcagatc gagtacaacc tcaacccttc tccaagcctc    960

tcctcaaccc tcctcaacct tgctgctgac accggcctcg gctactacgg cgccggcgcc   1020

gtcacgccgc gccccatcat ccagaggacc tccatgagga ggctcaacac cggcgccacc   1080

gtgcccttca ccaccgcctg gcaaggagct ccaaatcctc tcatcagcca gcagaagcag   1140

ctctcctttg aaggatttga tgttttcaac atcaacagcg tggtgtcaag agaagtttct   1200

tctcaaacaa gcagcctctt cggcgtccag caagctgtgt tccacaccgt cattgctgga   1260

ggaaacatcc ctccaacaat gaagatcatt gatctccagc caagaggaaa ctacagcacc   1320

tccgtcacca gcaacatccc tggaaaaaga agcgccaccg ccaccgcctc agattacacc   1380

caccgcctga gcagcatcac ctccacctcc gtcggcaccg cctaccgtga caggaccaac   1440

atcatggcat atggatggac ccatgtttct tcagaaaaaa caaacaggat tcttccaaac   1500

aggatcaccc agatcccctt cgtcaagggc atcatcacca gcagcggcac ccatgtgagg   1560

agcggccctg atcacactgg aggaagcctg gtgagcatgg gaggagatgc tcaatttggc   1620

atggtggtga caagctccgc gcgccaaaga tacagggtga ggctgagata tgctgcttca   1680

aattctgttg atttccgcct gaggatctcg ccgctcggcg tggactacaa cttcaccctt   1740

cctggaggag gcaccagctt caacccagat ctccgctaca gcagcttcag atacatcacc   1800

ctccccatcg agtttgaaac accaaattca ttgctgaact tctccttcga cctggacacc   1860

ctcaccttga tgaatggcac ctgcttcttc gacagggtgg agttcctccc cgtcaacagc   1920

attgctctgg aatatgaagg aaagcagaag ctggagaagg ccaagcaagc tgtggacaac   1980

ctcttcacca ac                                                       1992
```

<210> SEQ ID NO 26
<211> LENGTH: 1992
<212> TYPE: DNA
<213> ORGANISM: Artificial Sequence
<220> FEATURE:
<223> OTHER INFORMATION: synthetic nucleotide sequence encoding a toxin protein

<400> SEQUENCE: 26

```
atgcacatca tcgacagcag cagcaatgat ttctctcaaa gcaacagata tccaagatat     60

cctctggcca aggagagcaa ctacaaggat tggctggcaa gctgtgatga aagcaacctg    120

gataggctct ccactccttc ttcagttcaa gatgctgtgg tgacaagcct caacatcttc    180
```

```
agctacatct ttggcttcct tgatgctgga gcaacctccg ccggccttgg catcctcggc    240

gtcctctttg gccagttctg gccatcaaac aacaatgctg tttgggaaac cttcttgagg    300

agcgtggagg agctgattgc aagagagatt gacattgtgg agaggaacag gatcatggct    360

caatttgatg gcttgagaaa tgtgatgagc aactacaatg gagctctcat tgattgggat    420

ggaaacagag acaacaccgc gctgcaatca gaagtgagaa gcagatttga caatgctgat    480

gatgcctttg ctctgaggat tccagagttc agaatcaagg attttgagat ccaaagcctc    540

gccgtctatg ctcaagctgc aaccctccat ctgctgctgc tgagagatgc tgttgtcaat    600

ggccagctat ggggagttga tcctgtcacc acccaaagaa gatatgagaa gctggtttgc    660

ttgagcggcg cctatgctga tcattgcacc ttcttctaca ggcaagggct ggaggagctg    720

agaggaaaag gaaactggac ggccttcaac aactacagaa gaaacatgaa catccaggtg    780

ctggatgtca tctccctctt ctcaaattat gatccaaggc tctatggaaa caacaccaac    840

acccagctga caagagagat cttcacagag ccgctggcaa caccaggatg gctggacaga    900

tacagcaatc cagatcagtt ccagcagatt gaatacaacc tcaatccttc tccttctctc    960

tcttcaacat tgctcaacct tgctgctgac actggccttg gctactatgg cgccggcgcc   1020

gtcacgccgc gccccatcat ccaaagaaca agcatgagaa ggctcaacac cggcgccact   1080

gttcccttca ccaccgcctg gcaaggagct ccaaatcctc tcatcagcca gcagaagcag   1140

ctctcctttg aaggatttga tgttttcaac atcaacagcg tggtttcaag agaagtttct   1200

tctcaaacaa gcagcttgtt cggcgtccag caagctgttt tccacaccgt cattgctgga   1260

ggaaacattc ctccaacaat gaagatcatt gatcttcaac caagaggaaa ctacagcacc   1320

tccgtcacca gcaacattcc tggaaaaaga agcgccaccg ccactgcttc agattacacc   1380

caccgcctga gcagcatcac ctccacctct gttggcaccg cctaccgtga cagaacaaac   1440

atcatggcat atggatggac acatgtttct tcagaaaaaa caaacaggat tcttccaaac   1500

aggatcaccc agatcccctt cgtcaagggc atcatcacca gcagcggcac ccatgtcaga   1560

agcggccctg atcacactgg aggaagcctg gtgagcatgg gaggagatgc tcaatttgga   1620

atggtggtga caagctccgc gcgccaaaga tacagggtga ggctgagata tgctgcttca   1680

aattctgttg atttcagatt gaggatctcg ccgctgggag tggactacaa cttcaccctt   1740

cctggaggag gaaccagctt caatccagat ctccgctaca gcagcttcag atacatcacc   1800

ctccccattg aatttgaaac accaaattca ttgctgaact tctcctttga tctggacacc   1860

ttgaccttga tgaatggaac ctgcttcttc gacagggtgg agttccttcc tgtcaacagc   1920

attgctctgg aatatgaagg aaagcagaag ctggagaagg ccaagcaagc tgtggacaac   1980

ctcttcacca ac                                                       1992
```

<210> SEQ ID NO 27
<211> LENGTH: 2427
<212> TYPE: DNA
<213> ORGANISM: Artificial Sequence
<220> FEATURE:
<223> OTHER INFORMATION: synthetic nucleotide sequence encoding a toxin protein

<400> SEQUENCE: 27

```
atgaacagct accagaacag aaatgaatat gagatcctgg atgcttctcc aaaccatggc     60

aacatctcaa acagatatcc cttcgccaag aacccaaatg ccatggagaa tgtcaactac    120

aagaactggc tgaatgttag agaagatgtt gctccttcct tcttcggcgg cgcgctgggc    180

atcatcgtca acctcttcaa gcaatatgtc agcttcatca aggctccttc agtttctggc    240
```

```
ggcgtcggct tcttgaggac catcatcggc ctgatgacaa acagaaatgt catcaacctc    300
accattgatg atgttcaaag gctcatcaac cagagcttgg acaacatcac cagagatgct    360
gccaacacca agttcacctc aatccagaac aactacaacc agtacctcct caacaggcag    420
aactacagga acaggagctt gccaaggaac atcttcgtcc agagcctcca gaacattgaa    480
agggagctga gatcagctct ggacagcacc ttctccctcc agaacaggga gctgctgctg    540
ctgccaaact tcacccagat cgccatgctt catctcaccg tgctgagaga tgctgtcatc    600
ttccaaggaa atgatctcat cgtccccacc atctcagaag gccccatcaa cccgctgctg    660
acaaggccgc caagcaacac ctttgaagaa gctctcctca cctccatcag gatctacagc    720
aactactgcg tccgccaata tgaagttggc ctcaacctgc tgaggaacag aggaaacacc    780
tcaaggaact ggctggactt caatgcctac aggctggaga tgaccttcaa ggtgctggac    840
ttcgtcaccc tcttctccct cttcgacacc gtcaagtacc ccgtcagcat tgtttcagaa    900
acagattctg acagcacctc gccggtggtg taccagctca gcagggtgat ctacacagat    960
cctgttggcg ccatcagatc tgatggaaga ggatggtttg atcctcctgt tggaacagat   1020
cgcgtcacct tcaccagcat tgaaaatgag atccctgctc caacaacaag ccgccacctc   1080
tcagagctca ccatctcctc tgggccgctg ggcttcggcg tcaacccagc aagaactcac   1140
agctggcaag gaaacagaaa tgtgaacatc tcagctccaa ctgatgtctc cggcgccatc   1200
agcaacagga caaggaccat cccagcaagg aacatcttca gagtgaacag cagggtgtac   1260
accttggact ggaggctcta cggcgtctac agagcagagt tcttccaagg agctcacagc   1320
caggtgttct cagaaaatcc tccaactggc attggagctc aaagcgccaa caacttcaga   1380
tttcttcctg gagaaaattc tgaaacgccg acgccgcagg actacaccca tgtgctgagc   1440
agggtggtga atgccaccgt cggcctcacg ccggccaccg gcaaccagag gaacagcgtg   1500
ctgatctttg gatggaccca caagagcttg acatcagaga acatctacag gatcaatgag   1560
atcaccaagg tggccgccgt caacacaaga ggaaacagcg gcatcagggt gatctcagga   1620
cctggcttca ctggaggaga tctggtgagg ctggacccta atggcagcgt cagctacaac   1680
ttcacgccgg ccaaccagca ggcgctgcaa agcaacatca ggatcaggct gagatatgct   1740
tgccaaggaa cagcttcctt gaggatcacc tttggaaatg cttcaagcca ggtgatctcc   1800
ttgatctcca ccaccagcag catcaacaac cttcaatatg agaacttcca tgtggtgaat   1860
gttccaaaca acatcaactt ccagagcgtc ggcacccaga tcaccatcca gaacatcagc   1920
caaaatccaa acatcagctt ggacagcatt gagctcttct caaacatccc catccctcaa   1980
gaacctccct tcaacccggt ggtgccggag ccgcccatca tctcaggaaa ctaccagatt   2040
gtgacgccgc tggacagaag aagcatcatc gacctcaacc ccaacaacaa tgtcaccctc   2100
tggaccaaca acagaagcag caaccagatc tggaacttca gctatgatca gcagcgcggc   2160
gcctacctca tcaggagctt gaggacagga agcctggtgc tctccatgga ttcaccaagg   2220
acaagcaatg tttttggata tccaagcaac tctgatgctt ctcagttctg gatcttggag   2280
ccaaatcaag atggcttcat cttcagatcc ttgagggaca ggaacctggt gctggatgtt   2340
tctggaggaa gagttgatcc tggaacaagg atcatcgtgt tccccttcac caacagcatc   2400
aaccagaggt tcaccctcca gcgcgtc                                       2427
```

<210> SEQ ID NO 28
<211> LENGTH: 2427
<212> TYPE: DNA
<213> ORGANISM: Artificial Sequence
<220> FEATURE:
<223> OTHER INFORMATION: synthetic nucleotide sequence encoding a toxin protein

<400> SEQUENCE: 28

```
atgaacagct accagaacag aaatgaatat gagatcctgg atgcttctcc aaatcatgga     60

aacatctcaa acagatatcc cttcgccaag aatccaaatg ccatggaaaa tgtcaactac    120

aagaactggc tgaatgttag agaagatgtt gctccttcct tcttcggcgg cgcgctgggc    180

atcatcgtca acctcttcaa gcaatatgtc agcttcatca aggctccttc agtttctgga    240

ggcgtcggct tcttgaggac catcattggg ctgatgacaa acagaaatgt catcaacctc    300

accattgatg atgttcaaag gctcatcaac cagagcttgg acaacatcac aagagatgct    360

gcaaacacca agttcacctc aatccagaac aactacaacc agtacctcct caacaggcag    420

aactacagga acaggagctt gccaaggaac atcttcgtcc aaagcctcca gaacattgaa    480

agagagctga gatcagctct ggacagcacc ttctccctcc agaacaggga gctgctgctg    540

ctgccaaact tcacccagat cgccatgctt catctcaccg tgctgagaga tgctgtcatc    600

ttccaaggaa atgatctcat cgtccccacc atctcagaag gacccatcaa cccgctgctg    660

acaaggccgc caagcaacac ctttgaagaa gctctcctca cctccatcag gatctacagc    720

aactactgcg tccgccaata tgaagttggc ctcaacctgc tgaggaacag aggaaacaca    780

tcaaggaact ggctggactt caatgcctac aggctggaga tgaccttcaa ggtgctggat    840

tttgtcaccc tcttctccct cttcgacacc gtcaagtatc ctgtcagcat tgtttcagaa    900

acagattctg acagcacctc gccggtggtg taccagctct caagggtgat ctacacagat    960

cctgttggag ccatcagatc tgatggaaga ggatggtttg atcctcctgt tggaacagat   1020

cgcgtcacct tcaccagcat tgaaaatgag attcctgctc caacaacaag caggcatctt   1080

tcagagctca ccatctcttc tgggccgctg ggcttcggcg tcaatccagc aagaactcac   1140

agctggcaag gaaacagaaa tgtgaacatc tcagctccaa ctgatgtttc tggcgccatc   1200

agcaacagaa caagaaccat cccagcaagg aacatcttca gagtgaacag cagggtgtac   1260

accttggact ggaggctcta tggcgtctac agagcagagt tcttccaagg agctcacagc   1320

caggtgttct cagaaaatcc tccaacagga attggagctc aaagcgccaa caacttcaga   1380

tttcttcctg gagaaaattc tgaaacaccg acgccgcagg actacaccca tgttctctca   1440

agggtggtga atgccaccgt cggcctcacg ccggccaccg gcaaccaaag aaacagcgtg   1500

ctgatctttg gatggaccca caagagcttg acatcagaaa acatctacag gatcaatgag   1560

atcaccaagg tggctgctgt caacacaaga ggaaacagcg gcatcagggt gatctcagga   1620

cctggcttca ctggaggaga tctggtgagg ctggacccta atggaagcgt cagctacaac   1680

ttcacgccgg ccaaccagca agctctgcaa agcaacatca ggatcaggct gagatatgct   1740

tgccaaggaa cagcttcctt gaggatcacc tttggaaatg cttcaagcca ggtgatctcc   1800

ttgatctcca ccaccagcag catcaacaac cttcaatatg aaaacttcca tgtggtgaat   1860

gttccaaaca acatcaactt ccagagcgtc ggcacccaga tcaccatcca gaacatcagc   1920

caaaatccaa acatcagctt ggacagcatt gagctcttct caaacatccc catccctcaa   1980

gaacctccct tcaaccctgt ggtgccagag cctcccatca tctcaggaaa ctaccagatt   2040

gtgacgccgc tggacagaag aagcatcatc gacctcaacc ccaacaacaa tgtcaccctc   2100

tggacaaaca acagaagcag caaccagatc tggaacttca gctatgatca gcagcgcggc   2160

gcctacctca tcaggagctt gagaactgga agcctggtgc tctccatgga ttcaccaaga   2220
```

```
acaagcaatg tttttggata tccaagcaat tctgatgctt ctcagttctg gatcttggag   2280
ccaaatcaag atggcttcat cttcagaagt ttgagggaca ggaacctggt gctggatgtt   2340
tctggaggaa gagttgatcc tggaacaagg atcatcgtct ttcccttcac caacagcatc   2400
aaccaaagat tcaccttgca gcgcgtc                                        2427

<210> SEQ ID NO 29
<211> LENGTH: 2130
<212> TYPE: DNA
<213> ORGANISM: Artificial Sequence
<220> FEATURE:
<223> OTHER INFORMATION: synthetic nucleotide sequence encoding a toxin
      protein

<400> SEQUENCE: 29
atggagagca tcatctgcat gttccgcgtc ctctacatca ggaactacga gcacaccggc     60
ggcatcaaga tgaagccata tcaaaatgaa aatgaatatg agatcctgga tgctcttcca    120
aagtacagca acatcgtcaa tgtttattca agatatcctc tggccaacaa ccctcaagtt    180
cctctccaga acaccagcta caaggactgg ctcaacatgt gccaaaccat cacgccgctc    240
tgcaccccca tcgacattga ttcaaagctg gtggccaccg ccataggcat cctcggcgcc    300
atcttcaagg ccatgccagg acctggaagc gccgtcggcc tcttcttgaa aaccttctcc    360
accatcatcc ccatcttatg gccaaatgac aacaccccca tctggaagga gttcaccaag    420
caaggcttgc agctcttccg gccggagctg ggaagagatg ccatcgagat cattggaaat    480
gatgttcaat caggcttcaa tgctctcaag gaccacatga atgattttga aacaaaattt    540
gagatctggg acaaggacag gacacaaaca aatgccacct acctcatcac cgccttcggc    600
gtcgtcaatg gcaagatcat tgatctaaag aaccagttcc tcatcaaccc cgccaaccag    660
ccggccttcc tcaacctcta tgctcaaaca gcaaacatcg acctcatcct ctaccaaaga    720
ggagctgttt atggagacaa ctgggccaag gccatcaatg acagcagcat ctcacccttc    780
aacagcagcc agatcttcta tgacagcttg aaggccaaga tcaaggagta caccaactac    840
tgtgctgaaa catacaggaa cagcctcacc atcctcaaga accagccaaa catccaatgg    900
gacatctaca acagatacag aagagaagca accctcggcg cgctggatct ggtggcgctc    960
ttccccaact atgacatctg caagtacccc atctcaacaa aaacagagct gacaaggaag   1020
gtgtacatgc cctccttcta cctccaagct ctccagcaca gcaacatcga ggcgctggag   1080
aaccagctca cccatcctcc aagcctcttc acctggctca atgagctcaa cctctacacc   1140
atcagggaga acttcaaccc ggcgctccag gtgagcagcc tctcaggcct ccaggccaag   1200
tacagataca cccagaacag caccatcctg ccaaatcctc ctgctcaagg catcaccaat   1260
ggcaccccca tccccatcat cggcctcaac aacctcttca tctacaagct ctccatgagc   1320
cagtaccgcc atccaaatga ttgtgttcca attgctggca tctccgacat gaccttctac   1380
aagagcgact acaatggaaa tgcttcagca acacaaacat atcaagctgg aaggaacagc   1440
aacaatgtca ttgacacctt catgaatgga cctcaaaatg caagcagcag caacaacatc   1500
tccatcaacc aaacaaacca catcctctcc gacatcaaga tgaactatgc aagaagtgga   1560
ggagtttatg attttggcta cagcttcgcc tggacccaca cctcagttga tccagacaac   1620
ctcatcgtcc ccaacaggat cacccagatc cccgccgtca aggccaactg cctctcctcg   1680
ccggcgcgcg tcattgctgg acctggccac actggaggtg atctggtggc gctgctgaat   1740
ggaggaacac aagctggaag gatgcaaatt caatgcaaaa ctggcagctt caccggcgcc   1800
tcaagaagat atggcatcag gatgagatat gctgcaaata atgccttcac cgtcagcttg   1860
```

agctacaccc tccaaggagg aaacaccatc ggcaccacct tcatcacaga aaggaccttc 1920
agcaggccaa acaacatcat cccaacagat ctgaaatatg aggagttcaa gtacaaggag 1980
tacaaccaga tcatcaccat gacatcacct caaaacacca tcgtcaccat tgccatccag 2040
cagctcaacc ccatcccaaa tgatcagctc atcatcgaca ggatcgagtt ctaccctgtt 2100
gatcaaggag tggtggcctg ccccgtcaac 2130

<210> SEQ ID NO 30
<211> LENGTH: 2130
<212> TYPE: DNA
<213> ORGANISM: Artificial Sequence
<220> FEATURE:
<223> OTHER INFORMATION: synthetic nucleotide sequence encoding a toxin protein

<400> SEQUENCE: 30
atggagagca tcatctgcat gttccgcgtc ctctacatca ggaactatga gcacaccggc 60
ggcatcaaga tgaagccata tcaaaatgaa aatgaatatg agatcctgga tgctcttcca 120
aaatacagca acatcgtcaa tgtttattca agatatcctc tggccaacaa tcctcaagtt 180
cctctccaga acaccagcta caaggactgg ctcaacatgt gccaaaccat cacgccgctc 240
tgcaccccca tcgacattga ttcaaagctg gtggccaccg ccataggcat cctcggcgcc 300
atcttcaagg ccatgccagg acctggaagc gccgtcggcc tcttcttgaa aaccttctcc 360
accatcatcc ccatcttatg gccaaatgac aacaccccca tctggaagga gttcaccaag 420
caaggcttgc agctcttccg gccggagctg ggaagagatg ccatcgagat cattggaaat 480
gatgttcaat caggcttcaa tgctctcaag gaccacatga atgattttga aacaaaattt 540
gagatctggg acaaggacag aacacaaaca aatgccacct acctcatcac cgccttcggc 600
gtcgtcaatg gcaagatcat tgatctaaag aaccagttcc tcatcaaccc cgccaaccag 660
ccggccttcc tcaacctcta tgctcaaaca gcaaacatcg acctcatcct ctaccaaaga 720
ggagctgttt atggagacaa ctgggccaag gccatcaatg acagcagcat ctcacccttc 780
aacagcagcc agatcttcta tgacagcttg aaggccaaga tcaaggagta caccaactac 840
tgtgctgaaa catacaggaa cagcctcacc atcttgaaga accagccaaa catccaatgg 900
gacatctaca acagatacag aagagaagca accctcggcg cgctggatct ggtggcgctc 960
ttccccaact atgacatctg caagtacccc atctcaacaa aaacagagct gacaaggaag 1020
gtgtacatgc catccttcta cctccaagct ctccagcaca gcaacatcga ggcgctggag 1080
aaccagctca cccatcctcc ttctctcttc acctggctca atgagctcaa cctctacacc 1140
atcagggaga acttcaaccc tgctctccag gtgagcagcc tctcaggcct ccaagcaaag 1200
tacagataca cccagaacag caccatcctt ccaaatcctc ctgctcaagg catcaccaat 1260
ggaaccccca tccccatcat cggcctcaac aacctcttca tctacaagct ctccatgagc 1320
cagtaccgcc atccaaatga ttgtgttcca attgctggca tctccgacat gaccttctac 1380
aagagcgact acaatggaaa tgcttcagca acacaaacat atcaagctgg aagaaacagc 1440
aacaatgtca ttgacacctt catgaatgga cctcaaaatg caagcagcag caacaacatc 1500
tccatcaacc aaacaaacca catcctctcc gacatcaaga tgaactatgc aagaagtgga 1560
ggagtttatg attttggcta cagcttcgcc tggacccaca cctcagttga tccagacaac 1620
ctcatcgtcc ccaacaggat cacccagatc cctgctgtca aggccaactg cctctcctcg 1680
ccggcgcgcg tcattgctgg acctggccac actggaggtg atctggtggc gctgctgaat 1740
ggaggaacac aagctggaag gatgcaaatt caatgcaaaa ctggcagctt caccggcgcc 1800
tcaagaagat atggcatcag gatgagatat gctgcaaata atgccttcac cgtcagcttg 1860
agctacaccc tccaaggagg aaacaccatc ggcaccacct tcatcacaga aagaaccttc 1920
tcaaggccaa acaacatcat cccaacagat ctgaaatatg aagagttcaa gtacaaggag 1980
tacaaccaga tcatcaccat gacatcacct caaaacacca tcgtcaccat tgccatccag 2040
cagctcaacc ccatcccaaa tgatcagctc atcatcgaca ggattgagtt ctatcctgtt 2100
gatcaaggag tggtggcctg ccctgtcaac 2130

<210> SEQ ID NO 31
<211> LENGTH: 2061
<212> TYPE: DNA
<213> ORGANISM: Artificial Sequence
<220> FEATURE:
<223> OTHER INFORMATION: synthetic nucleotide sequence encoding a toxin protein

<400> SEQUENCE: 31
atgaagccat atcaaaatga aaatgaatat gagatcctgg atgctcttcc aaagtacagc 60
aacatcgtca atgtttattc aagatatcct ctggccaaca acccccaggt gccgctgcaa 120
aacaccagct acaaggactg gctcaacatg tgccaaacca tcacgccgct ctgcaccccc 180
atcgacattg acagcaagct ggtggccacc gccataggca tcctcggcgc catcttcaag 240
gccatgccag gacctggatc agctgttggc ctcttcttga aaccttctc caccatcatc 300 cccatcctct ggccaaatga caacaccccc atctggaagg agttcaccaa gcaaggcttg 360
cagctcttcc ggccggagct gggaagagat gccatcgaga tcattggaaa tgatgttcaa 420
tcaggcttca atgctctcaa ggaccacatg aatgattttg aaacaaaatt tgagatctgg 480
gacaaggaca ggacacaaac aaatgccacc tacctcatca ccgccttcgg cgtcgtcaat 540
ggcaagatca ttgatctaaa gaaccagttc ctcatcaacc ccgccaacca gccggccttc 600
ctcaacctct atgctcaaac agcaaacatc gacctcatcc tctaccagcg cggcgccgtc 660
tatggagaca actgggccaa ggccatcaat gattcaagca tctctccctt caacagcagc 720
cagatcttct atgacagctt gaaggccaag atcaaggagt acaccaacta ctgtgctgaa 780
acatacagga acagcctcac catcctaaag aaccagccaa acatccaatg ggacatctac 840
aacagataca gaagagaagc aaccctcggc gcgctggatc tggtggcgct cttccccaac 900
tatgacatct gcaagtaccc catctccacc aagacagagc tgacaaggaa ggtgtacatg 960
ccctccttct acctccaagc tctccagcat tcaaacattg aagctctgga gaaccagctc 1020
acccatcctc caagcctctt cacctggctc aatgagctca acctctacac catcagggag 1080
aacttcaacc cggcgctcca ggtgagcagc ctctcaggcc tccaggccaa gtacagatac 1140
acccagaaca gcaccatcct ccccaacccg ccggcgcaag gcatcaccaa tggcaccccc 1200
atccccatca tcggcctcaa caacctcttc atctacaagc tctccatgtc acagtaccgc 1260
catccaaatg attgtgttcc aattgctggc atctccgaca tgaccttcta caagagcgac 1320
tacaatggaa atgcttctgc cacccaaaca tatcaagctg gaaggaacag caacaatgtc 1380
attgacacct tcatgaatgg acctcaaaat gcttcaagca gcaacaacat ctccatcaac 1440
caaacaaacc acatcctctc cgacatcaag atgaactatg caaggagcgg cggcgtctat 1500
gattttggct acagcttcgc ctggacccac acctcagttg atccagacaa cctcattgtt 1560
ccaaacagga tcacccagat ccccgccgtc aaggccaact gcctctcctc gccggcgcgc 1620
gtcattgctg gacctggcca cactggaggt gatctggtgg cgctgctgaa tggaggaaca 1680
caagctggaa ggatgcaaat tcaatgcaaa actggcagct tcactggagc ttcaagaaga 1740
tatggcatca ggatgagata tgctgcaaat aatgccttca ccgtcagctt gagctacacc 1800
ctccaaggag gaaacaccat cggcaccacc ttcatcacag aaaggacctt cagcaggcca 1860
aacaacatca tcccaacaga tctgaaatat gaggagttca agtacaagga gtacaaccag 1920
atcatcacca tgacatcacc tcaaaacacc atcgtcacca ttgccatcca gcagctcaac 1980
cccatcccaa atgatcagct catcatcgac aggatcgagt tctaccctgt tgatcaagga 2040
gtggtggcct gccccgtcaa c 2061

<210> SEQ ID NO 32
<211> LENGTH: 2061
<212> TYPE: DNA
<213> ORGANISM: Artificial Sequence
<220> FEATURE:
<223> OTHER INFORMATION: synthetic nucleotide sequence encoding a toxin protein

<400> SEQUENCE: 32
atgaagccat atcaaaatga aaatgaatat gagatcctgg atgctcttcc aaaatacagc 60
aacatcgtca atgtttattc aagatatcct ctggccaaca accctcaggt gccgctgcaa 120
aacaccagct acaaggactg gctcaacatg tgccaaacca tcacgccgct ctgcaccccc 180
atcgacattg acagcaagct ggtggccacc gccataggca tcctcggcgc catcttcaag 240
gccatgccag gacctggatc agctgttggc ctcttcttga aaaccttctc caccatcatc 300
cccatcctct ggccaaatga caacaccccc atctggaagg agttcaccaa gcaaggcttg 360
cagctcttcc ggccagagct gggaagagat gccatcgaga tcattggaaa tgatgttcaa 420
tcaggcttca atgctctcaa ggatcacatg aatgattttg aaacaaaatt tgagatctgg 480
gacaaggaca gaacacaaac aaatgccacc tacctcatca ccgccttcgg cgtcgtcaat 540
ggaaagatca ttgatctaaa gaaccagttc ctcatcaacc ccgccaacca gccggccttc 600
ctcaacctct atgctcaaac agcaaacatc gacctcatcc tctaccagcg cggcgccgtc 660
tatggagaca actgggccaa ggccatcaat gattcaagca tctctccctt caacagcagc 720
cagatcttct atgacagctt gaaggccaag atcaaggagt acaccaacta ctgtgctgaa 780
acatacagga acagcctcac catcttaaag aaccagccaa acatccaatg ggacatctac 840
aacagataca gaagagaagc aaccctcggc gcgctggatc tggtggcgct cttccccaac 900
tatgacatct gcaagtaccc catctccacc aagacagagc tgacaaggaa ggtgtacatg 960
ccatccttct acctccaagc tctccagcat tcaaacattg aagctctgga gaaccagctc 1020
acccatcctc cttctctctt cacctggctc aatgagctca acctctacac catcagggag 1080
aacttcaacc ctgctctcca ggtgagcagc ctctcaggcc tccaagcaaa gtacagatac 1140
acccagaaca gcaccatcct ccccaacccg ccagctcaag gcatcaccaa tggaaccccc 1200
atccccatca tcggcctcaa caacctcttc atctacaagc tctccatgtc acagtaccgc 1260
catccaaatg attgtgttcc aattgctggc atctccgaca tgaccttcta caagagcgac 1320
tacaatggaa atgcttctgc aacacaaaca tatcaagctg gaagaaacag caacaatgtc 1380
attgacacct tcatgaatgg acctcaaaat gcttcaagca gcaacaacat ctccatcaac 1440
caaacaaacc acatcctctc cgacatcaag atgaactatg caagaagcgg cggcgtctat 1500
gattttggct acagcttcgc ctggacccac acctcagttg atccagacaa cctcattgtt 1560
ccaaacagga tcacccagat ccctgctgtc aaggccaact gcctctcctc gccggcgcgc 1620

-continued gtcattgctg gacctggcca cactggaggt gatctggtgg cgctgctgaa tggaggaaca 1680
caagctggaa ggatgcaaat tcaatgcaaa actggcagct tcactggagc ttcaagaaga 1740
tatggcatca ggatgagata tgctgcaaat aatgccttca ccgtcagctt gagctacacc 1800
ctccaaggag gaaacaccat cggcaccacc ttcatcacag aaagaacctt ctcaaggcca 1860
aacaacatca tcccaacaga tctgaaatat gaagagttca agtacaagga gtacaaccag 1920
atcatcacca tgacatcacc tcaaaacacc atcgtcacca ttgccatcca gcagctcaac 1980
cccatcccaa atgatcagct catcatcgac aggattgagt tctatcctgt tgatcaagga 2040
gtggtggcct gccctgtcaa c 2061

<210> SEQ ID NO 33
<211> LENGTH: 2061
<212> TYPE: DNA
<213> ORGANISM: Artificial Sequence
<220> FEATURE:
<223> OTHER INFORMATION: synthetic nucleotide sequence encoding a toxin protein

<400> SEQUENCE: 33
atgaacagct accagaacaa gaatgaatat gagatcctgg atgcttctca aaacaacagc 60
accatgagca acagatatcc aagatatcct ctggcaaatg atcctcaagc atcaatgcaa 120
aacaccaact acaaggactg gctcaacatg tgtgacagca acacccagtt tgttggagac 180
atctccacct acagctctcc agaagctgct ctctccgtga gagatgctgt gctcaccggc 240
atcaacaccg ccggcaccat cctctcaaac ctcggcgtgc catttgcttc tcagagcttt 300
gggatgattg gtaggatcat cggcatcctc tggccagggc cagatccatt tgctgctctg 360
atggtgctgg tggaggagct catcaaccag aggatcaatg atgagatcag gaaccatgct 420
ctactggagc tcgccggcct caagggcatc atggacctct acaggacaag atggagagca 480
tgggatctga acaaggacaa cccagaaaca agagaagctg ttcgagctca gtacagaact 540
gctgacaact tcttcatcca gaacatgcca aaatttggaa gagaagatca tggcgtgctg 600
ctgctacctg tttatgctca agctgccaac atgcacctca tcctcctccg tgatgcatat 660
gtttttggaa ctggatgggg ccttggacct ggagaggtga gggacaacta cacaaggctg 720
caagagaaga tcagggagta caaggaccac tgcgtcacct tctacaacca aggcctcaac 780
aggttcaaca gatcaaatgc tcaagattgg gtgagcttca acaggttcag aactgacatg 840
accctcaccg tgctggacct cgccatcctc ttccccaact atgatccaag gatctacccc 900
tccgccgtca agacagagct gacaagggag atctacacag atcctgttgg cttcaccggc 960
gtgctgggct caggaggaag aacatatcca tggtacaacc caaatgacac cagcttcgcc 1020
accatggaga actctgcaag aagaaggcct tccttcacca cctggctgaa caggatcagg 1080
atcttcactg gtcacatcgg caacttctct gctgctggaa atgtttgggg aggccatgag 1140
ctctttgaaa gaagcaacaa tggatcagag atcatccaaa gatttggcaa caccaacacc 1200
agctacacgc cggtgaggaa ctgggacttc accaaccaga acaggacggt gttctccatt 1260
gcttcaacag caagggtgct gctggctgga tctgaaggaa atgctcaccg gccaagccaa 1320
tatggagttt caagggtgga catgcacacc gccattggag gaaacaccag cggcggccag 1380
ttcatctatg aagttccaaa tgttcacagc agccagaaca tcttgagcga gctgccagga 1440
gaaaaccagc agcggccaga tgcaaggaac cacagccaca tcctcagcta catctcaaat 1500
tttgatgcaa aaagaggagg aactgttgga aatgtcaggc tgctgacata tggatggacc 1560
cacacctcca tggacaggaa caacaggctg gagagggaca ggatcactca aattgatgct 1620

```
gtcaagggct ggggcggcgt caccggcagc gtcatccctg ggccaactgg aggtagcttg   1680

gtcaccatcc cttcaaatcc atggagcgtg agcctccgcg tccaagctcc tcagatccaa   1740

acaaactaca ggatcaggct gcgcttcgcc tgcgtctggc ctggagctca ccacatgtgg   1800

gtgacatatg gaggcatcag ccatcctgtg cagctctgca acaacccttc ttctggaagg   1860

ccaagcaaca acctgctgga aagtgatttt ggatatgtgg tggtgcctgg caccttctca   1920

ccaagcatca acccagagat aaggttctcc gccatcagca atgctcctgt gctggacaag   1980

atcgagttca tcccgctgga catctacaat gagcacttcg tggaggagcg cgccaagacc   2040

atcaatgatc tcttcatcaa c                                             2061
```

<210> SEQ ID NO 34
<211> LENGTH: 2061
<212> TYPE: DNA
<213> ORGANISM: Artificial Sequence
<220> FEATURE:
<223> OTHER INFORMATION: synthetic nucleotide sequence encoding a toxin protein

<400> SEQUENCE: 34

```
atgaacagct accaaaacaa gaatgaatat gagatcctgg atgcttctca aaacaacagc     60

accatgagca acagatatcc aagatatcct cttgcaaatg atcctcaagc atcaatgcaa    120

aacaccaact acaaggattg gctcaacatg tgtgacagca acacccaatt tgttggagac    180

atctccacct acagctctcc agaagctgct ctctctgtga gagatgctgt tctcaccggc    240

atcaacaccg ccggcaccat cctctcaaac ctcggcgtgc catttgcttc tcagagcttt    300

gggatgattg gtaggatcat tggcatcctc tggcctggac cagatccatt tgctgctctg    360

atggtgctgg tggaggagct catcaaccaa aggatcaatg atgagatcag gaaccatgct    420

ctactggagc tggctggcct caagggcatc atggatctct acagaacaag atggagagca    480

tgggatctga acaaggacaa tccagaaaca agagaagctg ttcgagctca gtacagaact    540

gctgacaact tcttcatcca gaacatgcca aaatttggaa gagaagatca tggagtgctg    600

ctgctacctg tttatgctca agctgcaaac atgcacctca tcctcctccg tgatgcatat    660

gtttttggaa ctggatgggg ccttggacct ggagaagtga gggacaacta cacaaggctg    720

caagagaaga tcagggagta caaggatcac tgcgtcacct tctacaacca aggcctcaac    780

aggttcaaca gatcaaatgc tcaagattgg gtgagcttca acaggttcag aactgacatg    840

accctcaccg tgctggatct ggccatcctc ttccccaact atgatccaag gatctacccc    900

tccgccgtca agacagagct gacaagggag atctacacag atcctgttgg cttcaccggc    960

gtgctgggat caggaggaag aacatatcca tggtacaacc caaatgacac cagcttcgcc   1020

accatggaga actctgcaag aagaaggcct tccttcacca cctggctgaa caggatcagg   1080

atcttcactg gtcacattgg aaacttctct gctgctggaa atgtttgggg aggacatgag   1140

ctctttgaaa gaagcaacaa tggatcagag atcatccaaa gatttggaaa caccaacacc   1200

agctacacgc cggtgaggaa ctgggacttc accaaccaaa acaggacggt gttctccatt   1260

gcttcaacag caagggtgct gctggctgga tctgaaggaa atgctcatcg gccttctcaa   1320

tatggagttt caagggtgga catgcacacc gccattggag gaaacaccag cggcggccag   1380

ttcatctatg aagttccaaa tgttcacagc agccaaaaca tcttgagcga gcttcctgga   1440

gaaaaccagc agaggccaga tgcaaggaac cacagccaca tcctcagcta catctcaaat   1500

tttgatgcaa aaagaggagg aactgttgga aatgtcaggc tgctgacata tggatggacc   1560
```

cacacctcca tggacaggaa caacaggctg gagagggaca ggatcactca aattgatgct 1620
gtcaaaggat ggggcggcgt caccggcagc gtcatccctg gaccaactgg aggtagcttg 1680
gtcaccatcc cttcaaatcc atggagcgtg agcctccgcg tccaagctcc tcagatccaa 1740
acaaactaca ggatcaggct gaggttcgcc tgcgtctggc ctggagctca tcacatgtgg 1800
gtgacatatg gaggcatcag ccatcctgtt cagctctgca acaatccttc ttctggaagg 1860
ccaagcaaca acctgctgga aagtgatttt ggatatgtgg tggttcctgg aaccttctca 1920
ccaagcatca atccagaaat aaggttctcc gccatcagca atgctcctgt gctggacaag 1980
attgagttca tccctctgga catctacaat gagcattttg tggaggagcg cgccaagacc 2040
atcaatgatc tcttcatcaa c 2061

<210> SEQ ID NO 35
<211> LENGTH: 1872
<212> TYPE: DNA
<213> ORGANISM: Artificial Sequence
<220> FEATURE:
<223> OTHER INFORMATION: synthetic nucleotide sequence encoding a toxin protein

<400> SEQUENCE: 35
atgaacagct accagaacaa gaatgaatat gagatcctgg acacctcccc caacaacagc 60
accatgagca ccctccatcc aagatatcct ctagcaaaag atccatacaa gccaatgagg 120
aacaccaact acaaggaatg gctggccatg tgcgccaaca acaaccaagt tccaattgat 180
cctctggaca acacctgggc cggcgtcatg gcggcgctct tcgcctccgc cgccgccatt 240
gctgggctga tgtctgctgt tcctgttttc tcagtggtgg ccaccggcac ggcgctcgcc 300
gccgcgctca cccccatcct cttcccaagc aatggaccag atgtttcaac tcagctgatg 360
agcaacactg aagctctgct gaagagggag ctggacacat atgtccgcgc gcgcgccgac 420
agcgagttcc aagctctgga agctcaaagg gagttcttca agagcgcctt cgactactgg 480
aagctctacc ccaccaactc aaatgccatt gccaccgtcg ccgcgcgctt ccacaccgtc 540
aatggcgcct tcgtcaccgc catgaggctc ttcagaactg ctggatatga agctctgctg 600
ctgccagttt atgctcaagc tgcaaggctg cacctcctcc acctccgcga cggcgtcctc 660
ttcgccaatg aatggggcct agcaaaagat cctggagatc ttcatgatca agagttcaac 720
aaatatgctg ctgaatatgc tgattattgt gaaagcacct acaacacaga gctcaacagg 780
atcaagacgg cgccaggaaa aacatggctg gactacaacc agtacaggag gatcatgacc 840
attgctgtgc tggacattgc tgccaagttc tcaatcctca acccgcgcct ctacaggctg 900
ccgctgcaag aagagatctt gacaaggaag atctacacag atcctgtcaa cttctcacca 960
gggccaagca ttgctgatga tgagaacaga tacaccgtgc cgctctcctt ggtgacccag 1020
ctggtgaaca gcaggctctt caccaatgtt gcttctgctc aaaatgctgg cttcatcggc 1080
aaccagaaca gatacaagaa catcggcgtg ggagatcctg ttgatggccc catcatcggc 1140
caatcagttt atgagaaggt ggatgctggc atcccaacaa atgaatgggt gtatgaagtt 1200
ggcgtcaatg gcatccaaaa tgattatcca aggaacatcg gcctgaggaa aggatcaacc 1260
accgccttca cagatcatct tgctggaagc cagtacaacc tggggccgct gacaagggtg 1320
agcatcccca ccaaggacaa tgctcccatc aacaacacca acttcaccca ccgcctctcc 1380
gacatcatcc ttcctggcaa caaaggatca tccttcgcct ggacccatgt tgatgttgat 1440
ccaacaggaa actacctctc caccaccaag atcaacctca tccccgccac caaggccagc 1500
aagattcctc tctccttcta cttgaggaaa ggacctggct tcattggagg agatctggtg 1560
aggctgggca gcggctttga atgcagctac aagttcaact tcaagagccc tggaagctca 1620
gcaaacttca gaatcaggat cagatatgct ggagctggaa gcggccaagg agctgatggc 1680
caggtgtact tcaagctagg aaactacacc tcgccgacga cgccatgggg ccacactgga 1740
tttgattatg gaaatgtcaa gtacaaccag ttccgcgtgc tggagctctt tggaacagca 1800
gagaacatca ccgacaatga tctgaagatc atcgtctgga caggaagctc tgctcaagat 1860
ttcctctcca gg 1872

<210> SEQ ID NO 36
<211> LENGTH: 1872
<212> TYPE: DNA
<213> ORGANISM: Artificial Sequence
<220> FEATURE:
<223> OTHER INFORMATION: synthetic nucleotide sequence encoding a toxin protein

<400> SEQUENCE: 36
atgaacagct accaaaacaa aaatgaatat gagatcttgg acacctctcc aaacaacagc 60
accatgagca ccctccatcc aagatatcct ctagcaaaag atccatacaa gccaatgagg 120
aacaccaact acaaggaatg gctggccatg tgcgccaaca acaaccaagt tccaattgat 180
cctctggaca acacctgggc cggcgtcatg gcggcgctct tcgcctccgc cgccgccatt 240
gctggcttga tgtctgctgt tcctgttttt tcagtggtgg ccaccggcac ggcgctcgcc 300
gccgcgctca cccccatcct cttcccttca aatggaccag atgtttcaac tcagctgatg 360
agcaacactg aagctctgct gaagagggag ctggacacat atgtccgcgc gcgcgccgac 420
agcgagttcc aagctctgga agctcaaaga gagttcttca agagcgcctt cgactactgg 480
aagctctacc caacaaattc aaatgccatt gccaccgtcg ccgcgcgctt ccacaccgtc 540
aatggagcct tcgtcaccgc catgaggctc ttcagaactg ctggatatga agctctgctg 600
cttcctgttt atgctcaagc tgcaaggctg catctcctcc acctccgaga tggcgtcctc 660
tttgcaaatg aatggggcct agcaaaagat cctggagatc ttcatgatca agagttcaac 720
aaatatgctg ctgaatatgc tgattattgt gaaagcacct acaacacaga gctcaacagg 780
atcaagacag ctccaggaaa aacatggctg gactacaacc agtacagaag gatcatgaca 840
attgctgtgc tggacattgc tgcaaagttc tcaatcctca acccaaggct ctacaggctg 900
ccgctgcaag aagaaatctt gacaaggaag atctacacag atcctgtcaa cttctcacca 960
ggaccaagca ttgctgatga tgaaaacaga tacaccgtgc ctctctcctt ggtgacacag 1020
ctggtgaaca gcaggctctt caccaatgtt gcttctgctc aaaatgctgg cttcattgga 1080
aaccaaaaca gatacaagaa catcggcgtt ggagatcctg ttgatggccc catcattgga 1140
caatcagttt atgagaaggt ggatgctggc atcccaacaa atgaatgggt gtatgaagtt 1200
ggtgtcaatg gcatccaaaa tgattatcca agaaacattg gcttgaggaa aggatcaaca 1260
acagccttca cagatcatct tgctggaagc cagtacaacc ttgggccgct gacaagggtg 1320
agcatcccca ccaaggacaa tgctcccatc aacaacacca acttcaccca ccgcctctct 1380
gacatcatcc ttcctggaaa caaaggatca tccttcgcct ggacacatgt tgatgttgat 1440
ccaacaggaa actacctctc caccaccaag atcaacctca tccctgccac caaggcaagc 1500
aagattcctc tctccttcta cttgagaaaa ggacctggct tcattggagg agatctggtg 1560
aggctgggct ctggctttga atgcagctac aagttcaact tcaagagccc tggaagctca 1620
gcaaacttca gaatcaggat cagatatgct ggagctggaa gcggccaagg agctgatggc 1680
caagtttact tcaagctagg aaactacacc tcgccgacga cgccatgggg ccacactgga 1740
tttgattatg gaaatgtcaa gtacaaccag ttcagagtgc tggagctctt tggaacagca 1800
gaaaacatca ccgacaatga tctgaagatc atcgtctgga caggaagctc tgctcaagat 1860
ttcctctcaa ga 1872

<210> SEQ ID NO 37
<211> LENGTH: 888
<212> TYPE: DNA
<213> ORGANISM: Artificial Sequence
<220> FEATURE:
<223> OTHER INFORMATION: synthetic nucleotide sequence encoding a toxin protein

<400> SEQUENCE: 37
atgaagaagc tgatgttctc cttggtggcc accaccatga gcatgggcct catcctcggc 60
agcgcgccgg tgaaggctga tgtcagcaac aagaacagcg cctaccagga cattgatgaa 120
agggtgaaga agatggctca atcagcagca tggggaggac aagaatacag gaaccacaac 180
atcaaggaca tcgagctgaa gggcaacctc attgatggaa gcatgattga gaacagcgag 240
gtgctcaccg tcagcagcga catcctggag aacaagctgg gtcacaccgt caacatgcca 300
tcaacaggat atgaacatga atttgaagaa acaacaaaca ccaccaacac cagcggctgg 360
acatttggct acaactacaa tgcttccttc tccgtgctga tggtttcagc ttctcagagc 420
ttctccgtgg agtacaacat gagcaccagc aacacccatg agaagaagga gaagaggaag 480
ttcactgttc cttccatcga ggttcctgtt cctgctggca agaagtacaa ggtggaatat 540
gtttttgaga aggtgaaggt gtcagggaag aacaagattg atgccaacct ctatggagat 600
gtcacctact actacaacaa ccagccaatg tcgccgcagc tgctgtacag cgtccaaggc 660
ctcgccgccg acaagcaagg cttcgagcag gtcatcagag attctgctgt tggaaatgac 720
agatttggca tcaagacaac tggcattggt cagttctcaa cagaatttgg aacaaggctg 780
acaaggacct tgacagacat caccgacaca aggaaccccg tcaaggtgga aacaaaaaat 840
gttcctgtgg agttcaagac cctctccatc gacacaaggg tgatcaag 888

<210> SEQ ID NO 38
<211> LENGTH: 888
<212> TYPE: DNA
<213> ORGANISM: Artificial Sequence
<220> FEATURE:
<223> OTHER INFORMATION: synthetic nucleotide sequence encoding a toxin protein

<400> SEQUENCE: 38
atgaagaagc tgatgttctc cttggtggcc accaccatga gcatgggcct catcctcggc 60
agcgcgccgg tgaaggctga tgtcagcaac aagaacagcg cctaccagga cattgatgaa 120
agggtgaaga agatggctca atcagcagca tggggaggac aagaatacag gaaccacaac 180
atcaaggaca tcgagctgaa gggcaacctc attgatggaa gcatgattga gaacagcgag 240
gtgctcaccg tcagcagcga catcctggag aacaagctgg gtcacaccgt caacatgcca 300
tcaacaggat atgaacatga atttgaagaa acaacaaaca ccaccaacac cagcggctgg 360
acatttggct acaactacaa tgcttccttc tccgtgctga tggtttcagc ttctcagagc 420
ttctccgtgg agtacaacat gagcaccagc aacacccatg agaagaagga gaagaggaag 480
ttcactgttc cttccattga agttcctgtt cctgctggca agaagtacaa ggtggaatat 540
gtttttgaga aggtgaaggt gtcagggaag aacaagattg atgccaacct ctatggagat 600
gtcacctact actacaacaa ccagccaatg tcgccgcagc tgctgtacag cgtccaaggc 660
ctcgccgccg acaagcaagg cttcgagcag gtcatcagag attctgctgt tggaaatgac 720
agatttggca tcaagacaac tggcattggt cagttctcaa cagaatttgg aacaaggctg 780
acaaggacct tgacagacat caccgacaca aggaaccccg tcaaggtgga aacaaaaaat 840
gttcctgtgg agttcaagac cctctccatc gacacaaggg tgatcaag 888

<210> SEQ ID NO 39
<211> LENGTH: 924
<212> TYPE: DNA
<213> ORGANISM: Artificial Sequence
<220> FEATURE:
<223> OTHER INFORMATION: synthetic nucleotide sequence encoding a toxin protein

<400> SEQUENCE: 39
atgaagaaga acaggatgct gctgaaatgg atgtgcggcc tcaccatcgg catcggcagc 60
ttgacaggag gaagcctcaa tgcttttgct gatgaagttt cagattctct tgctgatgtt 120
ggcttcctct atggagacta cctctacaag accaagcagc atcctcaagg aaccctcccc 180
atcacctacc ccatgaggga gatcaacaac taccagatca tcgacaagag cgtcagccaa 240
gttggatcaa cagaatatga agaaggacaa accctctatg ttgatgatga tgtttttgac 300
aacaagacag gaacagatca aaccttcaag accatccagt ttgagaagga gttctcagaa 360
acagcaacaa gcagcaccac ccattctgtt ggcaccagct tggaggagag cgtgaagttc 420
gacttctttg ttggagaagg aagcgccaag ttcaccgtca actacaactt ctccaagaca 480
ggaagcctct ccaccagcaa caagatcaag tacacccttc cttcacaaag catcaatgtt 540
cctgccaaca agaaatatga ggtgatctgc gtgctggaaa caaagaaggc caaggcaaat 600
gttcagttca atgttgatgt tctaggaaat gcaaaatatg tctacagcaa caacagcccc 660
tacacgccaa aatatgagag cggcgccacc atgctcaaga ccctcaatga gaagaaccca 720
actccttctg tcagctggct gggcaaggaa tgggagaaat gggagtacca tgatggcaag 780
gcgcgctaca agaatggatc aggaacagtt tctgctgaat atggaacaag gatggtgctg 840
gtgatcaatg acatcaccaa caacaagaca agaggaagca aggagattgc aaggattcct 900
gtcaccccca tccagaagca gatg 924

<210> SEQ ID NO 40
<211> LENGTH: 924
<212> TYPE: DNA
<213> ORGANISM: Artificial Sequence
<220> FEATURE:
<223> OTHER INFORMATION: synthetic nucleotide sequence encoding a toxin protein

<400> SEQUENCE: 40
atgaagaaga acaggatgct gctgaaatgg atgtgcggcc tcaccatcgg catcggcagc 60
ttgacaggag gaagcctcaa tgcttttgct gatgaagttt cagattctct tgctgatgtt 120
ggcttcctct atggagacta cctctacaag accaagcagc atcctcaagg aaccctcccc 180
atcacctacc ccatgaggga gatcaacaac taccagatca tcgacaagag cgtcagccaa 240
gttggatcaa cagaatatga agaaggacaa accctctatg ttgatgatga tgtttttgac 300
aacaagacag gaacagatca aaccttcaag accatccagt ttgagaagga gttctcagaa 360
acagcaacaa gcagcaccac ccattctgtt ggcaccagct tggaggagag cgtgaagttc 420
gacttctttg ttggagaagg aagcgccaag ttcaccgtca actacaactt ctccaagaca 480
ggaagcctct ccaccagcaa caagatcaag tacacccttc cttcacaaag catcaatgtt 540
cctgccaaca agaaatatga ggtgatctgc gtgctggaaa caaagaaggc caaggcaaat 600
gttcagttca atgttgatgt tctaggaaat gcaaaatatg tctacagcaa caacagcccc 660
tacacgccaa aatatgagag cggcgccacc atgctcaaga ccctcaatga gaagaaccca 720
actccttctg tcagctggct gggcaaggaa tgggagaaat gggagtacca tgatggcaag 780
gcgcgctaca agaatggatc aggaacagtt tctgctgaat atggaacaag gatggtgctg 840
gtgatcaatg acatcaccaa caacaagaca agaggaagca aggagattgc aaggattcct 900
gtcaccccca tccagaagca gatg 924

<210> SEQ ID NO 41
<211> LENGTH: 1995
<212> TYPE: DNA
<213> ORGANISM: Artificial Sequence
<220> FEATURE:
<223> OTHER INFORMATION: synthetic nucleotide sequence encoding a toxin protein

<400> SEQUENCE: 41
atgcaaatca tcgacagcag cagcaatgat ttctcccaaa gcaacagata tccaagatat 60
cctctggcca aggagagcaa ctacaaggac tggctggcaa gctgtgatga aagcaatgtg 120
gacaccctct ccgccaccag caatgtccgc gcctctgttt caagagctct tggcattgtg 180
aatcagatcc tcggcttcct cggcctcggc ttcatcggca ccggcctcgg cgtcctctca 240
gatctcttca acagcttctg gccaagcaat gacaacagca tctgggagag cttcttgagg 300
agcgtggagg agctcatcga ccgccgcgtc agggaggtgg agaggttcag aattgaaagc 360
cagttcaccg gcctcagaaa tgtgatgtca aactacaatg gagctcttcg agattggaat 420
ggcaacagga acaacctggc gctgcaaagc gaggtgagga gcagatttga caactctgat 480
gatgcttttg cttcaaggat gccggagttc agaattgaag gatttgagat ccagagcctc 540
gccgtctatg ctcaagctgc caccctccac ctgctgctgc tgagagatgg agtggtgaat 600
ggcctccaat ggggcttcga catcgtcacc gtcaacaggc tctatgagaa gctggtctgc 660
ctctccggcg cctatgctga tcactgcacc ctcttctaca ggcaagggct ggaggagcta 720
aggaacagag gaaactggaa tgccttcaac aactacagga gggacatgac cctccaggtg 780
ctggatgtca tctccctctt ccccaactat gatccaaggc tctatgacat caacaccaac 840
acccagctga caagggagat ctacacagag ccgctggcca tccctggatg gctcaacagc 900
cattcaaatc caacccagtt ccagcagatt gaaaatgatc tcatcagatc tccttctgtg 960
ttcagcaacc tggaaactct cttcatggaa gctggcttcg ccttctttca agctggcatt 1020
gctcgccaag ctgtgctgag gacaaggaca agcagcctca acatgaacag gaccgccgtc 1080
atcgtcacgc catggcaagg agctcctcat ccaaatgttt cacatgagct ccaggtgacc 1140
ctccaggaca gaaatgtttt caacatcaac agcgtggtgg gaagggagat ctcctctcaa 1200
actggcctcc tcttcggcgt ccagcaggcc accttccact tcgtctgggc tggaggaaat 1260
gctgccacca ccacccagtt caaccttcct cccatctcag gccatagcac cagcataaca 1320
agcaacatcc ctggcaccaa cagcaccacg ccaacaggaa gcgactacac ccaccgcctc 1380
tcctccatca cctccacctc cgtcggcacc tggcagaggg acaggaccaa cataatggca 1440
tatggatgga cccatgtttc agctgaaaga acaaacagga tcatccccaa caggatcacc 1500
cagatccccg ccgtcaaagg aagcctcttc tccgacaacc ctccaaacac ctcaaggaca 1560
agggtggaga atggacctgg tcacactgga ggagggctgg tggtgatgga tggaggaaca 1620
tcagtgctcc agatgagggt cacctcctcc gcgcgccaaa gatatgacat gaggctgcgc 1680
tatgtggcgc tggcgccggc gacggtggag gtgaggattc cagagctcgg cggccatgtc 1740
cgcttccaga tgccaatgac agcaacaggg ctgccggcgc cgctaccata cagccacctc 1800
agatatgtgg acatcccgct gagatttgaa actcctcatg gagaaaacac ctggaccttc 1860
gagctgcaaa caaccttcgc cgccgtcgcc atcgacaggg tggagttcat ccccgtcaat 1920
gcaacagctc tggaatatga aggaaagagg cacctggaga aggccaagaa ggctgttgga 1980
gatctcttca tcaac 1995

<210> SEQ ID NO 42
<211> LENGTH: 1995
<212> TYPE: DNA
<213> ORGANISM: Artificial Sequence
<220> FEATURE:
<223> OTHER INFORMATION: synthetic nucleotide sequence encoding a toxin protein

<400> SEQUENCE: 42
atgcaaatca tcgacagcag cagcaatgat ttctctcaaa gcaacagata tccaagatat 60
cctctggcca aggaaagcaa ctacaaggat tggctggcaa gctgtgatga aagcaatgtt 120
gacaccctct ccgccaccag caatgtccgc gcctctgttt caagagctct tggaattgtg 180
aatcagatcc ttggcttcct tggccttggc ttcattggca ctggcctcgg cgtcctctca 240
gatctcttca acagcttctg gccatcaaat gacaacagca tctgggagag cttcttgagg 300
agcgtggagg agctcatcga ccgccgcgtc agagaggtgg aaaggttcag aattgaaagc 360
cagttcactg gcttgagaaa tgtgatgtca aactacaatg gagctcttcg agattggaat 420
ggaaacagaa acaacttggc gctgcaatca gaggtgagaa gcagatttga caattctgat 480
gatgcttttg cttcaaggat gccagagttc agaattgaag gatttgagat ccaaagcctc 540
gccgtctatg ctcaagctgc aaccctccat ctgctgctgc tgagagatgg agtggtgaat 600
ggccttcaat ggggcttcga cattgtcacc gtcaacaggc tctatgagaa gctggtttgc 660
ttgagcggcg cctatgctga tcattgcacc ctcttctaca ggcaagggct ggaggagcta 720
agaaacagag gaaactggaa tgccttcaac aactacagaa gagacatgac cctccaggtg 780
ctggatgtca tctccctctt cccaaactat gatccaaggc tctatgacat caacaccaac 840
acccagctga caagagagat ctacacagag ccgctggcca tccctggatg gctcaacagc 900
cattcaaatc caacacagtt ccagcagatt gaaaatgatc tcatcagatc tccttctgtt 960
ttcagcaacc tggaaacatt gttcatggaa gctggcttcg ccttctttca agctggaatt 1020
gcaaggcaag ctgtgctgag aacaagaaca agcagcttga acatgaacag gacagctgtc 1080
atcgtcactc catggcaagg agctcctcat ccaaatgttt cacatgagct gcaagtgaca 1140
ttgcaagaca gaaatgtttt caacatcaac agcgtggttg gaagagagat ctcttctcaa 1200
actggcctcc tcttcggcgt ccagcaagca accttccact tcgtctgggc tggaggaaat 1260
gctgccacca ccacccagtt caaccttcct cccatctcag gacatagcac cagcataaca 1320
agcaacattc ctggaacaaa cagcacaaca ccaacaggaa gcgactacac ccaccgcctc 1380
tcctccatca cctccacctc tgttggcaca tggcaaagag acagaacaaa cataatggca 1440
tatggatgga cacatgtttc agctgaaaga acaaacagga tcatccccaa caggatcacc 1500
cagatccctg ctgtcaaagg aagcctcttc tctgacaatc ctccaaacac atcaagaaca 1560
agggtggaaa atggacctgg tcacactgga ggagggctgg tggtgatgga tggaggaaca 1620
tcagttcttc agatgagggt cacctcctcc gcgcgccaaa gatatgacat gaggctgagg 1680
tatgttgctc tggcgccggc gacggtggag gtgaggattc cagagcttgg aggccatgtt 1740
aggttccaga tgccaatgac agcaacaggg ctgccggcgc ctctaccata cagccatctg 1800
agatatgttg acattccttt gagatttgaa actcctcatg gagaaaacac atggacattt 1860
gagctgcaaa caaccttcgc cgccgtcgcc atcgacaggg tggagttcat ccctgtcaat 1920
gcaacagctc tggaatatga aggaaaaagg catctggaga aggccaagaa ggctgttgga 1980
gatctcttca tcaac 1995

<210> SEQ ID NO 43
<211> LENGTH: 1563
<212> TYPE: DNA
<213> ORGANISM: Artificial Sequence
<220> FEATURE:
<223> OTHER INFORMATION: synthetic nucleotide sequence encoding a toxin protein

<400> SEQUENCE: 43
atgacaaaga gcgagttcat ccagaacagc tgccggaaga tgcaaagcaa ggtgcgcgtc 60
atcatcctct ccaccaatga tcctgtggtg aacaacaaca ccttggacat cacagagatc 120
aaggatcttg ctcatctctc ccaggccatc atgctggcca acaacttcca agctgctctg 180
gtgccaacaa gctcagaatt tggccaagat gtgctgagat ttgatgtcaa ccaaggcatc 240
agcattgcca acaacatcta ccccaaggcg gtggacatca actacatcag caggacgctc 300
tcccaaagca acaaccaggt gaacagcatg atcaacatgg tggtgaatga gctgaagctg 360
ctgctgggca tcaaccttgc tgattcagtg ctccagcagc tcaccagctt ggtggcctac 420
accttcacca acctctacac ccagcagaac agcgcctggg tgttctgggg gaagcaagca 480
tcaaatcaaa caaactacac ctacaacatc gtctttgcca tccaaaatgc tcaaactgga 540
aacttcatga aggccatccc catgggcttt gagatctctg catatgctgt caaggagcag 600
gtgctcttct tcaccatcca agattatgct tcatattctg tgaagatcca ggccatcaat 660
gtcacccagc cgctcatcaa cagcagctat ggaagcctct ccggcgtcta caacatcatc 720
accgcgctca acaacatctc cgtcatcacc atgagcaact ctgatgaaaa tgtcaaccta 780
tggtatgaca atgatgatct caaccaaaaa tggatcttgg agttcaacca caaccactac 840
gcctacatca tcaggaacct ctccaacagg agcttggtgc tgacatggga cagcaccagc 900
ggcagcaaca atgtttttgc caccaactac caaggaaatg atgagcagtt ctggatcatc 960
caggacaccg acaatgacta cttctacctc tcaaacatga gggacaccca atatgtgctg 1020
gagattgctg gaagcgtgtt ctacaatgga actaatgtca tcgtcaacaa gaaaacaagc 1080
agcctcaacc agaagttctc catcaacagg atcaacaggc agatccaaaa tggcatctac 1140
aacatcacca cctacctgaa tgcttcttct gtcatcacca tgtcaacaga ctacaacatc 1200
aatgttcatg attatcctgt caacctctgg ttcaagaatg acagcatcaa ccaaaaatgg 1260
atcttcgagt ttgattcaga caagagcgcc tacagggtga ggagcgtcag caacccctcc 1320
ctcttcctca gctggccggt ggcctccttc accaacagag ctgctgtcac cccaaatcca 1380
agggacaatg aatacttctg gttcctccag agcgccggcc tcggcacctt ctacctggtg 1440
tcaatgaggg acacaagata tgtgctggag gtggagaaca gcaacatcga caatggcacc 1500
aacatcatcg tcaaccaaag aactggaaac ttcaaccaga ggttctacat cgagaacatc 1560
aac 1563

<210> SEQ ID NO 44
<211> LENGTH: 1563
<212> TYPE: DNA
<213> ORGANISM: Artificial Sequence
<220> FEATURE:
<223> OTHER INFORMATION: synthetic nucleotide sequence encoding a toxin protein

<400> SEQUENCE: 44

```
atgacaaaga gcgagttcat ccagaacagc tgccggaaga tgcaaagcaa ggtgcgcgtc     60
atcatcctct ccaccaatga tcctgtggtg aacaacaaca ccttggacat cacagagatc    120
aaggatcttg ctcatctctc ccaggccatc atgctggcca acaacttcca agctgctctg    180
gtgccaacaa gctcagaatt tggccaagat gtgctgagat ttgatgtcaa ccaaggcatc    240
agcattgcca acaacatcta ccccaaggcg gtggacatca actacatcag caggacgctc    300
tcccaaagca acaaccaggt gaacagcatg atcaacatgg tggtgaatga gctgaagctg    360
ctgctgggca tcaaccttgc tgattcagtg ctccagcagc tcaccagctt ggtggcctac    420
accttcacca acctctacac ccagcagaac agcgcctggg tgttctgggg gaagcaagca    480
tcaaatcaaa caaactacac ctacaacatc gtctttgcca tccaaaatgc tcaaactgga    540
aacttcatga aggccatccc catgggcttt gagatctctg catatgctgt caaggagcag    600
gtgctcttct tcaccatcca agattatgct tcatattctg tgaagatcca ggccatcaat    660
gtcacccagc cgctcatcaa cagcagctat ggaagcctct ccggcgtcta caacatcatc    720
accgcgctca acaacatctc cgtcatcacc atgagcaact ctgatgaaaa tgtcaaccta    780
tggtatgaca atgatgatct caaccaaaaa tggatcttgg agttcaacca caaccactac    840
gcctacatca tcaggaacct ctccaacagg agcttggtgc tgacatggga cagcaccagc    900
ggcagcaaca atgtttttgc caccaactac caaggaaatg atgagcagtt ctggatcatc    960
caggacaccg acaatgacta cttctacctc tcaaacatga gggacaccca atatgtgctg   1020
gagattgctg gaagcgtgtt ctacaatgga actaatgtca tcgtcaacaa gaaaacaagc   1080
agcctcaacc agaagttctc catcaacagg atcaacaggc agatccaaaa tggcatctac   1140
aacatcacca cctacctgaa tgcttcttct gtcatcacca tgtcaacaga ctacaacatc   1200
aatgttcatg attatcctgt caacctctgg ttcaagaatg acagcatcaa ccaaaaatgg   1260
atcttcgagt ttgattcaga caagagcgcc tacagggtga ggagcgtcag caacccctcc   1320
ctcttcctca gctggccggt ggcctccttc accaacagag ctgctgtcac cccaaatcca   1380
agggacaatg aatacttctg gttcctccag agcgccggcc tcggcacctt ctacctggtg   1440
tcaatgaggg acacaagata tgtgctggag gtggagaaca gcaacatcga caatggcacc   1500
aacatcatcg tcaaccaaag aactggaaac ttcaaccaga ggttctacat cgagaacatc   1560
aac                                                                 1563
```

<210> SEQ ID NO 45
<211> LENGTH: 4
<212> TYPE: PRT
<213> ORGANISM: Artificial Sequence
<220> FEATURE:
<223> OTHER INFORMATION: endoplasmic reticulum targeting peptide

<400> SEQUENCE: 45

Lys Asp Glu Leu
1

METHODS AND COMPOSITIONS FOR CONTROLLING PLANT PESTS

CROSS REFERENCE TO RELATED APPLICATIONS

This is a Continuation of U.S. patent application Ser. No. 12/718,059 filed Mar. 5, 2010 and claims the benefit of U.S. Provisional Application Ser. No. 61/158,133, filed Mar. 6, 2009, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "385288_SequenceListing.txt", created on Mar. 3, 2010, and corrected on Dec. 1, 2010 at the request of the Examiner, and having a size of 143 kilobytes and is filed concurrently with the specification. The sequence listing contained in this ASCII formatted document is part of the specification and is herein incorporated by reference in its entirety.

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

*Bacillus thuringiensis* is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiensis* strains or their insecticidal proteins can be used as environmentally-acceptable insecticides to control agricultural insect pests or insect vectors for a variety of human or animal diseases.

Crystal (Cry) proteins (delta-endotoxins) from *Bacillus thuringiensis* have potent insecticidal activity against predominantly Lepidopteran, Dipteran, and Coleopteran larvae. These proteins also have shown activity against Hymenoptera, Homoptera, Phthiraptera, Mallophaga, and Acari pest orders, as well as other invertebrate orders such as Nemathelminthes, Platyhelminthes, and Sarcomastigorphora (Feitelson (1993), *The Bacillus Thuringiensis family tree. Advanced Engineered Pesticides*, Marcel Dekker, Inc., New York, N.Y.). These proteins were originally classified as CryI to CryV based primarily on their insecticidal activity. The major classes were Lepidoptera -specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as Cry1A, Cry1B, Cry1C, etc. Even more closely related proteins within each division were given names such as Cry1C1, Cry1C2, etc.

A new nomenclature was recently described for the Cry genes based upon amino acid sequence homology rather than insect target specificity (Crickmore et al. (1998) *Microbiol. Mol. Biol. Rev.* 62:807-813). In the new classification, each toxin is assigned a unique name incorporating a primary rank (an Arabic number), a secondary rank (an uppercase letter), a tertiary rank (a lowercase letter), and a quaternary rank (another Arabic number). In the new classification, Roman numerals have been exchanged for Arabic numerals in the primary rank. Proteins with less than 45% sequence identity have different primary ranks, and the criteria for secondary and tertiary ranks are 78% and 95%, respectively.

The crystal protein does not exhibit insecticidal activity until it has been ingested and solubilized in the insect midgut. The ingested protoxin is hydrolyzed by proteases in the insect digestive tract to an active toxic molecule. (Höfie and Whiteley (1989) *Microbiol. Rev.* 53:242-255). This toxin binds to apical brush border receptors in the midgut of the target larvae and inserts into the apical membrane creating ion channels or pores, resulting in larval death.

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Aside from delta-endotoxins, there are several other known classes of pesticidal protein toxins. The VIP1/VIP2 toxins (see, for example, U.S. Pat. No. 5,770,696) are binary pesticidal toxins that exhibit strong activity on insects by a mechanism believed to involve receptor-mediated endocytosis followed by cellular toxification, similar to the mode of action of other binary ("A/B") toxins. A/B toxins such as VIP, C2, CDT, CST, or the *B. anthracis* edema and lethal toxins initially interact with target cells via a specific, receptor-mediated binding of "B" components as monomers. These monomers then form homoheptamers. The "B" heptamer-receptor complex then acts as a docking platform that subsequently binds and allows the translocation of an enzymatic "A" component(s) into the cytosol via receptor-mediated endocytosis. Once inside the cell's cytosol, "A" components inhibit normal cell function by, for example, ADP-ribosylation of G-actin, or increasing intracellular levels of cyclic AMP (cAMP). See Barth et al. (2004) *Microbiol Mol Biol Rev* 68:373-402.

The intensive use of *B. thuringiensis*-based insecticides has already given rise to resistance in field populations of the diamondback moth, *Plutella xylostella* (Ferré and Van Rie (2002) Annu. Rev. Entomol. 47:501-533). The most common mechanism of resistance is the reduction of binding of the toxin to its specific midgut receptor(s). This may also confer cross-resistance to other toxins that share the same receptor (Ferré and Van Rie (2002)).

SUMMARY OF THE INVENTION

Compositions and methods for conferring pest resistance to bacteria, plants, plant cells, tissues and seeds are provided. Compositions include nucleic acid molecules encoding sequences for delta-endotoxin polypeptides, vectors comprising those nucleic acid molecules, and host cells comprising the vectors. Compositions also include the polypeptide sequences of the endotoxin, and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise transformed bacteria, plants, plant cells, tissues, and seeds.

In particular, isolated nucleic acid molecules corresponding to delta-endotoxin nucleic acid sequences are provided. Additionally, amino acid sequences corresponding to the polynucleotides are encompassed. In particular, the present invention provides for an isolated nucleic acid molecule comprising a nucleotide sequence encoding the amino acid sequence shown in any of SEQ ID NO:13-24, or a nucleotide sequence set forth in any of SEQ ID NO:1-12, as well as variants and fragments thereof. Nucleotide sequences that are complementary to a nucleotide sequence of the invention, or that hybridize to a sequence of the invention are also encompassed.

The compositions and methods of the invention are useful for the production of organisms with pesticide resistance, specifically bacteria and plants. These organisms and compositions derived from them are desirable for agricultural purposes. The compositions of the invention are also useful for generating altered or improved delta-endotoxin proteins that have pesticidal activity, or for detecting the presence of delta-endotoxin proteins or nucleic acids in products or organisms.

The following embodiments are encompassed by the present invention:

1. A recombinant nucleic acid molecule comprising a nucleotide sequence encoding an amino acid sequence having pesticidal activity, wherein said nucleotide sequence is selected from the group consisting of:
 a) the nucleotide sequence set forth in any of SEQ ID NO:1-12;
 b) a nucleotide sequence that encodes a polypeptide comprising the amino acid sequence of any of SEQ ID NO:13-24; and
 c) a nucleotide sequence that encodes a polypeptide comprising an amino acid sequence having at least 95% sequence identity to the amino acid sequence of any of SEQ ID NO:13-24.

2. The recombinant nucleic acid molecule of embodiment 1, wherein said nucleotide sequence is a synthetic sequence that has been designed for expression in a plant.

3. The recombinant nucleic acid molecule of embodiment 2, wherein said sequence is set forth in any of SEQ ID NO:25-44.

4. The recombinant nucleic acid molecule of claim 1, wherein said nucleotide sequence is operably linked to a promoter capable of directing expression of said nucleotide sequence in a plant cell.

5. A vector comprising the nucleic acid molecule of embodiment 1.

6. The vector of embodiment 5, further comprising a nucleic acid molecule encoding a heterologous polypeptide.

7. A host cell that contains the vector of embodiment 5.

8. The host cell of embodiment 7 that is a bacterial host cell.

9. The host cell of embodiment 7 that is a plant cell.

10. A transgenic plant comprising the host cell of embodiment 9.

11. The transgenic plant of embodiment 10, wherein said plant is selected from the group consisting of maize, sorghum, wheat, cabbage, sunflower, tomato, crucifers, peppers, potato, cotton, rice, soybean, sugarbeet, sugarcane, tobacco, barley, and oilseed rape.

12. A transgenic seed comprising the nucleic acid molecule of embodiment 1.

13. A recombinant polypeptide with pesticidal activity, selected from the group consisting of:
 a) a polypeptide comprising the amino acid sequence of any of SEQ ID NO:13-24;
 b) a polypeptide comprising an amino acid sequence having at least 95% sequence identity to the amino acid sequence of any of SEQ ID NO:13-24; and
 c) a polypeptide that is encoded by any of SEQ ID NO:1-12.

14. The polypeptide of embodiment 13 further comprising heterologous amino acid sequences.

15. A composition comprising the recombinant polypeptide of embodiment 13.

16. The composition of embodiment 15, wherein said composition is selected from the group consisting of a powder, dust, pellet, granule, spray, emulsion, colloid, and solution.

17. The composition of embodiment 15, wherein said composition is prepared by desiccation, lyophilization, homogenization, extraction, filtration, centrifugation, sedimentation, or concentration of a culture of bacterial cells.

18. The composition of embodiment 15, comprising from about 1% to about 99% by weight of said polypeptide.

19. A method for controlling a lepidopteran, coleopteran, heteropteran, nematode, or dipteran pest population comprising contacting said population with a pesticidally-effective amount of the polypeptide of embodiment 13.

20. A method for killing a lepidopteran, coleopteran, heteropteran, nematode, or dipteran pest, comprising contacting said pest with, or feeding to said pest, a pesticidally-effective amount of the polypeptide of embodiment 13.

21. A method for producing a polypeptide with pesticidal activity, comprising culturing the host cell of embodiment 7 under conditions in which the nucleic acid molecule encoding the polypeptide is expressed.

22. A plant having stably incorporated into its genome a DNA construct comprising a nucleotide sequence that encodes a protein having pesticidal activity, wherein said nucleotide sequence is selected from the group consisting of:
 a) the nucleotide sequence set forth in any of SEQ ID NO:1-12;
 b) a nucleotide sequence that encodes a polypeptide comprising the amino acid sequence of any of SEQ ID NO:13-24; and
 c) a nucleotide sequence that encodes a polypeptide comprising an amino acid sequence having at least 95% sequence identity to the amino acid sequence of any of SEQ ID NO:13-24;

wherein said nucleotide sequence is operably linked to a promoter that drives expression of a coding sequence in a plant cell.

23. The plant of embodiment 22, wherein said plant is a plant cell.

24. A method for protecting a plant from a pest, comprising expressing in a plant or cell thereof a nucleotide sequence that encodes a pesticidal polypeptide, wherein said nucleotide sequence is selected from the group consisting of:
 a) the nucleotide sequence set forth in any of SEQ ID NO:1-12;
 b) a nucleotide sequence that encodes a polypeptide comprising the amino acid sequence of any of SEQ ID NO:13-24; and
 c) a nucleotide sequence that encodes a polypeptide comprising an amino acid sequence having at least 95% sequence identity to the amino acid sequence of any of SEQ ID NO:13-24.

25. The method of embodiment 24, wherein said plant produces a pesticidal polypeptide having pesticidal activity against a lepidopteran, coleopteran, heteropteran, nematode, or dipteran pest.

26. A method for increasing yield in a plant comprising growing in a field a plant of or a seed thereof having stably incorporated into its genome a DNA construct comprising a nucleotide sequence that encodes a protein having pesticidal activity, wherein said nucleotide sequence is selected from the group consisting of:

a) the nucleotide sequence set forth in any of SEQ ID NO:1-12;

b) a nucleotide sequence that encodes a polypeptide comprising the amino acid sequence of any of SEQ ID NO:13-24; and c) a nucleotide sequence that encodes a polypeptide comprising an amino acid sequence having at least 95% sequence identity to the amino acid sequence of any of SEQ ID NO:13-24;

wherein said field is infested with a pest against which said polypeptide has pesticidal activity.

DETAILED DESCRIPTION

The present invention is drawn to compositions and methods for regulating pest resistance in organisms, particularly plants or plant cells. The methods involve transforming organisms with a nucleotide sequence encoding a delta-endotoxin protein of the invention. In particular, the nucleotide sequences of the invention are useful for preparing plants and microorganisms that possess pesticidal activity. Thus, transformed bacteria, plants, plant cells, plant tissues and seeds are provided. Compositions are delta-endotoxin nucleic acids and proteins of *Bacillus thuringiensis*. The sequences find use in the construction of expression vectors for subsequent transformation into organisms of interest, as probes for the isolation of other delta-endotoxin genes, and for the generation of altered pesticidal proteins by methods known in the art, such as domain swapping or DNA shuffling. The proteins find use in controlling or killing lepidopteran, coleopteran, and nematode pest populations, and for producing compositions with pesticidal activity.

By "delta-endotoxin" is intended a toxin from *Bacillus thuringiensis* that has toxic activity against one or more pests, including, but not limited to, members of the Lepidoptera, Diptera, and Coleoptera orders or members of the Nematoda phylum, or a protein that has homology to such a protein. In some cases, delta-endotoxin proteins have been isolated from other organisms, including *Clostridium bifermentans* and *Paenibacillus popilliae*. Delta-endotoxin proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein.

In various embodiments, the sequences disclosed herein have homology to delta-endotoxin proteins. Delta-endotoxins include proteins identified as cry1 through cry53, cyt1 and cyt2, and Cyt-like toxin. There are currently over 250 known species of delta-endotoxins with a wide range of specificities and toxicities. For an expansive list see Crickmore et al. (1998), *Microbiol. Mol. Biol. Rev.* 62:807-813, and for regular updates see Crickmore et al. (2003) "*Bacillus thuringiensis* toxin nomenclature," at www.biols.susx.ac.uk/Home/Neil_Crickmore/Bt/index.

In other embodiments, the sequences encompassed herein are MTX-like sequences. The term "MTX" is used in the art to delineate a set of pesticidal proteins that are produced by *Bacillus sphaericus*. The first of these, often referred to in the art as MTX1, is synthesized as a parasporal crystal which is toxic to mosquitoes. The major components of the crystal are two proteins of 51 and 42 kDa. Since the presence of both proteins are required for toxicity, MTX1 is considered a "binary" toxin (Baumann et al. (1991) *Microbiol. Rev.* 55:425-436).

By analysis of different *Bacillus sphaericus* strains with differing toxicities, two new classes of MTX toxins have been identified. MTX2 and MTX3 represent separate, related classes of pesticidal toxins that exhibit pesticidal activity. See, for example, Baumann et al. (1991) *Microbiol. Rev.* 55:425-436, herein incorporated by reference in its entirety. MTX2 is a 100-kDa toxin. More recently MTX3 has been identified as a separate toxin, though the amino acid sequence of MTX3 from *B. sphaericus* is 38% identical to the MTX2 toxin of *B. sphaericus* SSII-1 (Liu, et al. (1996) *Appl. Environ. Microbiol.* 62:2174-2176). Mtx toxins may be useful for both increasing the insecticidal activity of *B. sphaericus* strains and managing the evolution of resistance to the Bin toxins in mosquito populations (Wirth et al. (2007) Appl Environ Microbiol 73(19):6066-6071).

Provided herein are novel isolated nucleotide sequences that confer pesticidal activity. Also provided are the amino acid sequences of the delta-endotoxin proteins. The 10 protein resulting from translation of this gene allows cells to control or kill pests that ingest it.

Isolated Nucleic Acid Molecules, and Variants and Fragments Thereof

One aspect of the invention pertains to isolated or recombinant nucleic acid molecules comprising nucleotide sequences encoding delta-endotoxin proteins and polypeptides or biologically active portions thereof, as well as nucleic acid molecules sufficient for use as hybridization probes to identify delta-endotoxin encoding nucleic acids. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid sequence (or DNA) is used herein to refer to a nucleic acid sequence (or DNA) that is no longer in its natural environment, for example in an in vitro or in a recombinant bacterial or plant host cell. In some embodiments, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated delta-endotoxin encoding nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A delta-endotoxin protein that is substantially free of cellular material includes preparations of protein having less than about 30%, 20%, 10%, or 5% (by dry weight) of non-delta-endotoxin protein (also referred to herein as a "contaminating protein").

Nucleotide sequences encoding the proteins of the present invention include the sequence set forth in SEQ ID NO:1-12, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the delta-endotoxin protein encoded by this nucleotide sequence are set forth in SEQ ID NO:13-24.

Nucleic acid molecules that are fragments of these delta-endotoxin encoding nucleotide sequences are also encompassed by the present invention. By "fragment" is intended a portion of the nucleotide sequence encoding a delta-endotoxin protein. A fragment of a nucleotide sequence may encode a biologically active portion of a delta-endotoxin protein, or it may be a fragment that can be used as a hybridization probe or PCR primer using methods disclosed below. Nucleic acid molecules that are fragments of a delta-endotoxin nucleotide sequence comprise at least about 50, 100, 200, 300, 400, 500, 600, 700, 800, 900, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350 contiguous nucleotides, or up to the number of nucleotides present in a full-length delta-endotoxin encoding nucleotide sequence disclosed herein depending upon the intended use. By "contiguous" nucleotides is intended nucleotide residues that are immediately adjacent to one another. Fragments of the nucleotide sequences of the present invention will encode protein fragments that retain the biological activity of the delta-endotoxin protein and, hence, retain pesticidal activity. By "retains activity" is intended that the fragment will have at least about 30%, at least about 50%, at least about 70%, 80%, 90%, 95% or higher of the pesticidal activity of the delta-endotoxin protein. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a delta-endotoxin encoding nucleotide sequence that encodes a biologically active portion of a protein of the invention will encode at least about 15, 25, 30, 50, 75, 100, 125, 150, 175, 200, 250, 300, 350, 400, 450, 500, 550, 600, 650, 700, 750, 800, 850, 900, 950, 1000, 1050, 1100 contiguous amino acids, or up to the total number of amino acids present in a full-length delta-endotoxin protein of the invention. In some embodiments, the fragment is a proteolytic cleavage fragment. For example, the proteolytic cleavage fragment may have an N-terminal or a C-terminal truncation of at least about 100 amino acids, about 120, about 130, about 140, about 150, or about 160 amino acids relative to SEQ ID NO:13-24. In some embodiments, the fragments encompassed herein result from the removal of the C-terminal crystallization domain, e.g., by proteolysis or by insertion of a stop codon in the coding sequence.

Preferred delta-endotoxin proteins of the present invention are encoded by a nucleotide sequence sufficiently identical to the nucleotide sequence of SEQ ID NO:1-12. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the comparison is across the entirety of the reference sequence (e.g., across the entirety of one of SEQ ID NO:1-12, or across the entirety of one of SEQ ID NO:13-24). The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to delta-endotoxin-like nucleic acid molecules of the invention. BLAST protein searches can be performed with the BLASTX program, score=50, wordlength=3, to obtain amino acid sequences homologous to delta-endotoxin protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM 120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules. "Variants" of the delta-endotoxin encoding nucleotide sequences include those sequences that encode the delta-endotoxin proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the delta-endotoxin proteins disclosed in the present invention as discussed below. Variant proteins encompassed by the present invention are biologically active, that is they continue to possess the desired biological activity of the native protein, that is, retaining pesticidal activity. By "retains activity" is intended that the variant will have at least about 30%, at least about 50%, at least about 70%, or at least about 80% of the pesticidal activity of the native protein. Methods for measuring pesticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

The skilled artisan will further appreciate that changes can be introduced by mutation of the nucleotide sequences of the invention thereby leading to changes in the amino acid sequence of the encoded delta-endotoxin proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted, nonessential amino acid residues. A "nonessential" amino acid residue is a residue that can be altered from the wild-type sequence of a delta-endotoxin protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of the amino acid sequences of the present invention and known delta-endotoxin sequences. Examples of residues that are conserved but that may allow conservative amino acid substitutions and still retain activity include, for example, residues that have only conservative substitutions between all proteins contained in an alignment of the amino acid sequences of the present invention and known delta-endotoxin sequences. However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer delta-endotoxin activity to identify mutants that retain activity. Following mutagenesis, the encoded protein can be expressed recombinantly, and the activity of the protein can be determined using standard assay techniques.

Using methods such as PCR, hybridization, and the like corresponding delta-endotoxin sequences can be identified, such sequences having substantial identity to the sequences of the invention. See, for example, Sambrook and Russell (2001) *Molecular Cloning: A Laboratory Manual.* (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the delta-endotoxin nucleotide sequence can be used to screen cDNA or genomic libraries. Methods for construction of such cDNA and genomic libraries are generally known in the art and are disclosed in Sam brook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known delta-endotoxin-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, 200, 250, 300, 350, or 400 consecutive nucleotides of delta-endotoxin encoding nucleotide sequence of the invention or a fragment or variant thereof. Methods for the preparation of probes for hybridization are generally known in the art and are disclosed in Sambrook and Russell, 2001, supra herein incorporated by reference.

For example, an entire delta-endotoxin sequence disclosed herein, or one or more portions thereof, may be used as a probe capable of specifically hybridizing to corresponding delta-endotoxin-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding delta-endotoxin sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaC1/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Delta-endotoxin proteins are also encompassed within the present invention. By "delta-endotoxin protein" is intended a protein having the amino acid sequence set forth in SEQ ID NO:13-24. Fragments, biologically active portions, and variants thereof are also provided, and may be used to practice the methods of the present invention. An "isolated protein" is used to refer to a protein that is no longer in its natural environment, for example in vitro or in a recombinant bacterial or plant host cell. An "isolated protein" is used to refer to a protein that is no longer in its natural environment, for example in vitro or in a recombinant bacterial or plant host cell.

"Fragments" or "biologically active portions" include polypeptide fragments comprising amino acid sequences sufficiently identical to the amino acid sequence set forth in any of SEQ ID NO:13-24 and that exhibit pesticidal activity. A biologically active portion of a delta-endotoxin protein can be a polypeptide that is, for example, 10, 25, 50, 100 or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of SEQ ID NO:13-24. The invention encompasses other fragments, however, such as any fragment in the protein greater than about 10, 20, 30, 50, 100, 150, 200, 250, 300, 350, 400, 400, 450, 500, 550, 600, 650, 700, 750, 800, 850, 900, 950, 1000, 1050, 1100, 1150, 1200, 1250, or 1300 amino acids.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of any of SEQ ID NO:13-24. Variants also include polypeptides encoded by a nucleic acid molecule that hybridizes to the nucleic acid molecule of SEQ ID NO:1-12, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining pesticidal activity. In some embodiments, the variants have improved activity relative to the native protein. Methods for measuring pesticidal activity are well known in the art. See, for example, Czapla and Lang (1990) J. Econ. Entomol. 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

Bacterial genes, such as the axmi genes of this invention, quite often possess multiple methionine initiation co dons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may also lead to generation of delta-endotoxin proteins that encode pesticidal activity. These delta-endotoxin proteins are encompassed in the present invention and may be used in the methods of the present invention.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; and U.S. Pat. No. 4,196,265).

Altered or Improved Variants

It is recognized that DNA sequences of a delta-endotoxin may be altered by various methods, and that these alterations may result in DNA sequences encoding proteins with amino acid sequences different than that encoded by a delta-endotoxin of the present invention. This protein may be altered in various ways including amino acid substitutions, deletions, truncations, and insertions of one or more amino acids of SEQ 10 NO:13-24, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130 or more amino acid substitutions, deletions or insertions.

Methods for such manipulations are generally known in the art. For example, amino acid sequence variants of a delta-endotoxin protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a delta-endotoxin to confer pesticidal activity may be improved by the use of such techniques upon the compositions of this invention. For example, one may express a delta-endotoxin in host cells that exhibit high rates of base misincorporation during DNA replication, such as XL-1 Red (Stratagene). After propagation in such strains, one can isolate the delta-endotoxin DNA (for example by preparing plasmid DNA, or by amplifying by PCR and cloning the resulting PCR fragment into a vector), culture the delta-endotoxin mutations in a non-mutagenic strain, and identify mutated delta-endotoxin genes with pesticidal activity, for example by performing an assay to test for pesticidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different delta-endotoxin protein coding regions can be used to create a new delta-endotoxin protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a delta-endotoxin gene of the invention and other known delta-endotoxin genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered delta-endotoxin proteins. Domains II and III may be swapped between delta-endotoxin proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem.* 265:20923-20930; Rang et al. 91999) *Appl. Environ. Microbiol.* 65:2918-2925).

Vectors

A delta-endotoxin sequence of the invention may be provided in an expression cassette for expression in a plant of interest. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the delta-endotoxin sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (Le., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

In one embodiment, the delta-endotoxin is targeted to the chloroplast for expression. In this manner, where the delta-endotoxin is not directly inserted into the chloroplast, the expression cassette will additionally contain a nucleic acid encoding a transit peptide to direct the delta-endotoxin to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The delta-endotoxin gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

The transgenic plants of the invention express one or more of the pesticidal sequences disclosed herein. In various embodiments, the transgenic plant further comprises one or more additional genes for insect resistance, for example, one or more additional genes for controlling coleopteran, lepidopteran, heteropteran, or nematode pests. It will be understood by one of skill in the art that the transgenic plant may comprise any gene imparting an agronomic trait of interest.

Transformation of plant cells can be accomplished by one of several techniques known in the art. The delta-endotoxin gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the delta-endotoxin are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}P$ target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the delta-endotoxin is then tested by hybridizing the filter to a radioactive probe derived from a delta-endotoxin, by methods known in the art (Sambrook and Russell, 2001, supra).

Western blot, biochemical assays and the like may be carried out on the transgenic plants to confirm the presence of protein encoded by the delta-endotoxin gene by standard procedures (Sambrook and Russell, 2001, supra) using antibodies that bind to one or more epitopes present on the delta-endotoxin protein.

Pesticidal Activity in Plants

In another aspect of the invention, one may generate transgenic plants expressing a delta-endotoxin that has pesticidal activity. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a delta-endotoxin may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pesticidal activity.

Fertile plants expressing a delta-endotoxin may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape., etc.).

Use in Pest Control

General methods for employing strains comprising a nucleotide sequence of the present invention, or a variant thereof, in pesticide control or in engineering other organisms as pesticidal agents are known in the art. See, for example U.S. Pat. No. 5,039,523 and EP 0480762A2.

The *Bacillus* strains containing a nucleotide sequence of the present invention, or a variant thereof, or the microorganisms that have been genetically altered to contain a pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a delta-endotoxin gene into a cellular host. Expression of the delta-endotoxin gene results, directly or indirectly, in the intracellular production and maintenance of the pesticide. In one aspect of this invention, these cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing a gene of this invention such as to allow application of the resulting material as a pesticide.

Pesticidal Compositions

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient of the present invention or an agrochemical composition of the present invention that contains at least one of the pesticidal proteins produced by the bacterial strains of the present invention include leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran, coleopteran, or nematode pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

The plants can also be treated with one or more chemical compositions, including one or more herbicide, insecticides, or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halosulfuron Gowan, Paraquat, Propyzamide, Sethoxydim, Butafenacil, Halosulfuron, Indaziflam; Fruits/Vegetables Insecticides: Aldicarb, *Bacillus thuriengiensis*, Carbaryl, Carbofuran, Chlorpyrifos, Cypermethrin, Deltamethrin, Diazinon, Malathion, Abamectin, Cyfluthrinlbeta-cyfluthrin, Esfenvalerate, Lambda-cyhalothrin, Acequinocyl, Bifenazate, Methoxyfenozide, Novaluron, Chromafenozide, Thiacloprid, Dinotefuran, Fluacrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, Indoxacarb, Forthiazate, Fenamiphos, Cadusaphos, Pyriproxifen, Fenbutatin-oxid, Hexthiazox, Methomyl, 4-[[(6-Chlorpyridin-3-yl)methyl](2,2-difluorethyl)amino]furan-2(5H)-on; Fruits/Vegetables Fungicides: Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cytlufenamid, Boscalid; Cereals Herbicides: Isoproturon, Bromoxynil, Ioxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim—methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cytluthrin, Bifenthrin, Imidacloprid, Clothianidin, Thiamethoxam, Thiacloprid, Acetamiprid, Dinetofuran, Clorphyriphos, Metamidophos, Oxidemethon-methyl, Pirimicarb, Methiocarb; Maize Herbicides: Atrazine, Alachlor, Bromoxynil, Acetochlor, Dicamba, Clopyralid, (S—)Dimethenamid, Glufosinate, Glyphosate, Isoxaflutole, (S—)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxytluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflurnuron, Rynaxypyr, Beta-Cyfluthrin, Spirotetramat, Clothianidin, Thiamethoxarn, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Tritluralin, Chlorimuron-Ethyl, Cloransulam-Methyl, Fenoxaprop, Fomesafen, Fluazifop, Glyphosate, Imazamox, Imazaquin, Imazethapyr, (S—)Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides: Carbofuran, Organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

"Pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrinidae. Superfamily Hydrophiloidea includes the family Hydrophilidae. Superfamily Staphylinoidea includes the families Silphidae and Staphylinidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachimidae, Anthomyiidae, Muscidae, Calliphoridae, and Sarcophagidae.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, and Tineidae.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Insect pests of the invention for the major crops include: Maize: *Ostrinia nubilalis*, European corn borer; *Agrotis ipsilon*, black cutworm; *Helicoverpa zea*, corn earworm; *Spodoptera/rugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera, frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus* leucopterus, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera rugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape *colaspis; Lissorhoptrus oryzophilus*, rice water weevil; *Sitophilus oryzae*, rice weevil; *Nephotettix nigropictus*, rice leafhopper; *Blissus leucopterus* leucopterus, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus* leucopterus, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with a pest against which said polypeptide has pesticidal activity. In some embodiments, the polypeptide has pesticidal activity against a lepidopteran, coleopteran, dipteran, hemipteran, or nematode pest, and said field is infested with a lepidopteran, hemipteran, coleopteran, dipteran, or nematode pest.

As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

In specific methods, plant yield is increased as a result of improved pest resistance of a plant expressing a pesticidal protein disclosed herein. Expression of the pesticidal protein results in a reduced ability of a pest to infest or feed on the plant, thus improving plant yield.

The following examples are offered by way of illustration and not by way of limitation.

EXPERIMENTAL

EXAMPLE 1

Discovery of Novel Toxin Genes from *Bacillus thuringiensis* Strain ATX15903

Novel pesticidal genes are identified from the bacterial strains listed in Table 1 using methods such as:

Method 1

- Preparation of extrachromosomal DNA from the strain, which includes plasmids that typically harbor delta-endotoxin genes
- Mechanical shearing of extrachromosomal DNA to generate size-distributed fragments
- Cloning of ~2 Kb to ~10 Kb fragments of extrachromosomal DNA
- Outgrowth of ~1500 clones of the extrachromosomal DNA
- Partial sequencing of the 1500 clones using primers specific to the cloning vector (end reads)
- Identification of putative toxin genes via homology analysis via the MiDAS approach (as described in U.S. Patent Publication No. 20040014091, which is herein incorporated by reference in its entirety)
- Sequence finishing (walking) of clones containing fragments of the putative toxin genes of interest Method 2

- Preparation of extrachromosomal DNA from the strain (which contains a mixture of some or all of the following: plasmids of various size; phage chromosomes; genomic DNA fragments not separated by the purification protocol; other uncharacterized extrachromosomal molecules)
- Mechanical or enzymatic shearing of the extrachromosomal DNA to generate size-distributed fragments
- Sequencing of the fragmented DNA by high-throughput pyrosequencing methods
- Identification of putative toxin genes via homology and/or other computational analyses

TABLE 1

Novel pesticidal genes from Strain ATX15903

| Gene | Molecular Weight (kDa) and Length (amino acids) | Nucleotide SEQ ID NO: | Amino Acid SEQ ID NO: | Percent Identity to Closest Sequence in Art | Closest Sequence in Art |
|---|---|---|---|---|---|
| axmi077 | 141.6, 1249 | 1 | 13 | 35.3%<br>32.5% | Cry43Ba1<br>axmi087 |
| axmi078 | 91.9, 820 | 2 | 14 | 28.7%<br>26% | Cry24Ba1<br>axmi014 |
| axmi083 | 79.8, 710 | 3 | 15 | 75.2%<br>32% | Cry30Aa1<br>axmi007 |
| axmi084 | 63.8, 563 | 4 | 16 | 84.3%<br>87% | Cry39Orf2<br>axmi086 |
| axmi085 | 77.7, 690 | 5 | 17 | 31.7%<br>66% | Cry8Aa1<br>axmi009 |
| axmi086 | 64.6, 571 | 6 | 18 | 85.2%<br>88% | Cry39Orf2<br>axmi090 |
| axmi089 | 69.4, 627 | 7 | 19 | 36%<br>31% | Cry29Aa1<br>axmi085 |
| axmi090 | 64.3, 566 | 8 | 20 | 85.9%<br>89% | Cry39orf2<br>axmi086 |
| axmi094 | 33.0, 296 | 9 | 21 | 19.8%<br>26% | Mtx3<br>axmi095 |
| axmi095 | 34.4 308 | 10 | 22 | 22.3%<br>26% | Mtx2<br>axmi094 |
| Axmi105 | 141.2, 1244 | 11 | 23 | 37%<br>74% | Cry43Aa2<br>axmi077 |
| axmi0106 | 58.0, 521 | 12 | 24 | 58% | Cyt1Ca1 |

EXAMPLE 2

Expression in *Bacillus*

The insecticidal gene disclosed herein is amplified by PCR from pAX980, and the PCR product is cloned into the *Bacillus* expression vector pAX916, or another suitable vector, by methods well known in the art. The resulting *Bacillus* strain, containing the vector with axmi gene is cultured on a conventional growth media, such as CYS media (10 g/l Bacto-casitone; 3 g/l yeast extract; 6 g/l $KH_2PO_4$; 14 g/l $K_2HPO_4$; 0.5 mM $MgSO_4$; 0.05 mM $MnCl_2$; 0.05 mM $FeSO_4$), until sporulation is evident by microscopic examination. Samples are prepared and tested for activity in bioassays.

EXAMPLE 3

Construction of Synthetic Sequences

In one aspect of the invention, synthetic axmi sequences were generated. These synthetic sequences have an altered DNA sequence relative to the parent axmi sequence, and encode a protein that is collinear with the parent AXMI protein to which it corresponds, but lacks the C-terminal "crystal domain" present in many delta-endotoxin proteins. Synthetic genes are presented in Table 2.

TABLE 2

| Wildtype Gene Name | Synthetic Gene Name | SEQ ID NO: |
|---|---|---|
| axmi077 | axmi077bv01 | 25 |
| | axmi077bv02 | 26 |
| axmi078 | axmi078bv01 | 27 |
| | axmi078bv02 | 28 |
| axmi083 | axmi083_1bv01 | 29 |
| | axmi083_1bv02 | 30 |
| | axmi083_2bv01 | 31 |
| | axmi083_2bv02 | 32 |
| axmi085 | axmi085bv01 | 33 |
| | axmi085bv02 | 34 |
| axmi089 | axmi089bv01 | 35 |
| | axmi089bv02 | 36 |
| axmi094 | axmi094bv01 | 37 |
| | axmi094bv02 | 38 |
| axmi095 | axmi095bv01 | 39 |
| | axmi095bv02 | 40 |
| asmi105 | axmi105bv01 | 41 |
| axmi106 | axmi106bv01 | 43 |
| | axmi106bv02 | 44 |

In another aspect of the invention, modified versions of synthetic genes are designed such that the resulting peptide is targeted to a plant organelle, such as the endoplasmic reticulum or the apoplast. Peptide sequences known to result in targeting of fusion proteins to plant organelles are known in the art. For example, the N-terminal region of the acid phosphatase gene from the White Lupin *Lupinus albus* (Genebank ID GI:14276838; Miller et al. (2001). Plant Physiology 127: 594-606) is known in the art to result in endoplasmic reticulum targeting of heterologous proteins. If the resulting fusion protein also contains an endoplasmic retention sequence comprising the peptide N-terminus-lysine-aspartic acid-glutamic acid-leucine (i.e. the “KDEL” motif (SEQ ID NO:45) at the C-terminus, the fusion protein will be targeted to the endoplasmic reticulum. If the fusion protein lacks an endoplasmic reticulum targeting sequence at the C-terminus, the protein will be targeted to the endoplasmic reticulum, but will ultimately be sequestered in the apoplast.

EXAMPLE 4

Assays for Pesticidal Activity

The ability of a pesticidal protein to act as a pesticide upon a pest is often assessed in a number of ways. One way well known in the art is to perform a feeding assay. In such a feeding assay, one exposes the pest to a sample containing either compounds to be tested, or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson, J. L. & H. K. Preisler. 1992. *Pesticide bioassays, with arthropods*. CRC, Boca Raton, Fla. Alternatively, assays are commonly described in the journals “Arthropod Management Tests” and “Journal of Economic Entomology” or by discussion with members of the Entomological Society of America (ESA).

EXAMPLE 5

Vectoring of the Pesticidal Genes of the Invention for Plant Expression

Each of the coding regions of the genes of the invention are connected independently with appropriate promoter and terminator sequences for expression in plants. Such sequences are well known in the art and may include the rice actin promoter or maize ubiquitin promoter for expression in monocots, the *Arabidopsis* UBQ3 promoter or CaMV $^{35}$S promoter for expression in dicots, and the nos or PinII terminators. Techniques for producing and confirming promoter-gene-terminator constructs also are well known in the art.

EXAMPLE 6

Transformation of the Genes of the Invention into Plant Cells by *Agrobacterium*-Mediated Transformation Ears are collected 8 to 12 days after pollination. Embryos are isolated from the ears, and those embryos 0.8-1.5 mm in size are used for transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for 5 to 10 minutes, and then plated onto co-cultivation media for 3 days (25° C. in the dark). After co-cultivation, explants are transferred to recovery period media for five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

EXAMPLE 7

Transformation of Maize Cells with the Pesticidal Genes of the Invention

Maize ears are collected 8 to 12 days after pollination. Embryos are isolated from the ears, and those embryos 0.8-1.5 mm in size are used for transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casaminoacids;

50 g/L sucrose; 1 mL/L (of 1 mg/mL Stock) 2,4-D), and incubated overnight at 25° C. in the dark.

The resulting explants are transferred to mesh squares (30-40 per plate), transferred onto osmotic media for 30-45 minutes, then transferred to a beaming plate (see, for example, PCT Publication No. WO/0138514 and U.S. Pat. No. 5,240,842).

DNA constructs designed to express the genes of the invention in plant cells are accelerated into plant tissue using an aerosol beam accelerator, using conditions essentially as described in PCT Publication No. WO/0138514. After beaming, embryos are incubated for 30 min on osmotic media, then placed onto incubation media overnight at 25° C. in the dark. To avoid unduly damaging beamed explants, they are incubated for at least 24 hours prior to transfer to recovery media. Embryos are then spread onto recovery period media, for 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

DN62A5S Media

| Component | per liter | Source |
|---|---|---|
| Chu'S N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casaminoacids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

Adjust the pH of the solution to pH to 5.8 with 1N KOH/1N KCl, add Gelrite (Sigma) to 3 g/L, and autoclave. After cooling to 50° C., add 2 ml/L of a 5 mg/ml stock solution of Silver Nitrate (Phytotechnology Labs). Recipe yields about 20 plates.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated nucleic acid molecule comprising a nucleotide sequence encoding an amino acid sequence having pesticidal activity, wherein said nucleotide sequence is selected from the group consisting of:

a) a nucleotide sequence that encodes a polypeptide comprising the amino acid sequence of SEQ ID NO: 24; and b) a nucleotide sequence that encodes a polypeptide comprising an amino acid sequence having at least 95% sequence identity to the amino acid sequence of SEQ ID NO: 24.

2. The isolated nucleic acid molecule of claim 1, wherein said nucleotide sequence is a synthetic sequence that has been designed for expression in a plant.

3. The isolated nucleic acid molecule of claim 2, wherein said nucleotide sequence is SEQ ID NO:44.

4. A vector comprising the nucleic acid molecule of claim 1.

5. The vector of claim 4, further comprising a nucleic acid molecule encoding a heterologous polypeptide.

6. A host cell transformed with the nucleic acid molecule of claim 1.

7. The host cell of claim 6, wherein the host cell is a bacterial host cell.

8. The host cell of claim 6, wherein the host cell is a plant cell.

9. A method for producing a polypeptide with pesticidal activity, comprising culturing the host cell of claim 6 under conditions in which the nucleic acid molecule encoding the polypeptide is expressed.

10. A transgenic seed comprising the nucleic acid molecule of claim 1.

11. A nucleic acid molecule comprising a nucleotide sequence encoding an amino acid sequence having pesticidal activity, wherein said nucleotide sequence is selected from the group consisting of:

a) a nucleotide sequence that encodes a polypeptide comprising the amino acid sequence of SEQ ID NO: 24; and b) a nucleotide sequence that encodes a polypeptide comprising an amino acid sequence having at least 95% sequence identity to the amino acid sequence of SEQ ID NO: 24, wherein said nucleotide sequence is operably linked to a promoter capable of directing expression of said nucleotide sequence in a plant cell.

12. A transgenic plant comprising a plant cell, wherein the plant cell comprises the nucleic acid molecule of claim 11.

13. The transgenic plant of claim 12, wherein said plant is selected from the group consisting of maize, sorghum, wheat, cabbage, sunflower, tomato, crucifers, peppers, potato, cotton, rice, soybean, sugarbeet, sugarcane, tobacco, barley, and oilseed rape.

14. A plant having stably incorporated into its genome a DNA construct comprising a nucleotide sequence that encodes a protein having pesticidal activity, wherein said nucleotide sequence is selected from the group consisting of:

a) a nucleotide sequence that encodes a polypeptide comprising the amino acid sequence of SEQ ID NO: 24; and b) a nucleotide sequence that encodes a polypeptide comprising an amino acid sequence having at least 95% sequence identity to the amino acid sequence of SEQ ID NO: 24;

wherein said nucleotide sequence is operably linked to a promoter that drives expression of a coding sequence in a plant cell.

15. The plant of claim 14, wherein said plant is a plant cell.

16. A method for protecting a plant from a pest, comprising expressing in a plant a nucleotide sequence that encodes a pesticidal polypeptide, wherein said nucleotide sequence is selected from the group consisting of:

a) a nucleotide sequence that encodes a polypeptide comprising the amino acid sequence of SEQ ID NO: 24; and b) a nucleotide sequence that encodes a polypeptide comprising an amino acid sequence having at least 95% sequence identity to the amino acid sequence of SEQ ID NO: 24.

17. The method of claim 16, wherein said plant produces a pesticidal polypeptide having pesticidal activity against a lepidopteran, coleopteran, heteropteran, nematode, or dipteran pest.

18. A method for increasing yield in a plant comprising growing in a field a plant having stably incorporated into its genome a DNA construct comprising a nucleotide sequence that encodes a protein having pesticidal activity, wherein said nucleotide sequence is selected from the group consisting of:

a) a nucleotide sequence that encodes a polypeptide comprising the amino acid sequence of SEQ ID NO: 24; and b) a nucleotide sequence that encodes a polypeptide comprising an amino acid sequence having at least 95% sequence identity to the amino acid sequence of SEQ ID NO: 24;

wherein said field is infested with a pest against which said polypeptide has pesticidal activity.

19. A method for protecting a plant from a pest, comprising expressing in at least one cell in a plant a nucleotide sequence that encodes a pesticidal polypeptide, wherein said nucleotide sequence is selected from the group consisting of:

a) a nucleotide sequence that encodes a polypeptide comprising the amino acid sequence of SEQ ID NO: 24; and b) a nucleotide sequence that encodes a polypeptide comprising an amino acid sequence having at least 95% sequence identity to the amino acid sequence of SEQ ID NO: 24.

* * * * *